(12) United States Patent
Lighton et al.

(10) Patent No.: US 11,215,624 B2
(45) Date of Patent: Jan. 4, 2022

(54) FLUID MONITORING SYSTEMS AND METHODS

(71) Applicants: Paul Lighton, Aledo, IL (US); Joshua Lighton, Davenport, IA (US)

(72) Inventors: Paul Lighton, Aledo, IL (US); Joshua Lighton, Davenport, IA (US)

( * ) Notice: Subject to any disclaimer, the term of this patent is extended or adjusted under 35 U.S.C. 154(b) by 0 days.

(21) Appl. No.: 17/145,149

(22) Filed: Jan. 8, 2021

(65) Prior Publication Data

US 2021/0208173 A1 Jul. 8, 2021

Related U.S. Application Data

(60) Provisional application No. 63/056,355, filed on Jul. 24, 2020, provisional application No. 62/958,418, filed on Jan. 8, 2020.

(51) Int. Cl.
*G01N 35/00* (2006.01)

(52) U.S. Cl.
CPC .............................. *G01N 35/00623* (2013.01)

(58) Field of Classification Search
CPC ................................................ G01N 35/00623
USPC ....................................................... 73/64.56
See application file for complete search history.

(56) References Cited

U.S. PATENT DOCUMENTS

| | | | |
|---|---|---|---|
| 4,626,992 A | 12/1986 | Greaves et al. | |
| 5,242,602 A | 9/1993 | Richardson et al. | |
| 5,315,880 A | 5/1994 | Bailey | |
| 5,386,373 A | 1/1995 | Keeler et al. | |
| 5,451,314 A | 9/1995 | Neuenschwander | |
| 2014/0155867 A1 | 6/2014 | Lee | |

OTHER PUBLICATIONS https://www.hach.com/asset-get.download.jsa?id=12684926900 ; "Source Water Panel Drawing", 2017.*
https://www.hach.com/asset-get.download.jsa?id=12684926900; "2610 Source Water Panel", 2012.*

* cited by examiner

*Primary Examiner* — John Fitzgerald
*Assistant Examiner* — Rodney T Frank
(74) *Attorney, Agent, or Firm* — Hamilton IP Law, PC; Jay R. Hamilton; Charles A. Damschen

(57) ABSTRACT

An illustrative embodiment of a flow cell may include a main chamber, base plate, and cover. The main chamber may be formed with an interior portion having a first angled surface, a first ramp, a second ramp, and a second angled surface. A secondary drain may be positioned at a point of relatively low elevation between the bottom portions of the first and second ramps. The main chamber may include first, second, and third inlet passages that may be in fluid communication with an inlet header formed in the base plate. A PLC and/or PAC may be in communication with various components of the flow cell and/or external components for monitoring, sensing, and/or providing other functionality.

20 Claims, 87 Drawing Sheets

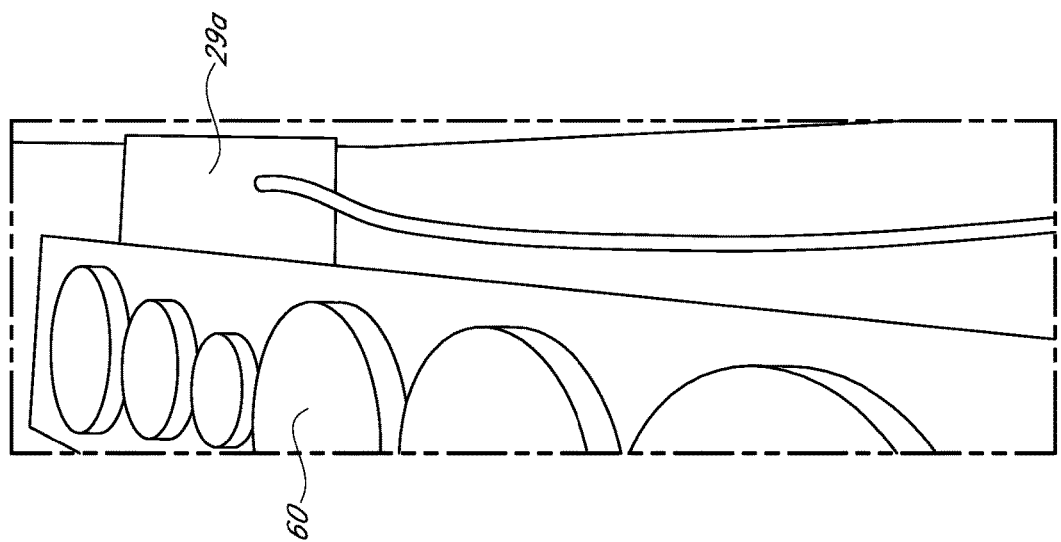

- 5/8-24
- Pitch 24

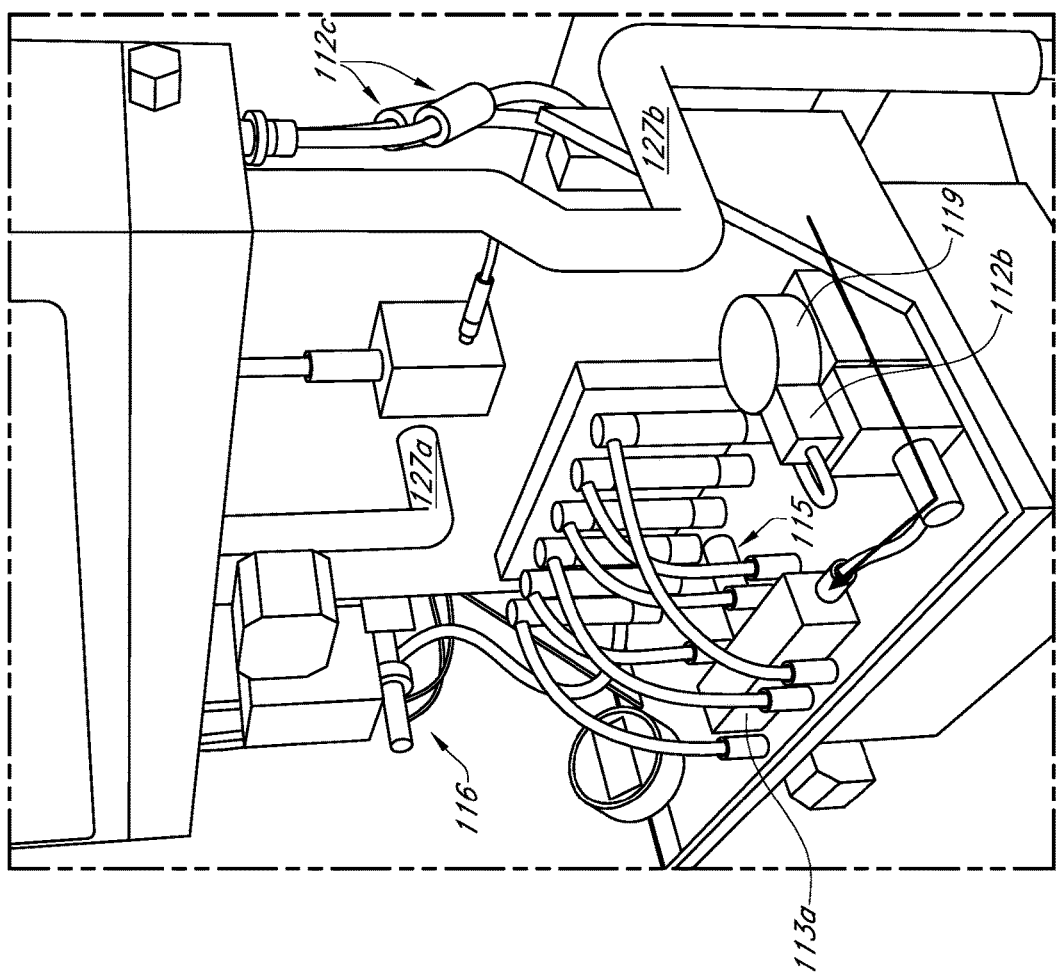

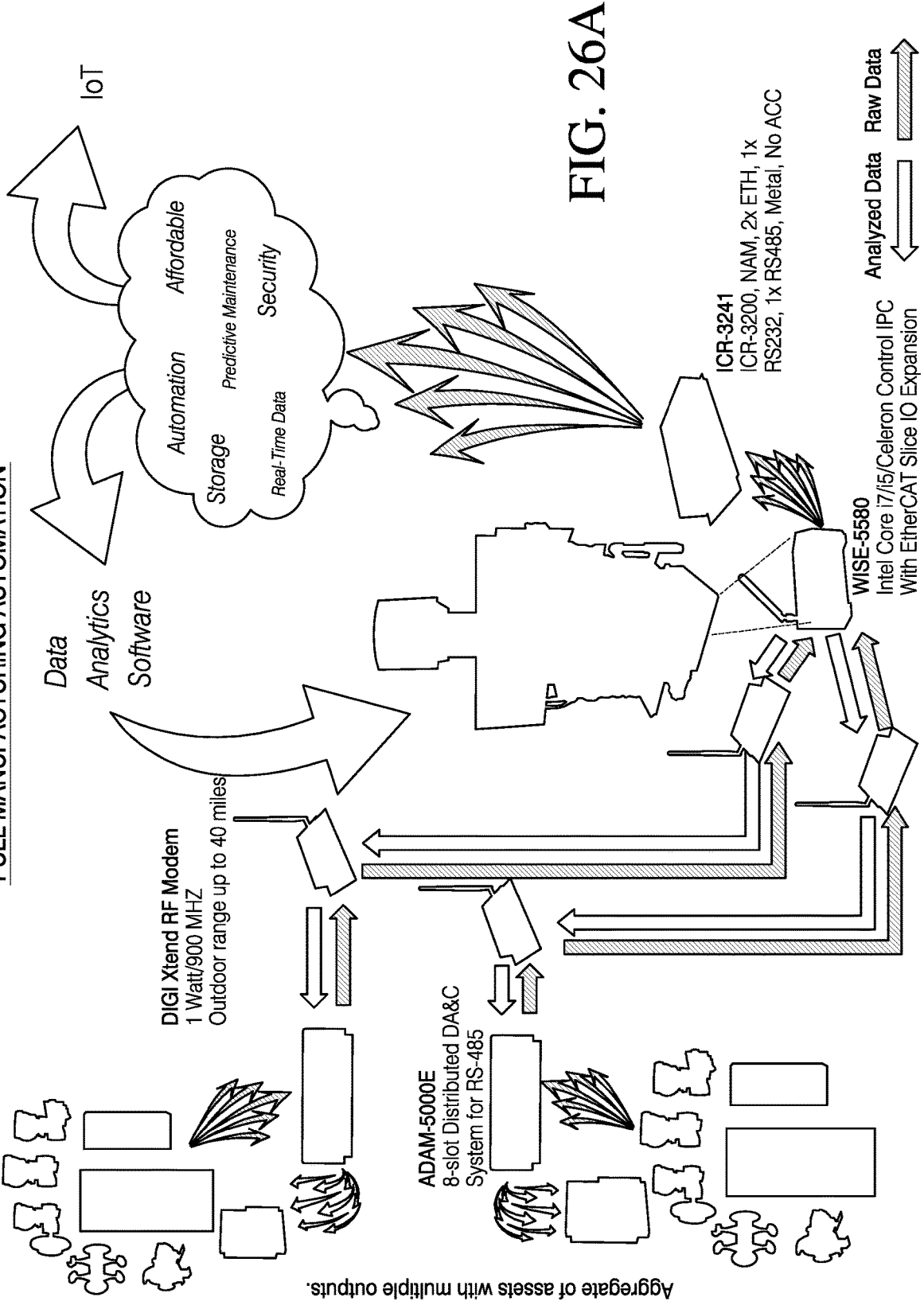

FLUID MONITORING SYSTEMS AND METHODS

CROSS REFERENCE TO RELATED APPLICATIONS

This nonprovisional patent application claims priority from provisional U.S. Pat. App. Nos. 63/056,355 filed on Jul. 24, 2020 and 62/958,418 filed on Jan. 8, 2020, both of which applications are incorporated by reference herein in their entireties.

FIELD OF THE INVENTION

The present disclosure related to apparatuses and methods for collecting and monitoring water samples, providing the ability for process manufacturing automation and optimization, and in one illustrative embodiment to an improved flow cell.

STATEMENT REGARDING FEDERALLY SPONSORED RESEARCH OR DEVELOPMENT

No federal funds were used to develop or create the invention disclosed and described in the patent application.

BACKGROUND

For thousands of years, civilizations throughout the world have been developing new ways to achieve a result more efficiently with each passing generation. In the late 1700s the world began to see a change that would forever transform the face of this planet, known as the Industrial Revolution. Originating in Great Britain, the use of machines (such as the newly invented steam engine) began being the preferred method over hand production approaches, catapulting society into our modern-day world. The technology for on-line chemical analysis dates back about 90 years. In the 1930s the first non-dispersive infrared (NDIR) photometers were developed at the Ludwigshafen Research Lab, known as the Ultra Rot Absorption Schreiber (URAS). The URAS trade name belongs to the original manufacturer, Hartmann & Braun, which is now a unit of ABB. In the 1960s the development of real-time digital computers, followed by the microelectronics revolution, and the large-scale integration microprocessor in the 1970s, allowed highly sophisticated analytical techniques for on-line analysis.

Industries throughout the world are now at a sprint to keep up with their competitor, due to the accessibility of technological advances that flood into their market. Industries such as drinking water, wastewater, microelectronics, pharmaceutical, power, pulp and paper, and many other industries within industrial production continuously feel the pressure to evolve. Some of these industries are very different from one another, but even though one industry may provide a product unrelated to the other, the successful operation of these facilities is heavily reliant on the continuous analysis of water quality parameters. Online analytical instruments (analyzers) are on-line devices that automatically and continuously monitor sample streams (consisting of liquids, solids, or gases), determining the chemical composition or physical properties of specific substances. Due to controlling multiple critical functions, industries integrate new analyzer technologies to optimize their manufacturing process by increasing efficiency, productivity, quality, and safety. Depending on the industry, some utilize online analytical instruments for guidance on production changes, as well as to meet any state and federal regulations that govern them, known as compliance. Online analytical instrumentation has become one of the most important components directly affecting operations.

In today's world, the collective knowledge on water analysis has built an empire for technological advances in water quality monitoring for all parameters within the water industry. The power, semi-conductor, municipal, and even the pulp and paper industries, all share a common factor, which is water. Without this element, these industries would cease to exist. The way it is utilized is what differentiates these industries from one another, all requiring the monitoring of certain water quality parameters, unique to them, for process control and/or safeguards to ensure safety.

Online analytical instrumentation provides these industries with the tools that are necessary to perform continuous monitoring of these water parameters that are unique to their specific needs, resulting in spending hundreds of thousands of dollars in analyzer equipment, to at best, be able to use for 10 years before replacing. Unfortunately, not all analyzers are created equal, nor are the manufacturers they arise from. Once an instrument purchase is made, the purchaser is invested financially, and now finds itself at the mercy of the manufacturer for the life of that product, relying on the various levels of support offered by the manufacturer. Unfortunately, the purchase is often unaware of a given instrument's flaws until after the purchase, when the purchaser is already committed. When an instrument design flaw comes to light, some manufacturer's response is to offer a new, "upgraded" version, abandoning the support on their original design. This takes a huge financial toll on all industries, but none more than the municipal industry. These facilities do not generate the large net revenues seen with the others and rely greatly on this equipment to protect public health, as well as process control.

Recently, there has been a growing concern of potential contaminates found within source water used by drinking water facilities. Due to catastrophic events taking place, such as the 2014 Elk River chemical spill that affected 300,000 residents in West Virginia, public awareness has heightened. As a result, source water monitoring and responsiveness has become an essential, if not mandatory, component to all drinking water facilities. There is mounting pressure on these facilities for compliance, which is enforced by their state's regulatory agencies. It is imperative for the various analyzers to work properly and consistently, as multiple personnel rely upon these instruments to effectively do their job, so public health is maintained. One analyzer, the source water monitoring panel ("SWMP"), stood out from the rest, causing a tremendous amount of frustration, additional work, increased risk, and money, upon multiple facilities throughout the US.

The SWMP is an instrument that is used as an early detection system for contaminants within surface water entering a water treatment plant for processing. Upon the system being used as a safeguard for early detection of contaminants, it is also used for process control within these facilities, aiding in treatment changes. This is achieved by receiving a sample of water from the water source, typically using a pump. The water enters the instrument's flow cell through an inlet, where it disperses evenly throughout the inner chamber, contacting an array of sensors, before exiting the flow cell through a drain. The flow cell is critical to the success of a multitude of analyzers used throughout all industries that utilize water as a component of their process. By assuring the inlet water entering the flow cell is continuously flowing at an adequate rate for sensor operation, as well as frequently being replenished (eliminating short-circuiting), the analyzer will function as intended. Placing sensors into an optimum environment, provided by the flow cell, sensors have a greater probability of functioning correctly, providing you with "good" data (e.g., accurate), that can be trusted and used for multiple aspects of operations.

Having the ability to continuously monitor specific application points greatly increases production quality, reliability, and safety. Industries that utilize this technology know that to obtain optimum performance from online analytical instruments, they require frequent attention from an analyzer support staff or maintenance crew. With the continuous increase in regulatory requirements and high-priority economic concerns (operator health and safety, emissions control, water quality, and energy conservation, etc.), the importance of analyzer reliability to normal operations is on the rise. Particularly with respect to regulatory and safety uses, the time logged as "out-of-limits" because of an analyzer being "off-line" can result in stiff fines, as well as pose a threat to employee safety and public health. In these situations, it is important to be able to deal with routine maintenance needs, as well as to recognize and characterize maintenance needs that require more specialized skills. Sourcing such specialized skills and having an expedited response to resolving an incident frequently become high-priority items within multiple industries. Nevertheless, facilities arriving at a viable solution is often not achieved due to the lack of available resources.

During the past 18 years or so, the full power of on-stream chemical analysis, combined with modern information technology, has taken hold throughout the process industry and is generating higher productivities, yields, efficiencies, and product quality. Once industries realized that obtaining these benefits using online analytical analyzers required work from highly skilled and experienced technical personnel, a culture evolved, dedicated to the maintenance and troubleshooting of these useful industrial analyzer tools. The question facing plant operations management is this: How do you realize the enormous potential benefits of online analytical analyzers without the overhead of online analytical analyzer specialists? Realizing these benefits required highly skilled and experienced technical personnel, the analyzer community evolved into a profession, focusing on the maintenance and troubleshooting of these useful industrial analyzer tools.

In the beginning, the computer was a highly specialized tool surrounded by a team of experts. During the late 1950s, the general population were not allowed to approach these computational machines. Society created an environment that conditioned the harboring of information, not allowing the consumer the capacity to fully perform required maintenance, or the ability to troubleshoot issues. This ideology is still utilized today by some manufacturing companies to further increase revenue. However, the consumer is in search for further control, with a turn-key solution. Ultimately, companies such as Microsoft and Intel realized what the consumer wanted and turned every consumer into a computer guru. Today's user needs to know very little about advanced programming, since the large software producers already have done it. Besides very few exceptions, consumers mostly rely on preprogrammed software tools that come with the operating system. By providing operators across multiple industries the ability to become an "analyzer guru", all end-users would possess the ability to modify or create their own custom programs. This degree of control would allow all operators to perform their job functions more effectively, increasing efficiency, safety, and quality, resulting in manufacturing facilities generating more revenue.

Furthermore, facilities within each industry are faced with operational issues that create limitations on which analyzers they can use, where they can be installed, and what features can be utilized. Due to multiple uncontrollable variables, there is no such thing as the perfect analyzer for every application. However, with the abundance of available technologies and software platforms, the process industry can very easily become one step closer to seeing a perfect analyzer. Online analytical instrumentation manufacturers are continuously developing new, more technologically advanced instruments; however, most end-users still do not have the visibility of data or control they need to drive innovations within the manufacturing process. Customers purchasing upgraded versions of their current model often remove fully functional instrumentation to obtain newer, more technologically advanced versions. These new features often present further operational control, allowing the consumer more freedom to mold the analyzer to meet as many needs as the consumer requires. Depending on which analyzer is being purchased, facilities within each of these industries often pay thousands of dollars for a single analyzer. More often, purchasing multiple units of the same model of analyzer is necessary, due to process or regulatory requirements. The amount invested can be substantial, easily surpassing $100,000.

Traditionally, automation systems have had a proprietary design because of the need for close-knit process structures that operate in real-time. This helped suppliers forge close partnerships with the end-user. The model also created vendor lock-ins that allowed manufacturers to source control systems from one supplier. This also eliminated the ability to implement state-of-the-art applications and technologies from other vendors. Unfortunately, in the long run, this inhibited a manufacturer's ability to innovate and harness technology for the betterment of its processes. The development of programmable logic controllers (PLCs) will play an important role in driving the industry's revolution into a new era. With greater programming flexibility and convenience, scalability, more memory, smaller form factor, high-speed (Gigabit) connectivity, and embedded wireless functionalities, future PLCs will adapt technology improvements in software, communications, and hardware. A key factor in the future of process analyzer technology will contain incorporating PLCs with programmable automation controllers (PACs). By merging PLCs programming flexibility with the PACs communication and control abilities, users will have a solid foundation to innovate any process. To accomplish this symbiotic relationship, controller manufacturers would need a PLC to control an application, and then provide the necessary tools to organize, analyze, and present process data to a user wherever and whenever needed. The final component to complete this technological powerhouse is cloud computing, which is at the forefront of data analytics. This technological trio creates a system with endless industrial process innovation capabilities.

The evolution of online analytical instrumentation has created a highly technologically advanced tool. Today, analyzer manufactures attempt to fulfill the end-user's request to simplify operations, create more automation to reduce operator involvement while taking corrective actions autonomously. This degree of operational control is rarely seen throughout the analytical instrumentation market. The availability of technology exists; however, applying that technology must come in the form of thinking outside of the box, rather than following in the footsteps of others. Throughout history, the same pattern of issues continues to surface, from a technological and operational perspective, decade after decade. The merging of technologies creates a path for manufacturers to take that next leap towards the fifth industrial revolution, where industrial automation systems will share resources and collaborate with one another. To revolutionize the industrial process industry, capitalizing off various technologies will accelerate innovation, creating an endless sea of potential.

Online analytical instrumentation (generally called process analyzers) may be also identified as online analytical instruments, or online analytical analyzers. This equipment is used for online chemical or physical analysis of process streams or plant environments. On-stream (online) analytical data refers to the collection of data for analysis or process control, obtained by a connection supplying a sample directly to a process analyzer. These streams are commonly continuous and pulled from precise points throughout the manufacturing process for multiple industries. This technology has proven to be vital for the safe and efficient operation in the municipal, petroleum, chemical, pharmaceutical, pulp and paper, power, as well as other industries within industrial production. Historically speaking, these instruments have been complex, even temperamental, systems with relatively unique operational and maintenance requirements. Consisting of multiple components, the flow cell (also referred to as a trough or sample cell) is one of those components that is critical for the success of the analyzer, but often an undervalued element to an online analytical analyzer's usefulness and effectiveness. Being a component found within many process analyzers throughout each industry, it is a prime candidate to facilitate the technical advancement within the analytical instrumentation industry. These come in a variety of shapes and sizes and are responsible for continuously supplying samples to be analyzed by an array of measurement technologies (e.g., sensors, photometers, etc.), each monitoring a specific chemical or physical parameter.

For online instrumentation to be continually used, it must be versatile, reliable, and trusted. To achieve this, an analyzer must provide all the necessary tools to perform its intended function, while being self-sufficient, and adaptable to meet the unique needs commonly found from one facility to the next.

The SWMP analyzer was a successful implementation and is a powerful tool; however, its factory design inhibits its usefulness and ability to adapt to multiple environments, as well as other deficiencies with it and the prior art in general without limitation. Various relevant prior art references include U.S. Pat. Nos. 4,626,992; 5,242,602; 5,315,880; 5,386,373; and 5,451,314 as well as U.S. Pat. Pub. No. 2014/0155867.

BRIEF SUMMARY OF THE INVENTION

An illustrative embodiment of a flow cell according to the present disclosure may include a main chamber, base plate, and cover. The main chamber may be formed with an interior portion having various angled surfaces so as to direct fluid positioned within the interior portion toward one or more drains via gravity.

The base plate may be engaged with the bottom surface of the main chamber. Sample fluid may flow into the main chamber via one or more inlet passages, which inlet passage(s) may be in fluid communication with an inlet header formed in the base plate. The flow of the sample fluid into and out of the flow cell may be adjusted to provide a specific residence time within the flow cell, during which one or more sensors may be in contact with the sample fluid.

Various aspects of the control and/or operation of the flow cell and/or various components thereof may be automated. A PLC and/or PAC may be in communication with various components of the flow cell and/or external components for monitoring, sensing, and/or providing other functionality.

BRIEF DESCRIPTION OF THE DRAWINGS

The accompanying drawings, which are incorporated in and constitute a part of this specification, illustrate embodiments and together with the description, serve to explain the principles of the methods and systems.

FIG. 9 is a perspective view of a portion of the flow cell showing a portion of the fluid conduit providing fluid to the second cleaning nozzle.

FIGS. 25A-25I provide various views of an illustrative embodiment of a flow cell highlighting a pathway for a wash fluid flow into, through, and out of the flow cell.

FIGS. 26A & 26B provide schematic views of illustrative embodiments of a communication overview that may be used with various illustrative embodiments of a flow cell.

DETAILED DESCRIPTION

Figure 1A:
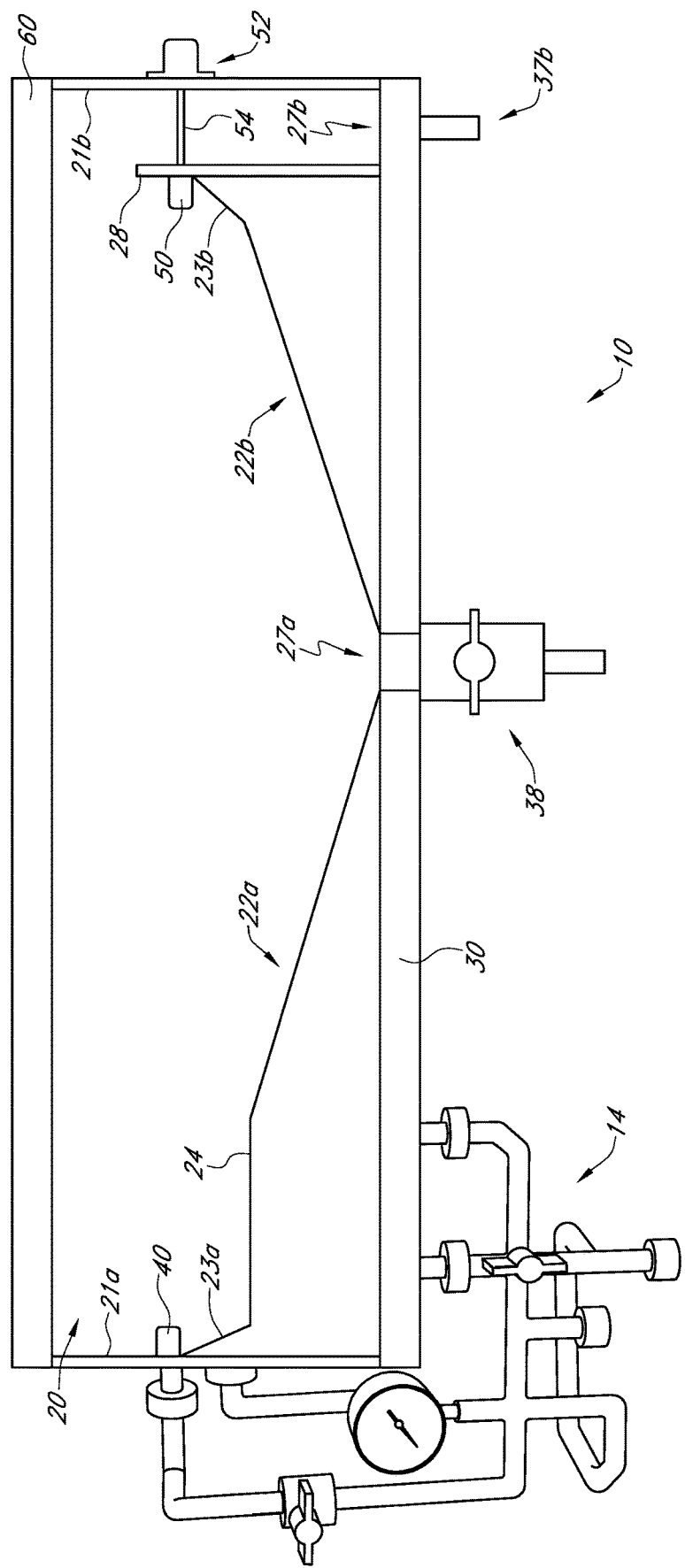
FIG. 1A is a cross-sectional side view of an illustrative embodiment of a flow cell with various interior portions shown.

Before the present methods and apparatuses are disclosed and described, it is to be understood that the methods and apparatuses are not limited to specific methods, specific components, or to particular implementations. It is also to be understood that the terminology used herein is for the purpose of describing particular embodiments/aspects only and is not intended to be limiting.

As used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

"Aspect" when referring to a method, apparatus, and/or component thereof does not mean that limitation, functionality, component etc. referred to as an aspect is required, but rather that it is one part of a particular illustrative disclosure and not limiting to the scope of the method, apparatus, and/or component thereof unless so indicated in the following claims.

Throughout the description and claims of this specification, the word "comprise" and variations of the word, such as "comprising" and "comprises," means "including but not limited to," and is not intended to exclude, for example, other components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and apparatuses.

These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and apparatuses. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The present methods and apparatuses may be understood more readily by reference to the following detailed description of preferred aspects and the examples included therein and to the Figures and their previous and following description. Corresponding terms may be used interchangeably when referring to generalities of configuration and/or corresponding components, aspects, features, functionality, methods and/or materials of construction, etc. those terms.

It is to be understood that the disclosure is not limited in its application to the details of construction and the arrangements of components set forth in the following description or illustrated in the drawings. The present disclosure is capable of other embodiments and of being practiced or of being carried out in various ways. Also, it is to be understood that phraseology and terminology used herein with reference to device or element orientation (such as, for example, terms like "front", "back", "up", "down", "top", "bottom", and the like) are only used to simplify description, and do not alone indicate or imply that the device or element referred to must have a particular orientation. In addition, terms such as "first", "second", and "third" are used herein and in the appended claims for purposes of description and are not intended to indicate or imply relative importance or significance.

Table of Elements

| Element Description | Element Number |
|---|---|
| Flow cell | 10 |
| Valve | 12 |
| Piping | 14 |
| Pressure gauge | 15 |
| Flow meter | 16 |
| Main chamber | 20 |
| First end wall | 21a |
| Second end wall | 21b |
| First ramp | 22a |
| Second ramp | 22b |
| First angled portion | 23a |
| Second angled portion | 23b |
| Slight decline portion | 24 |
| Front-interior wall angled portion | 25a |
| Back-interior wall angled portion | 25b |
| First inlet passage | 26a |
| Second inlet passage | 26b |
| Third inlet passage | 26c |
| Secondary drain | 27a |
| Primary drain | 27b |
| Weir | 28 |
| First mounting bracket | 29a |
| Second mounting bracket | 29b |
| Base plate | 30 |
| First base plate inlet | 32a |
| Second base plate inlet | 32b |
| Inlet header | 34 |
| Secondary drain passage | 37a |
| Primary drain passage | 37b |
| Secondary drain valve | 38 |
| First cleaning nozzle | 40 |
| Second cleaning nozzle | 50 |
| Second cleaning nozzle plate | 52 |
| Second cleaning nozzle fluid conduit | 54 |

Table of Elements -continued

| Element Description | Element Number |
|---|---|
| Pressurized sample inlet flushing mechanism | 55 |
| Cover | 60 |
| Mounting apparatus | 102 |
| Flow cell | 110 |
| Sample fluid inlet line | 111 |
| Valve | 112 |
| Control valve | 112a |
| Solenoid valve | 112b |
| Check valve | 112c |
| Sample fluid manifold | 113 |
| Wash fluid manifold | 113a |
| Piping | 114 |
| Pressure sensor | 115 |
| Flow switch | 116 |
| Flow meter | 116a |
| Wash fluid inlet | 117 |
| Transparent panel | 118 |
| Pressure booster pump | 119 |
| Main Chamber | 120 |
| Waste chamber | 120a |
| First end wall | 121a |
| Second end wall | 121b |
| First ramp | 122a |
| Second ramp | 122b |
| First angled portion | 123a |
| Second angled portion | 123b |
| Cleaning nozzle passage | 124 |
| Front-interior wall angled portion | 125a |
| Back-interior wall angled portion | 125b |
| Sample fluid inlet port | 126 |
| Receiver | 126a |
| Secondary drain | 127a |
| Primary drain | 127b |
| Vent passage | 127bb |
| Front wall | 128 |
| Fluid control guide | 128a |
| First mounting bracket | 129a |
| Second mounting bracket | 129b |
| Base plate | 130 |
| Mounting aperture | 131 |
| Base plate inlet | 132 |
| Main inlet | 133 |
| Main wash fluid inlet | 133a |
| Sample fluid channel | 134 |
| Waste reservoir | 135 |
| Base plate cleaning nozzle passage | 136 |
| Secondary drain passage | 137a |
| Primary drain passage | 137b |
| Secondary drain valve | 138 |
| First cleaning nozzle | 140 |
| Second cleaning nozzle | 150 |
| Second cleaning nozzle plate | 152 |
| Second cleaning nozzle fluid conduit | 154 |
| Pressurized sample inlet flushing mechanism | 155 |
| Cover | 160 |
| Cover mounting aperture | 161 |
| Sensor | 162 |
| Cap | 164 |
| Auxiliary sample system | 170 |
| Auxiliary sample pump | 172 |
| Auxiliary sample flow switch | 174 |
| Auxiliary sample control valve | 176 |
| Auxiliary sample inlet line | 178 |
| Auxiliary sample inlet port | 180 |
| Auxiliary sample feed line | 182 |
| Backup power supply | 184 |

Generally, various illustrative embodiments of fluid monitoring systems & methods disclosed herein may use a flow cell 10, 110 as disclosed herein that may allow a user to upgrade a current analyzer(s) instead of having to fully replace them, retaining some, if not all of the user's investment. Additionally, those illustrative embodiments may provide a single component that is adaptable and interchangeable amongst all or nearly all industries, incorporating the latest innovations in technology and automation, while allowing facilities to process, store, and send their data anywhere while using cutting edge technology in the field of data analytics. The illustrative embodiments of a flow cell 10, 110 disclosed herein may be configured to reduce the number of process control analyzers at a single by location by greater than half. The illustrative embodiments of fluid monitoring systems & methods disclosed herein provide a flow cell 10, 110 that may provide a universal, smart flow cell, capable of being applied to a wide array of applications within multiple industries. The flow cell 10, 110 may provide versatility, adaptability, connectivity, automation, process control and optimization, real-time data analytics, and various other advantages and/or benefits over the prior art without limitation unless otherwise indicated in the following claims.

The illustrative embodiments of fluid monitoring systems & methods disclosed herein may be universal and adaptable, containing the capacity to benefit every or nearly every industry, all while simultaneously saving the end-user money and time. These illustrative embodiments may provide more control, workplace and public safety, automation, versatility, cloud computing, connectivity, data analytics, and other features without limitation unless otherwise indicated in the following claims.

The illustrative embodiments may provide various features and benefits not currently provided by a process control analyzer and may be compatible and adaptable to most makes and models of process analyzers, allowing the consumer to utilize their preexisting instrumentation. The illustrative embodiments of fluid monitoring systems & methods may also provide at least automation, process connectivity, cloud computing, data analytics, storage, data/information security, and real-time process control without limitation unless otherwise indicated in the following claims. These illustrative embodiments may perform the function of at least three process control analyzers, thus reducing onsite instrumentation, capital expenditure, and annual operational and maintenance (O & M) costs. The illustrative embodiments of fluid monitoring systems & methods may provide a foundation for unlimited potential, allowing site-specific customization in ways not previously possible, and may be engineered to withstand the harshest environments. Additionally, when configured accordingly, the illustrative embodiments disclosed herein may provide the ability to bring Industry 4.0 into any process manufacturing facility completely wire free.

It is contemplated that the illustrative embodiments of fluid monitoring systems & methods disclosed herein and the associated flow cells 10, 110 may be useful across a wide spectrum of applications in various markets including but not limited to drinking water, maritime, wastewater, industrial wastewater, pulp and paper, power, swimming pools, pharmaceutical, fracturing, food and beverage, plating offshore, chemical manufacturing, and manufacturing without limitation unless otherwise indicated in the following claims.

Figure 1B:
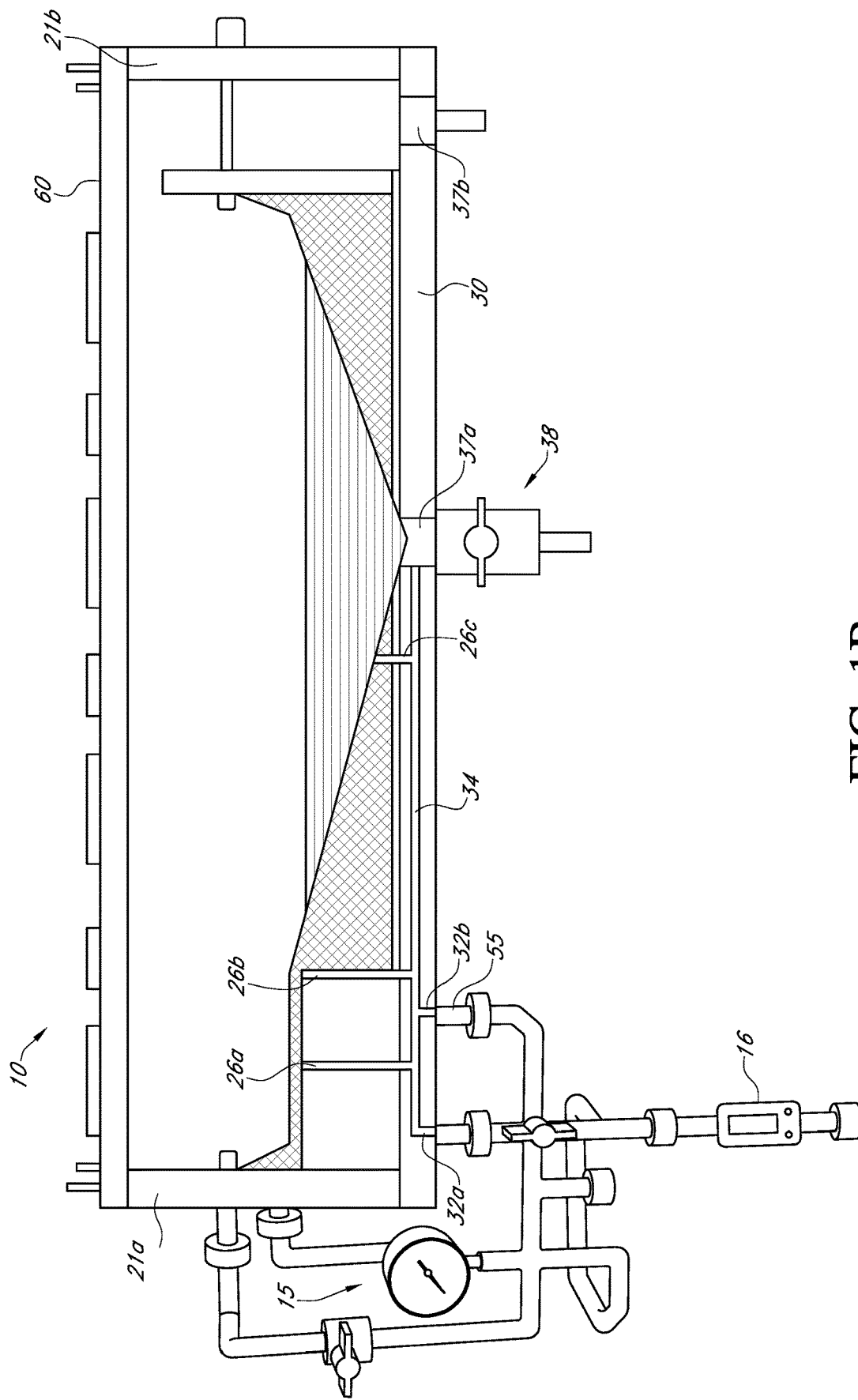
FIG. 1B is a cross-sectional side view of another illustrative embodiment of a flow cell with various interior portions shown and certain piping portions removed for clarity.

Referring now to the drawings, wherein like reference numerals designate identical or corresponding parts throughout the several views, FIGS. 1A & 1B provide two cross-sectional side views of an illustrative embodiment of a flow cell 10 that may be used with the various fluid monitoring systems and methods as disclosed herein. Certain details of various internal portions of the flow cell are shown in FIG. 1B that are not shown in FIG. 1A for purposes of clarity. Generally, it is contemplated that the illustrative embodiments of fluid monitoring systems and methods disclosed herein may be especially useful for use with a fluid comprised of water, but the scope of the present disclosure is not so limited unless otherwise indicated in the following claims.

Figure 14A:
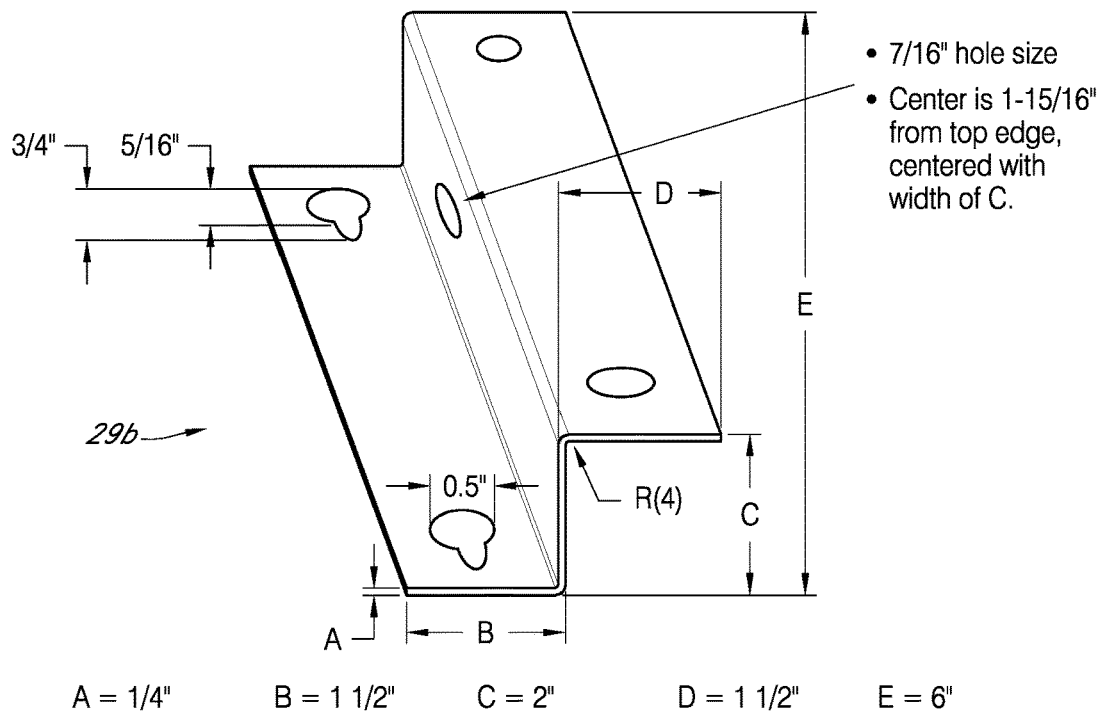
FIG. 14A provides a perspective view of an illustrative embodiment of a second mounting bracket.
Figure 14B:
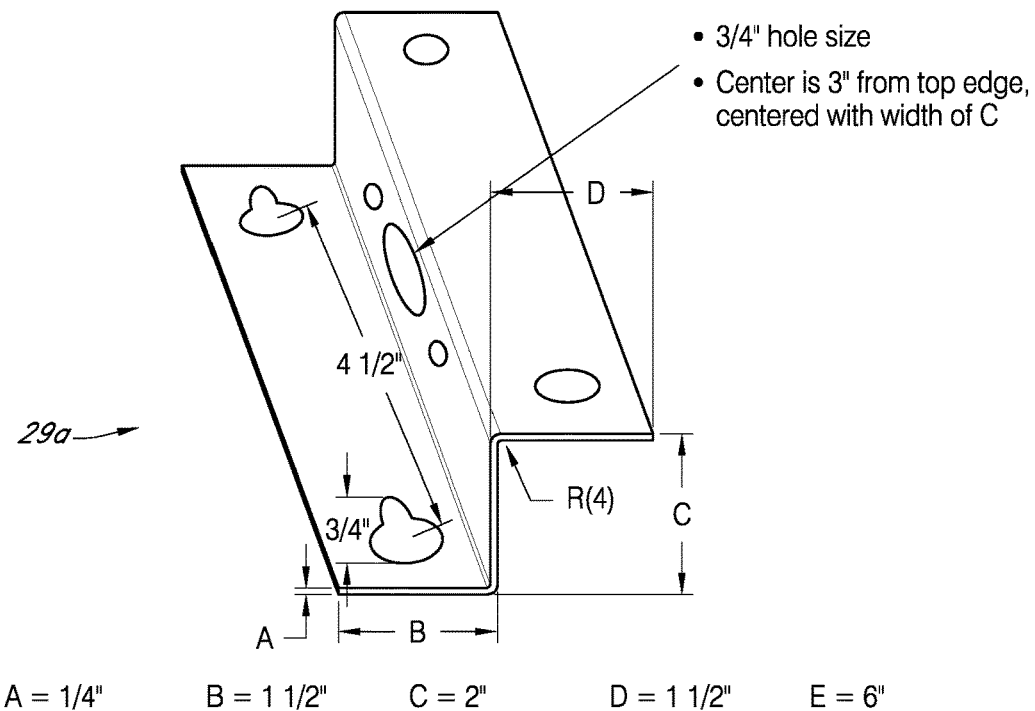
FIG. 14B provides a perspective view of an illustrative embodiment of a first mounting bracket.

Generally, an illustrative embodiment of a flow cell 10 may be comprised of a main chamber 20, which may be engaged with a cover 60 adjacent a top surface of the main chamber 20 and which may be engaged with a base plate 30 adjacent a bottom surface of the main chamber 20. Additionally, piping 14 and various associated fittings, valves 12, pressure gauge(s) 15, flow meter(s) 16, drains 27a, 27b, drain valve(s) 38, sensors, and/or associated fluid conduit may be engaged with various elements of the flow cell 10 without limitation unless otherwise indicated in the following claims. The flow cell 10 may be engaged with a structural support (e.g., wall, beam, stud, etc.) via a first mounting bracket 29a adjacent a first end wall 21a of the main chamber 20 and a second mounting bracket 29b adjacent a second end wall 21b of the main chamber 20. Illustrative embodiments of the mounting brackets 29a, 29b are shown in FIGS. 14A & 14B, which also provide illustrative dimensions of various features thereof without limitation unless otherwise indicated in the following claims. It is contemplated that the illustrative embodiments of the mounting brackets 29a, 29b may facilitate mounting the flow cell 10 such that the base plate 30 is generally parallel with respect to the ground surface and the end walls 21, 21b are generally vertically oriented, thereby maximizing the available volume within the main chamber 20 for sample fluid. Such volume maximization may contribute to the ability of the illustrative embodiment of the flow cell 10 to accommodate much higher sample fluid flow rates compared to the flow rates possible in the prior art (as described in further detail below) without limitation unless otherwise indicated in the following claims.

It is contemplated that for most applications it may be advantageous to engage one or more sensors with the cover 60, wherein the sensors are in proximity to and/or in contact with a flow of sample fluid positioned within the interior portion of the main chamber 20 without limitation unless otherwise indicated in the following claims. Various views of one illustrative embodiment of a cover 60 are shown in FIG. 9. Further, it is contemplated that for most applications the sample fluid may generally flow through an interior portion of the main chamber 20 in a direction from left to right in the orientation shown in FIGS. 1A-1D without limitation unless otherwise indicated in the following claims.

Figure 1C:
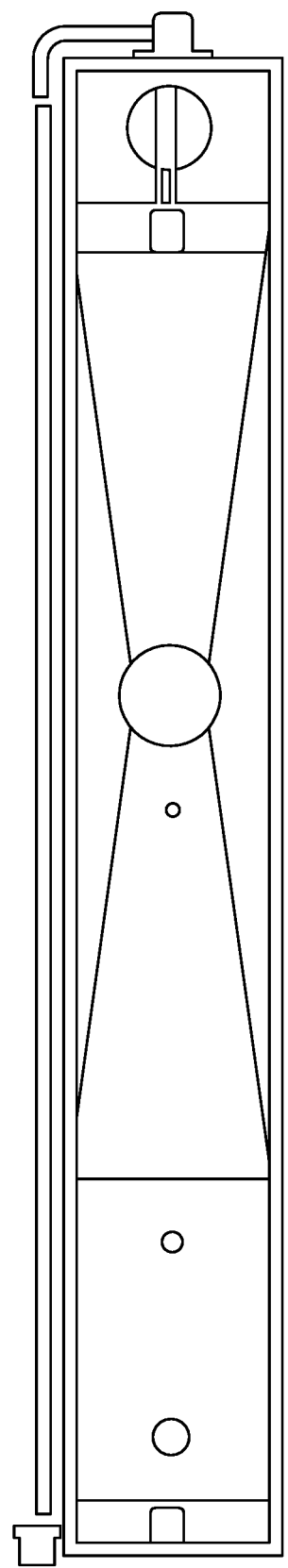
FIG. 1C is a top view of the flow cell shown in FIG. 1A.
Figure 1D:
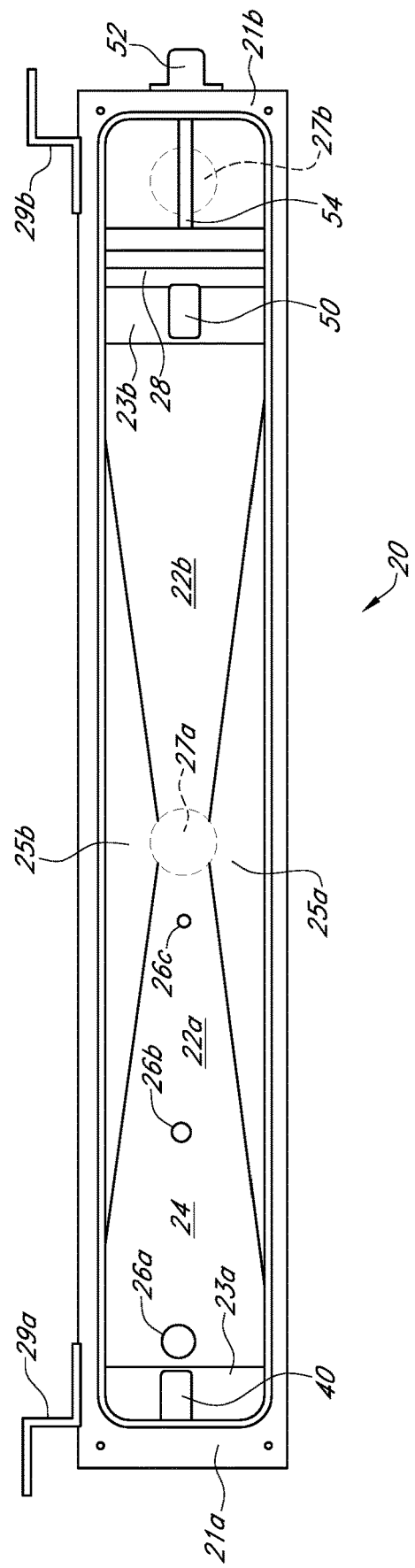
FIG. 1D is a top view of the flow cell shown in FIG. 1B.
Figure 2A:
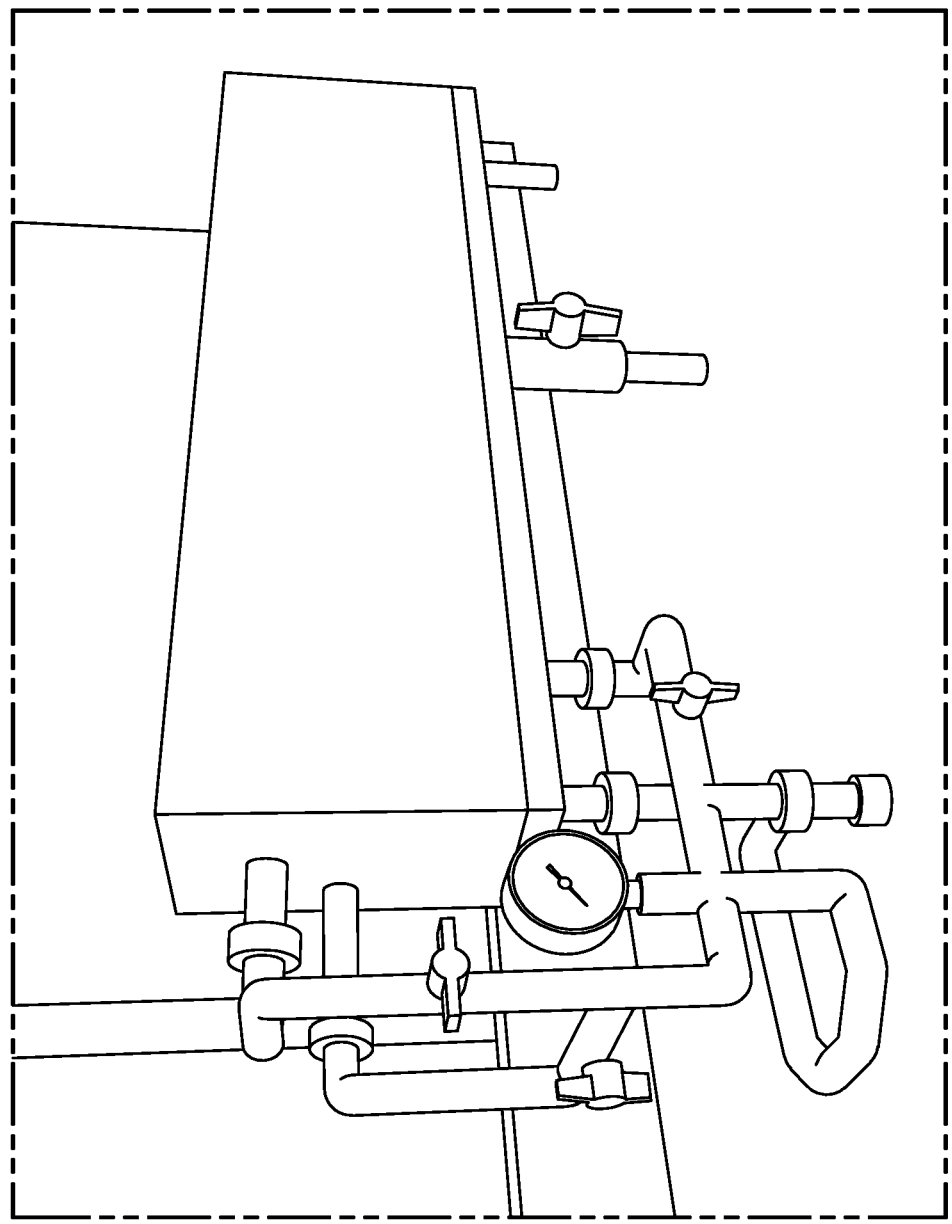
FIG. 2A is a perspective view of an illustrative embodiment of a flow cell.
Figure 2B:
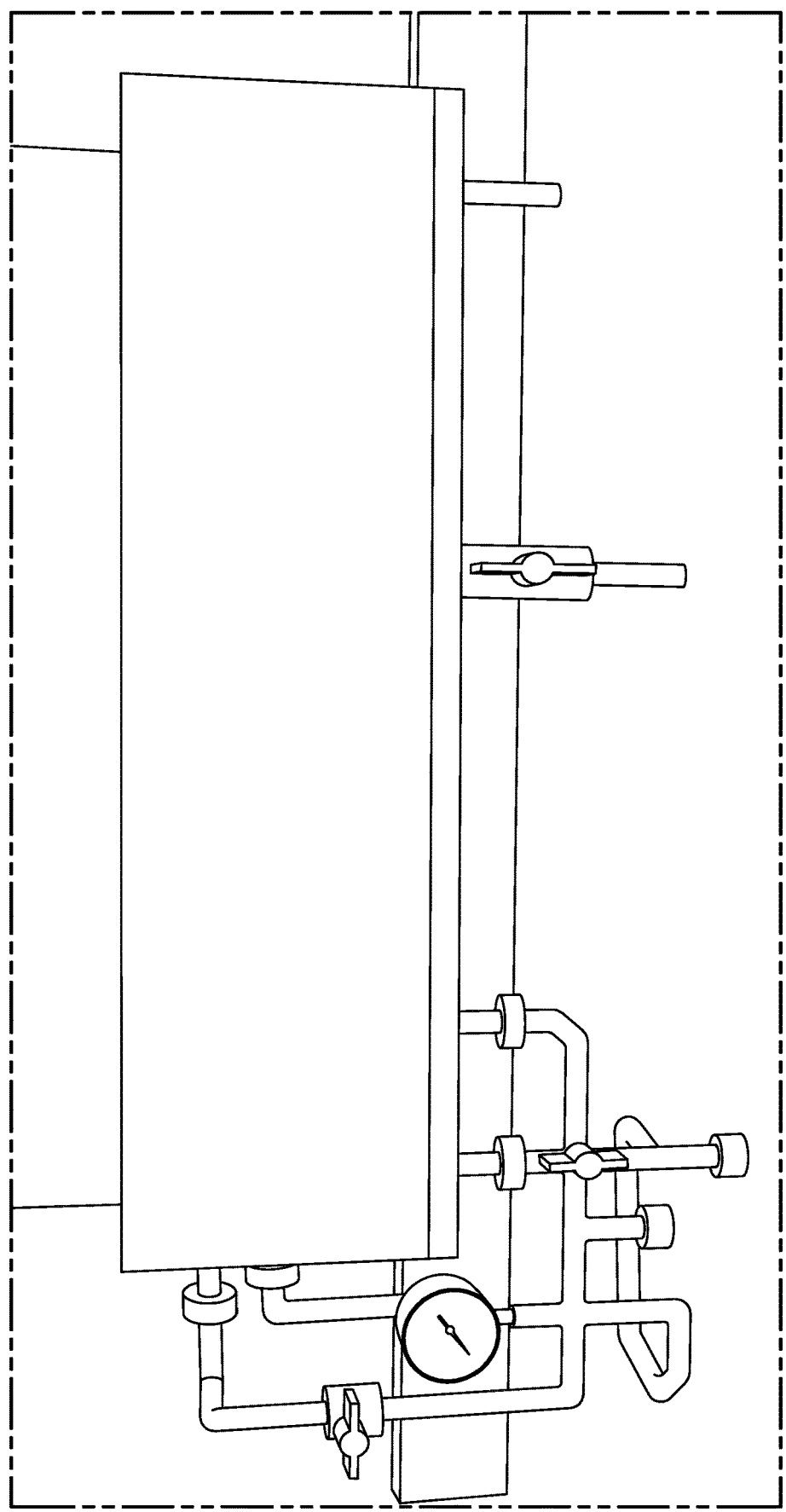
FIG. 2B is a front view of the illustrative embodiment of a flow cell shown in FIG. 2A.
Figure 3A:
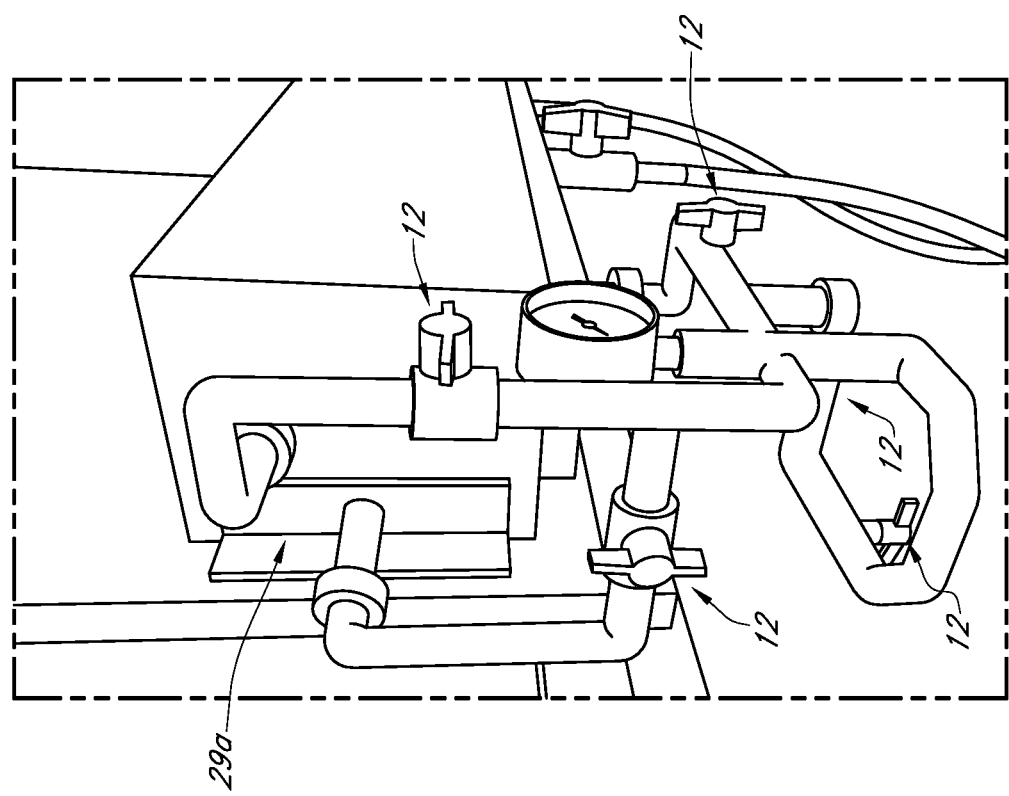
FIG. 3A is a detailed perspective view of a portion of the flow cell shown in FIGS. 2A & 2B.
Figure 3B:
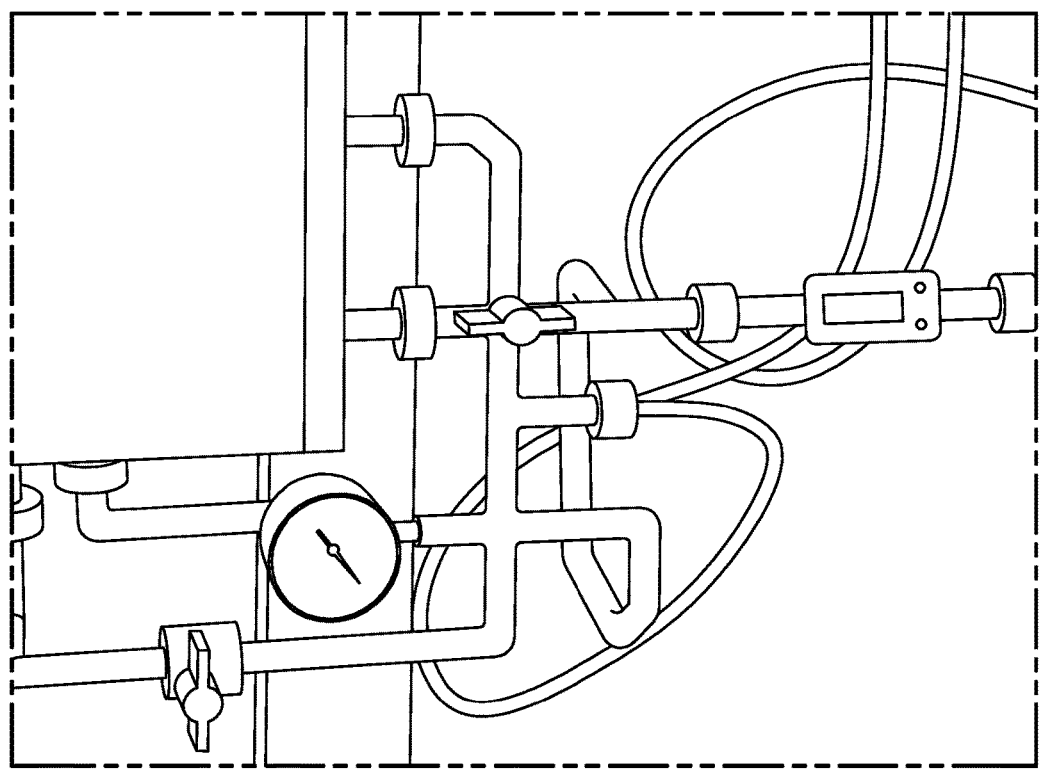
FIG. 3B is a detailed front view of the portion of the flow cell shown in FIG. 3A.
Figure 3C:
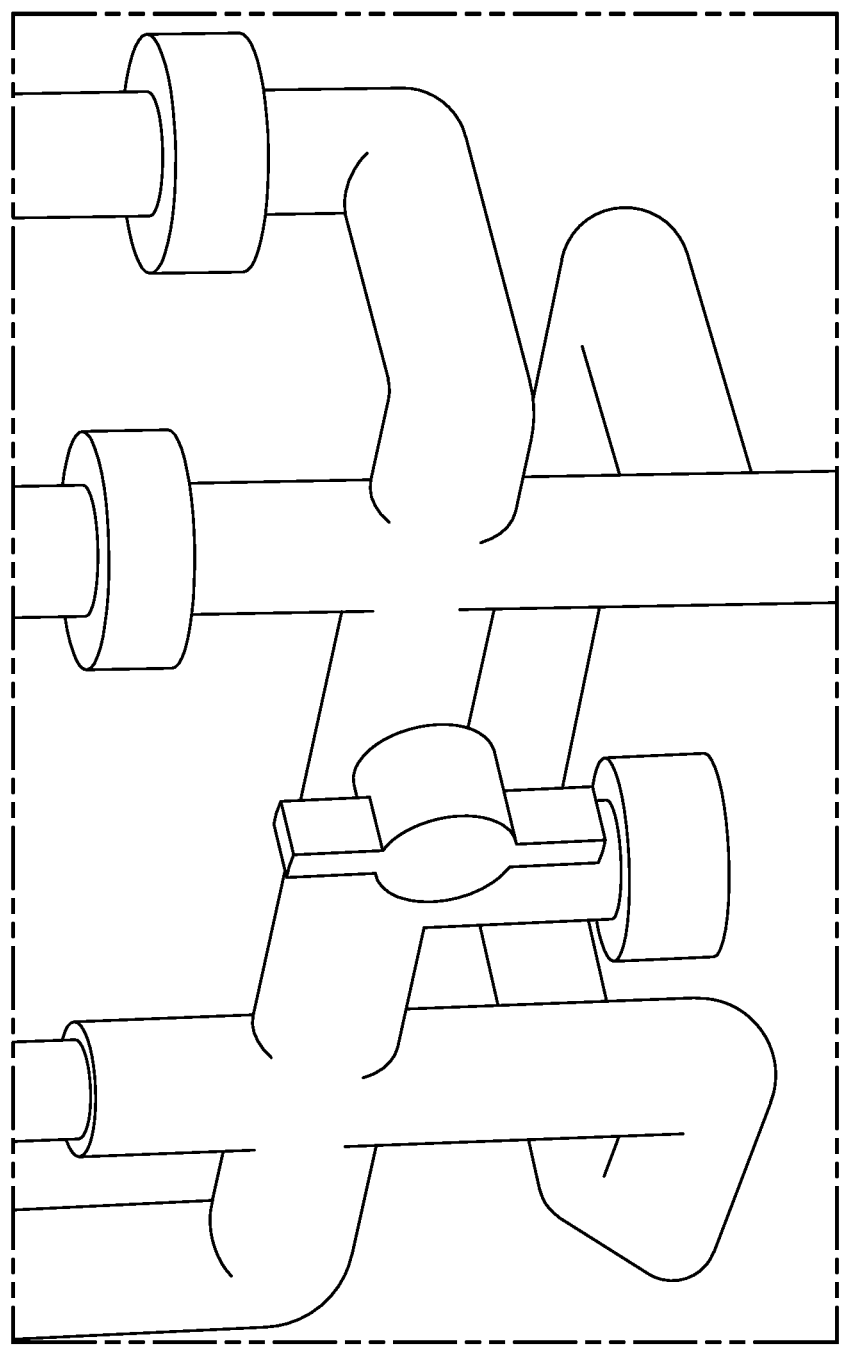
FIG. 3C is a detailed perspective view of a portion of the piping for the flow cell shown in FIGS. 3A & 3B.
Figure 3D:
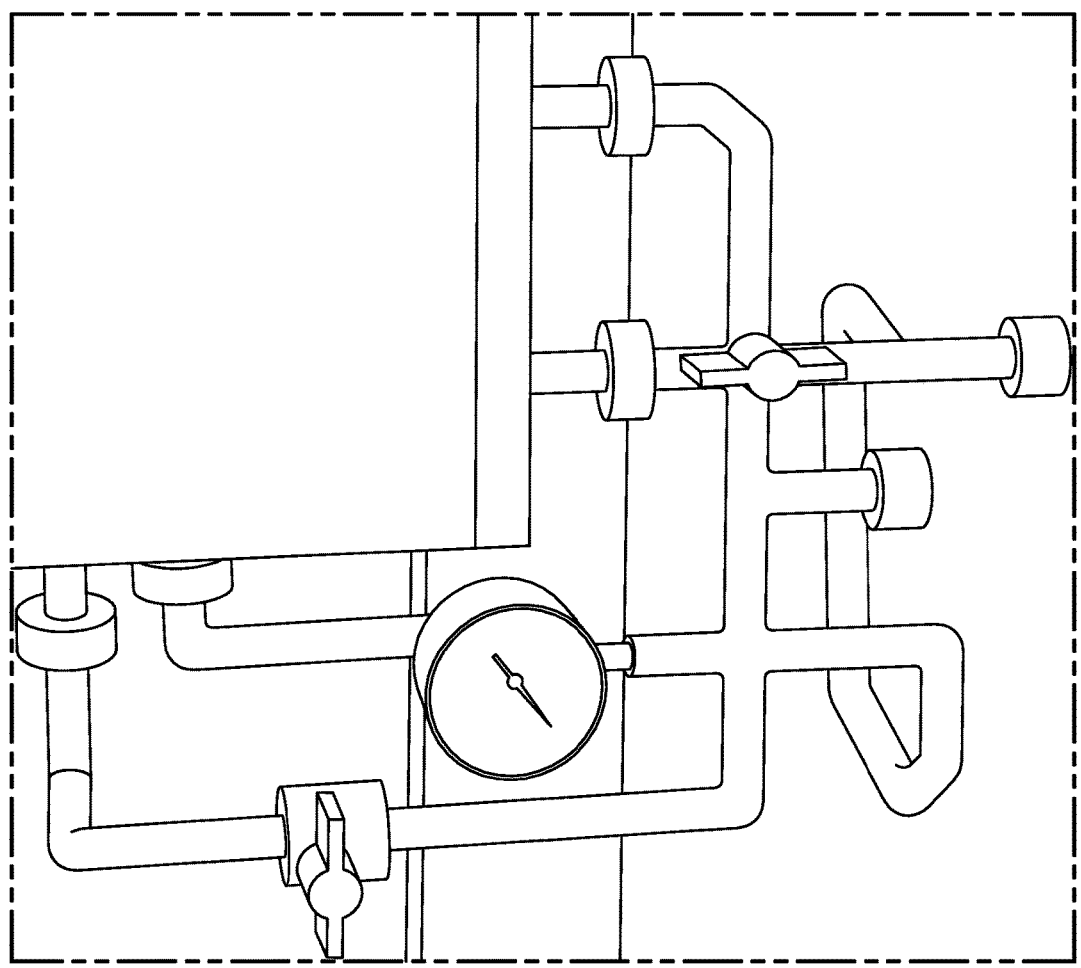
FIG. 3D is another detailed front view of the portion of the flow cell shown in FIGS. 3A & 3B.
Figure 3E:
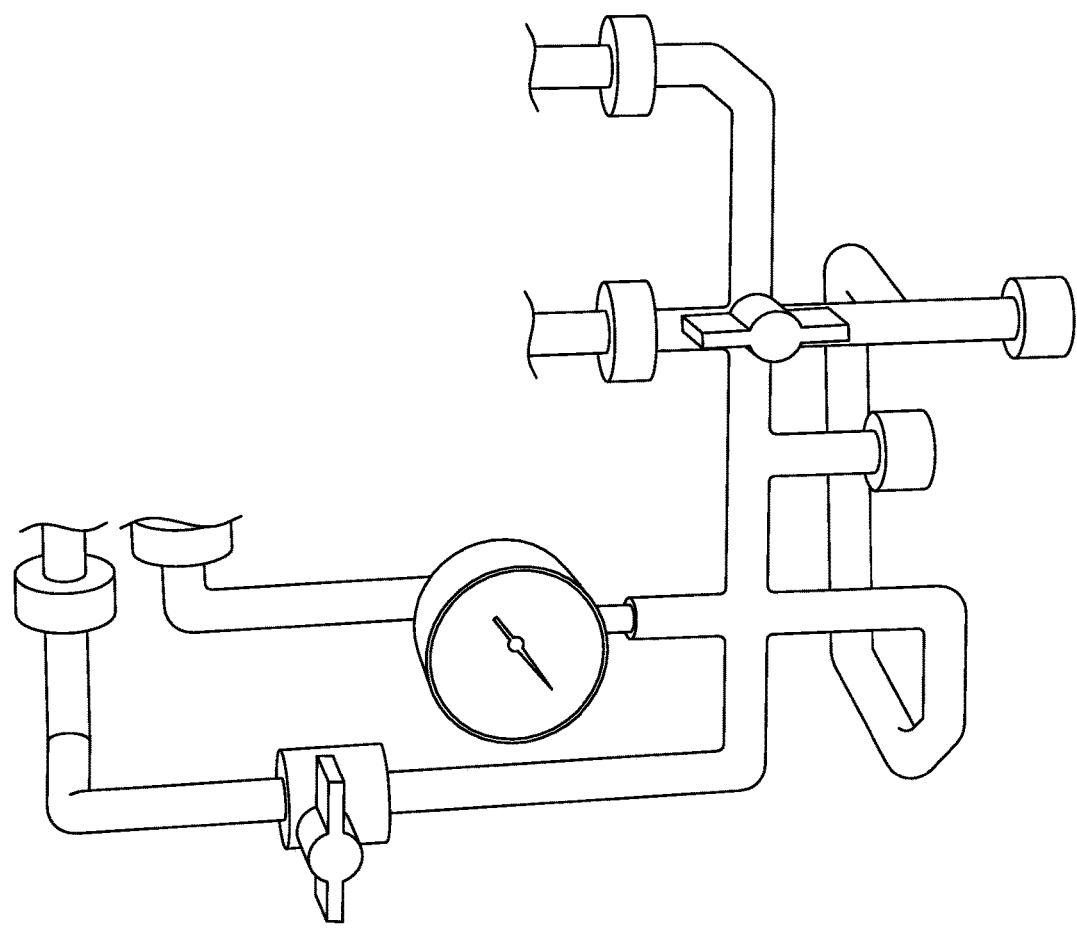
FIG. 3E is a detailed front view of the portion of the flow cell shown in FIGS. 3A & 3B with various structures removed for clarity.

Referring specifically to FIGS. 1A, 1B, & 1D (which provides a top view of the interior portion of the main chamber 20), the main chamber 20 may be formed with an interior portion having a first angled portion 23a leading to a slight decline portion 24, leading to a first ramp 22a, leading to a secondary drain 27a when moving in a direction from left to center in the orientation shown in FIGS. 1A & 1B. The interior portion of the main chamber 20 may also be formed with a second angled portion 23b leading to a second ramp 22b leading to the secondary drain 27a when moving in a direction from right to center in the orientation shown in FIGS. 1A & 1B. A weir 28 may be positioned on the right side of the main chamber 20 adjacent a second end wall 21b on the right side of the main chamber 20. The weir 28 and second end wall 21b may be spaced from one another to create a cavity therebetween, and a primary drain 27b may be formed in the bottom surface of the cavity between the weir 28 and second end wall 21b.

The main chamber 20 may be configured with a front-interior wall angled portion 25a and a back-interior wall angled portion 25b, as shown at least in FIGS. 1C & 1D and 13A & 13B. It is contemplated that the relative size, shape, and/or angle (with respect to other components of the flow cell 10) of the front-interior wall angled portion 25a and/or back-interior wall angled portion 25b may be critical in ensuring that the flow cell 10 operates correctly. Specifically, the configuration of the front-interior wall angled portion 25a and/or back-interior wall angled portion 25b may be critical in ensuring that all sediment, debris, etc. is directed toward the secondary drain 27a during use and/or when the first cleaning nozzle 40 and/or second cleaning nozzle 50 is used to flush/clean the interior portion of the main chamber 20. In the illustrative embodiment of a main chamber 20, the front-interior wall angled portion 25a may be configured utilizing an acute angle with a 45° slope, slanted down and back towards the secondary drain 27a, and the back-interior wall angled portion 25b may be configured utilizing an obtuse angle with a 135° slope, slanting down and forward towards the secondary drain 27a. In such a configuration, front-interior wall angled portion 25a and back-interior wall angled portion 25b may be symmetrical about a vertical plane bisecting the secondary drain 27a. Additionally, the top edge of both the front-interior wall angled portion 25a and back-interior wall angled portion 25b may intersect both the first ramp 22a and second ramp 22b at a point that is more than halfway above the elevation of the secondary drain 27a along the length of the first and second ramps 22a, 22b. However, the front-interior wall angled portion 25a and/or back-interior wall angled portion 25b may have other configurations, dimensions, angles, orientations, etc. without limitation unless otherwise indicated in the following claims. Other views of various portions of illustrative embodiments of the interior portion of a main chamber 20 are shown in FIGS. 7A, 7B, 10A-10C, and 13A-13B.

A first cleaning nozzle 40 may be positioned on a first end wall 21a of the main chamber 20 above the first angled portion 23a, which is positioned on the left side of the drawing in FIGS. 1A, 1B, and 1D. A corresponding second cleaning nozzle 50 may be positioned on a weir 28, which weir 28 may be positioned adjacent to but spaced from a second end wall 21b of the main chamber 20. The second cleaning nozzle 50 may be positioned above the second angled portion 23b (which is positioned generally on the right side of the drawing in both FIGS. 1A, 1B, and 1D). Additional information and details regarding one illustrative embodiment of a first and second nozzle 40, 50 are provided below, which first and second spray nozzle are manufactured by BETE and available at www.BETE.com. The cleaning nozzles 40, 50 may be configured as model FF extra wide-angle nozzles, which may have a generally fan-shaped spray pattern and may feature a one-piece construction. The illustrative embodiments of cleaning nozzles 40, 50 may be configured with a threaded male connection of a specific size, but any suitable connection structure and/or method may be used for the cleaning nozzles 40, 50 without limitation unless otherwise indicated in the following claims.

The spray characteristics may be configured with a 145-degree spray angle having medium impact spray, wherein the spray discharge may be deflected at 75 degrees from the inlet axis. The cleaning nozzles 40, 50 may be constructed of any suitable material, including but not limited to plastic, brass, other metal and their alloys and/or combinations thereof without limitation unless otherwise indicated in the following claims. The cleaning nozzles 40, 50 may be specified with a specific spray angle, spray pattern, and flow rate (at a given pressure), and the optimal configuration of the cleaning nozzles 40, 50 will vary from one application to the next, and is therefor in no way limiting to the scope of the present disclosure unless otherwise indicated in the following claims. Through testing it has been found that for some applications it may be advantageous to configure the cleaning nozzles 40, 50 with a flat fan spray pattern with a spray angle of 145 degrees without limitation unless otherwise indicated in the following claims.

Figure 11A:
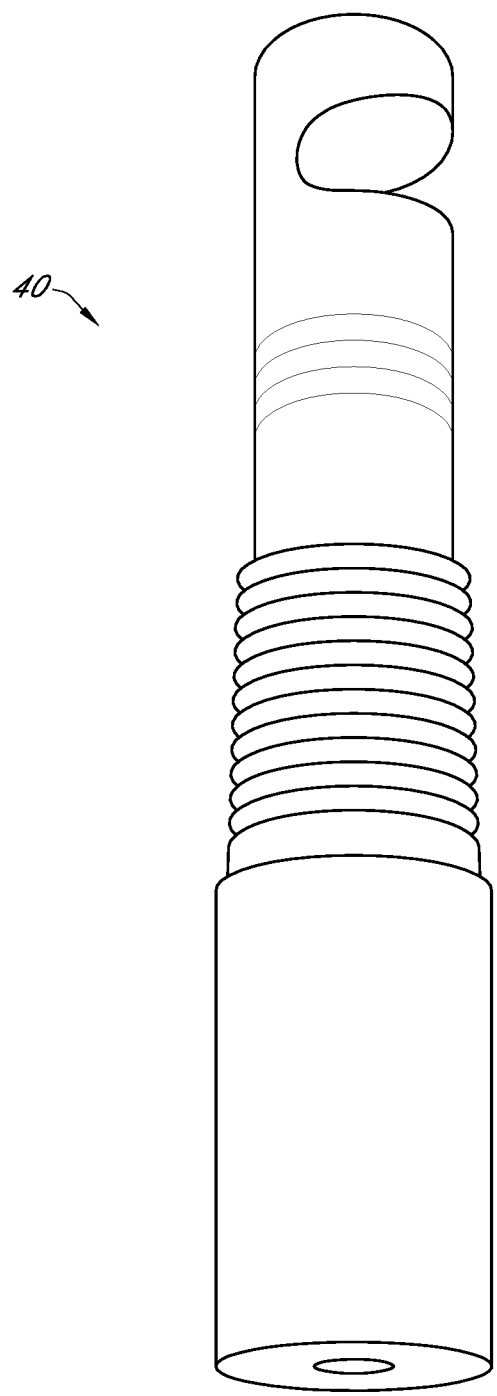
FIGS. 11A-11C provide various views of another illustrative embodiment of a first cleaning nozzle.
Figure 11B:
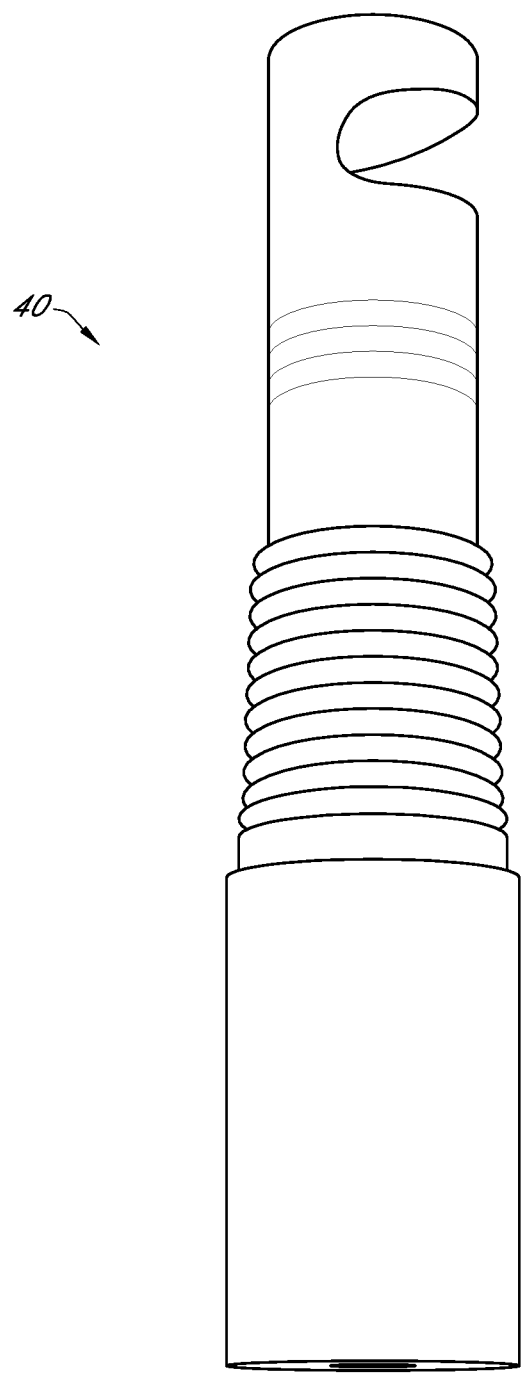
Figure 11C:
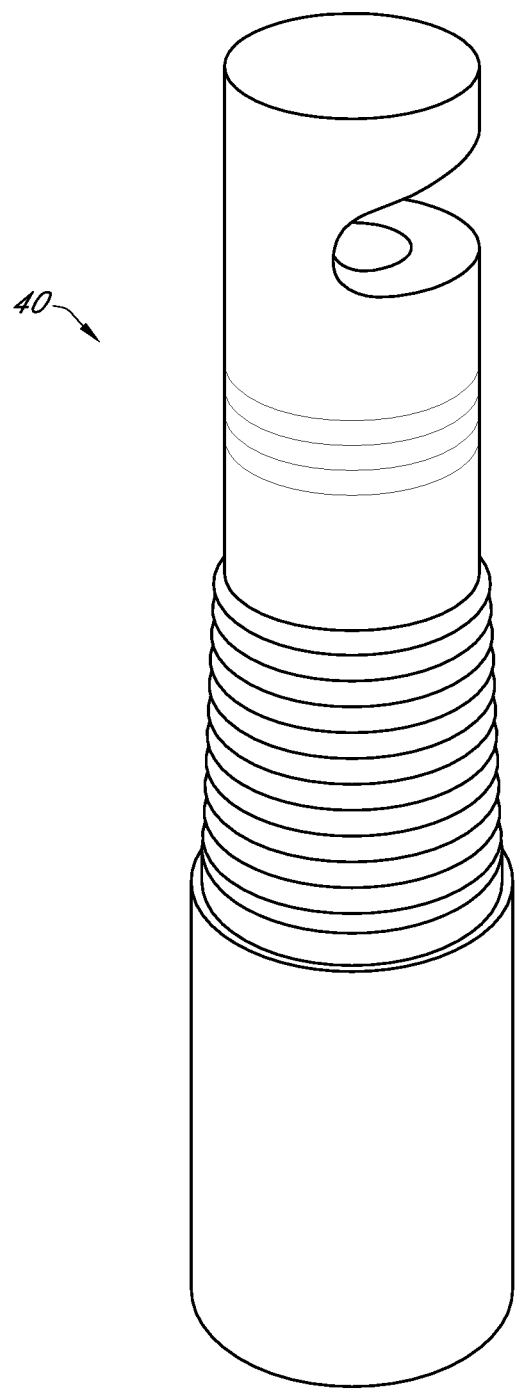

Another illustrative embodiment of a first cleaning nozzle 40 (which may be configured with an outlet port and from materials as described above) is shown in FIGS. 11A-11C. It is contemplated that the installation procedure for the embodiment of a first cleaning nozzle 40 shown in FIGS. 11A-11C as part of a retrofit kit (as described in further detail below) may be greatly simplified, which may impart a reduction in time required for the installation as well as eliminate/mitigate various potential mistakes during installation without limitation unless otherwise indicated in the following claims.

Figure 7A:
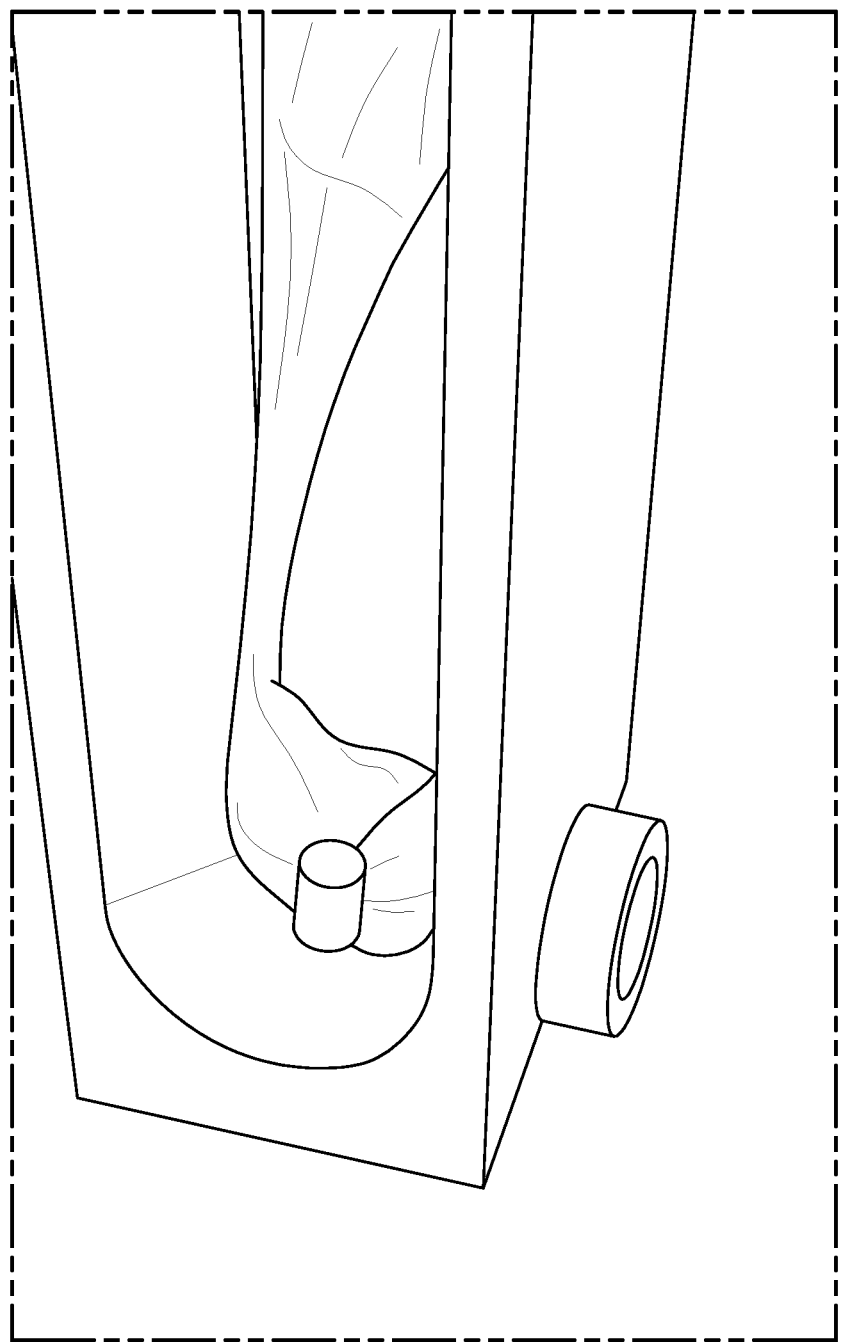
FIG. 7A is a detailed perspective view of a portion of the flow cell adjacent a first cleaning nozzle.
Figure 7B:
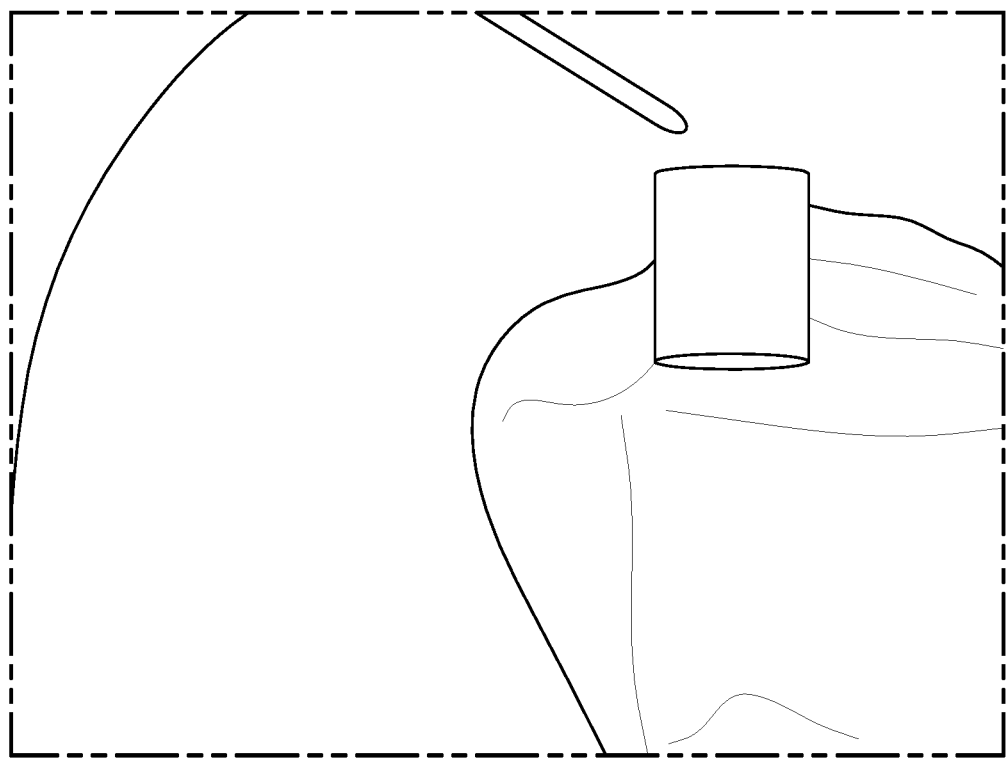
FIG. 7B is a detailed perspective view of a portion of the flow cell adjacent a second cleaning nozzle.
Figure 7C:
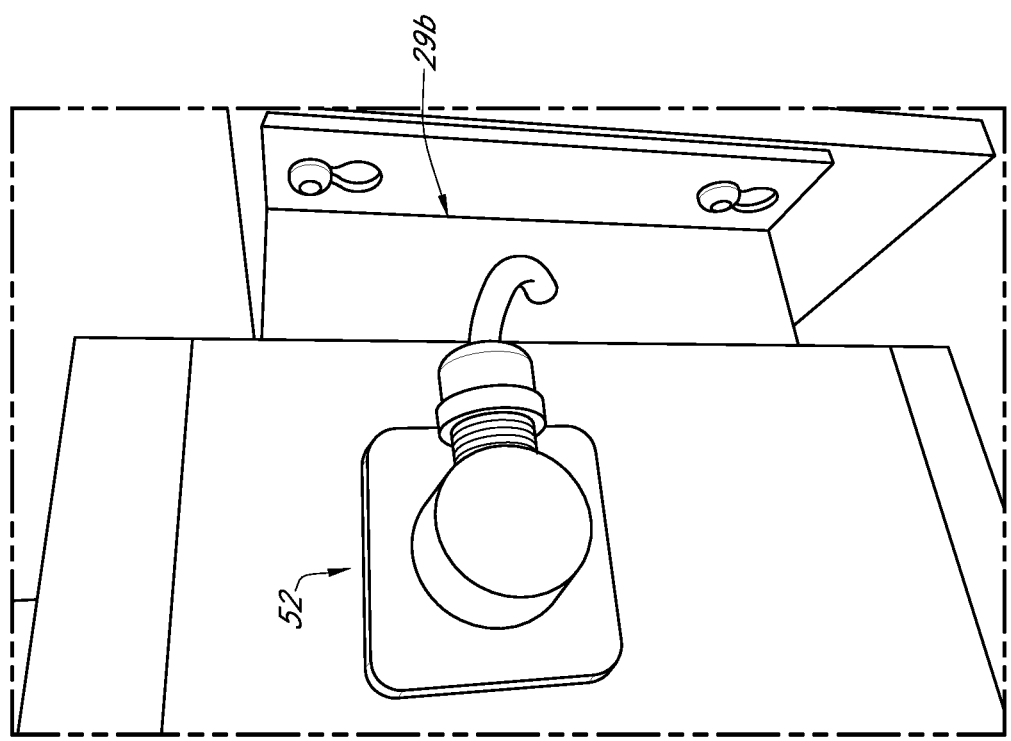
FIG. 7C is a detailed view of an exterior of the flow cell adjacent the second cleaning nozzle.
Figure 7D:
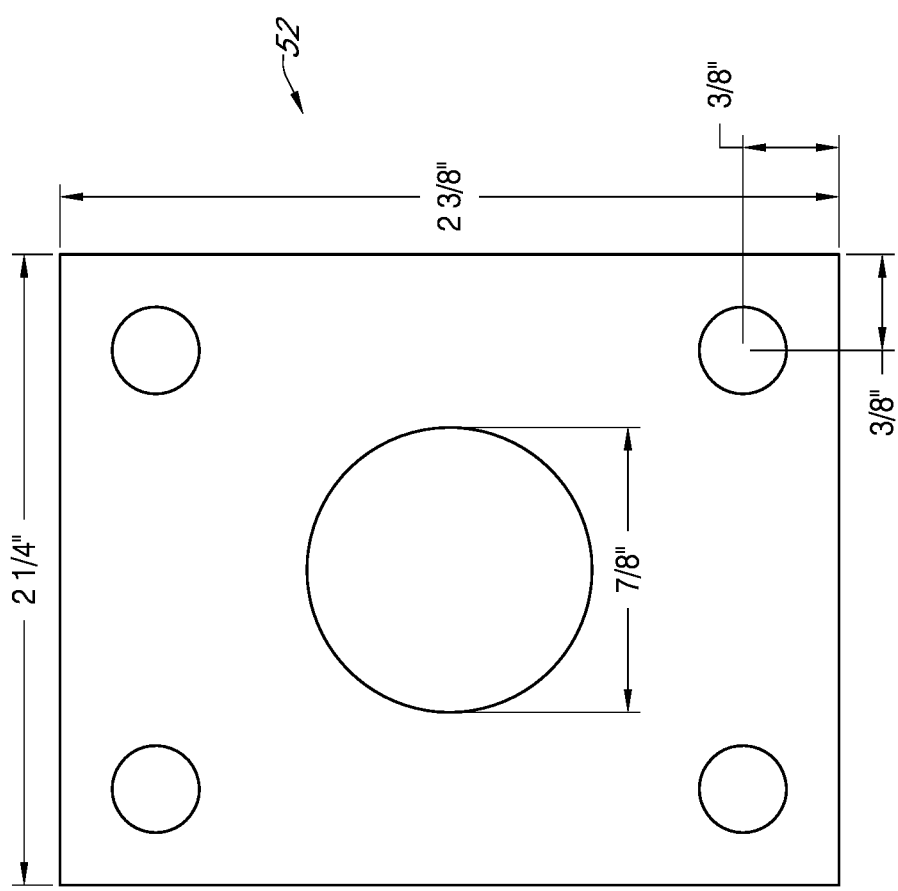
FIG. 7D is a front view of an illustrative embodiment of a cleaning nozzle plate that may be used with various embodiments of a flow cell.
Figure 7E:
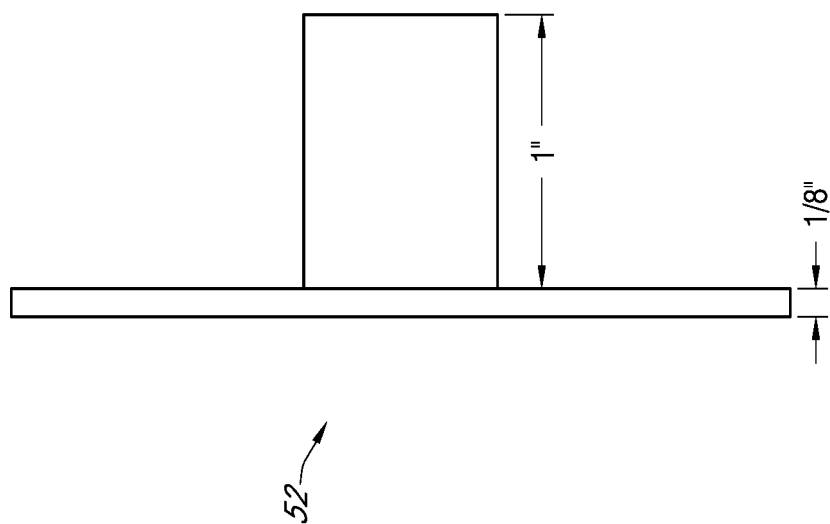
FIG. 7E is a side view of the illustrative embodiment of a cleaning nozzle plate shown in FIG. 7D.
Figure 8:
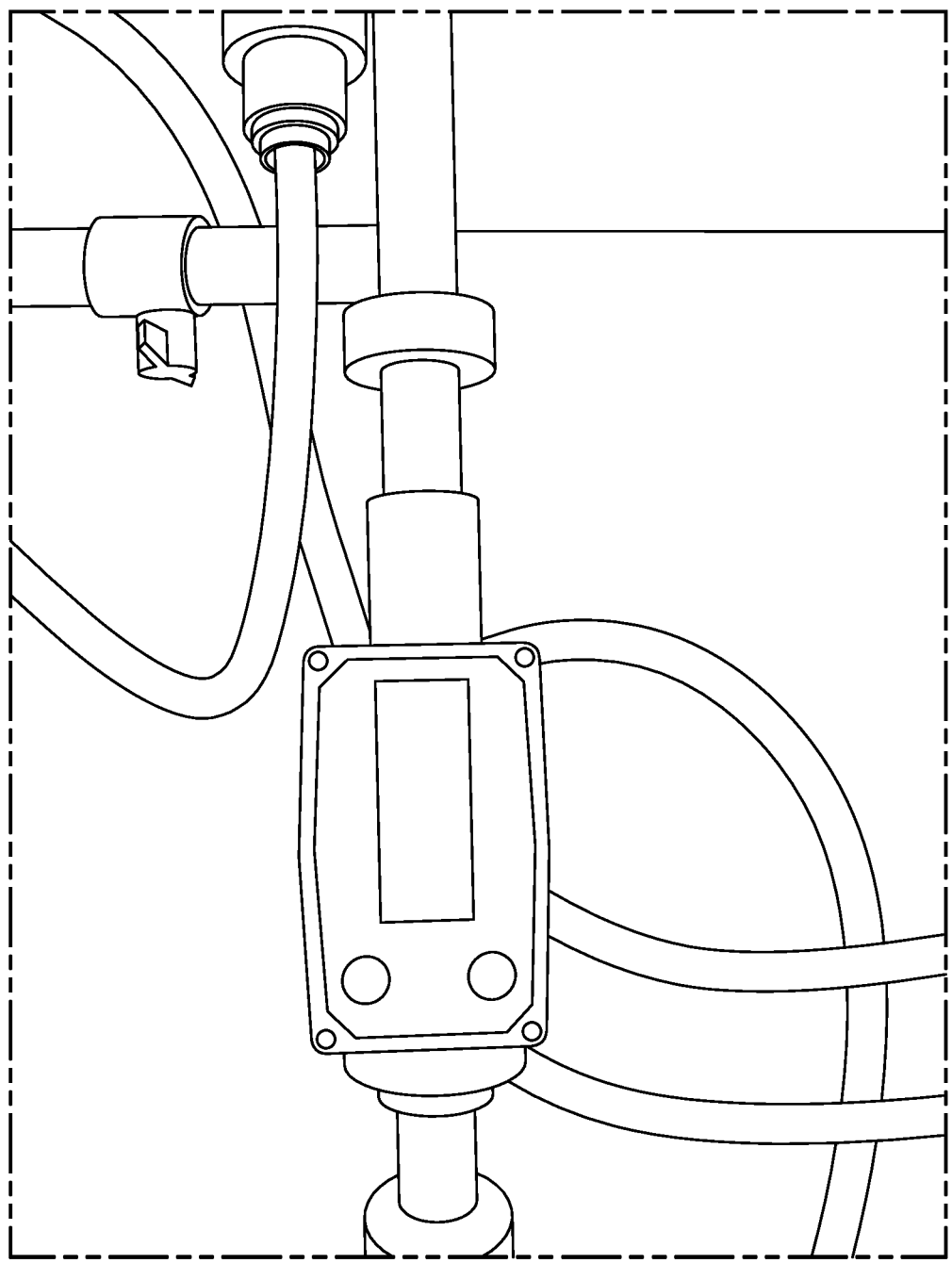
FIG. 8 is a detailed view of a portion of the flow cell adjacent a volumetric flow gauge.
Figure 10A:
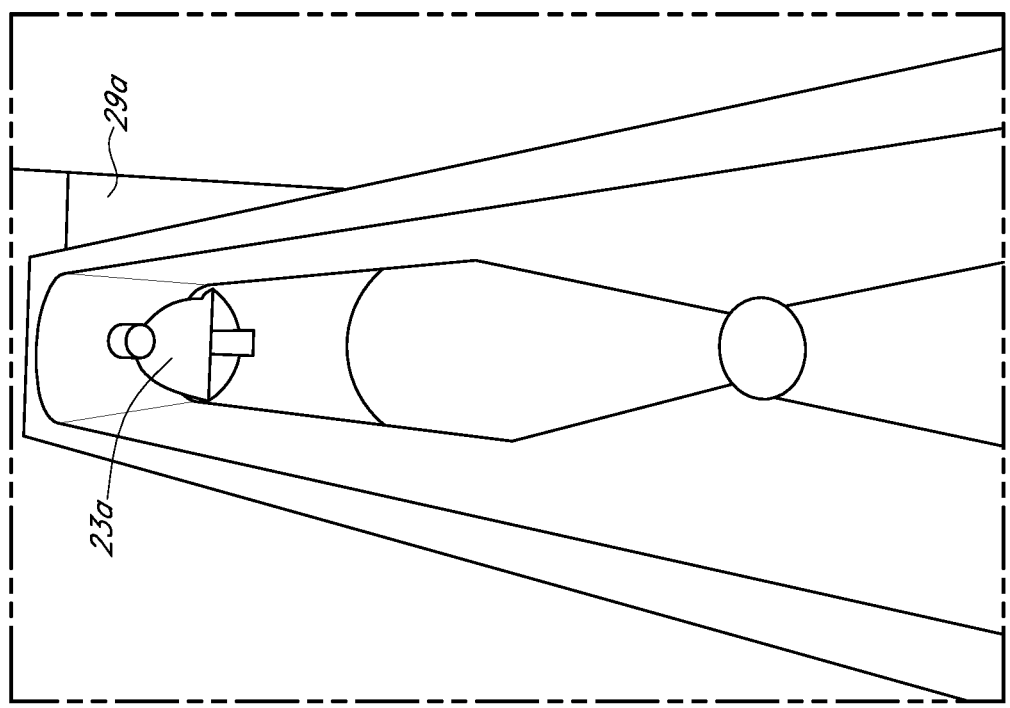
FIG. 10A is a perspective view of a portion of an illustrative embodiment of the main chamber of a flow cell.
Figure 10B:
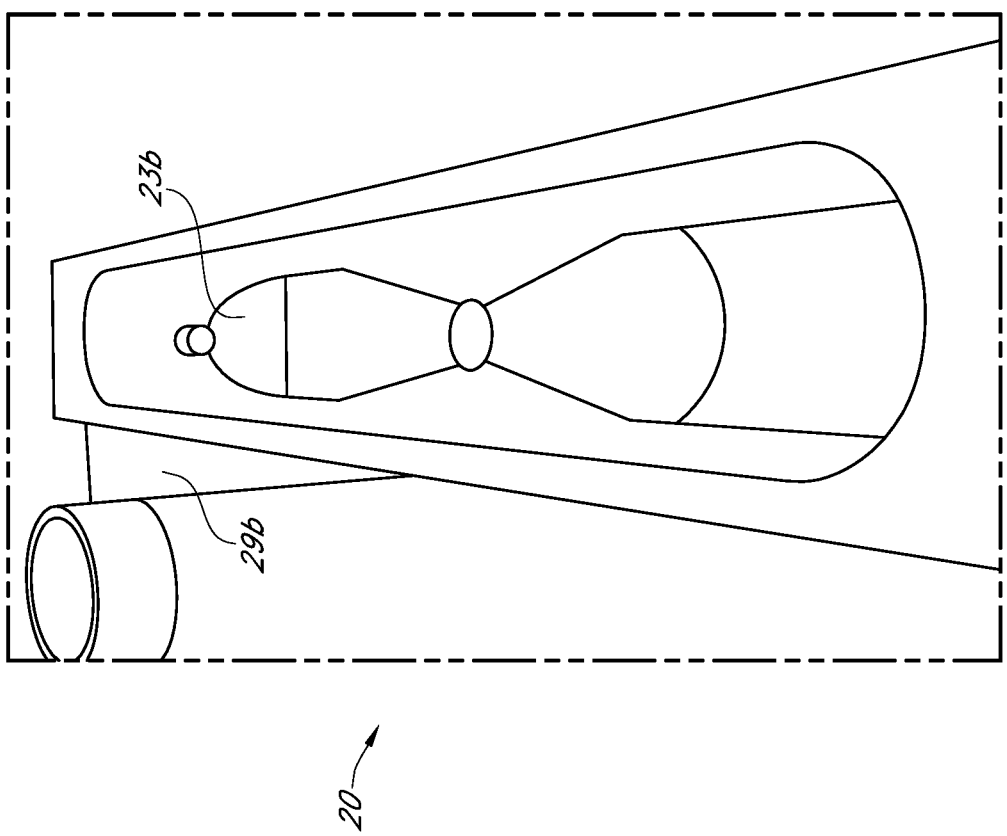
FIG. 10B is another perspective view of a portion of an illustrative embodiment of the main chamber of a flow cell.
Figure 10C:
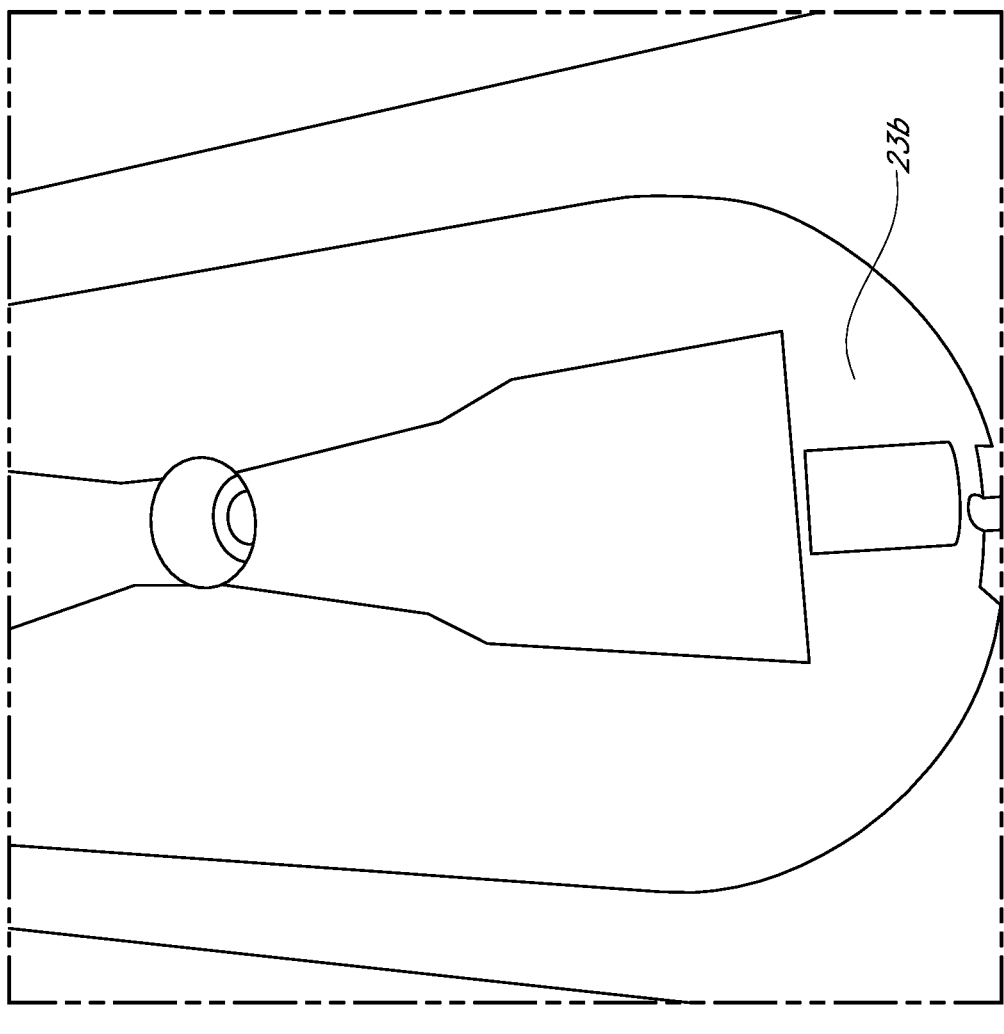
FIG. 10C is another perspective view of a portion of an illustrative embodiment of the main chamber of a flow cell adjacent the second cleaning nozzle.

A perspective view of the first cleaning nozzle 40 is shown in FIG. 7A and a perspective view of the second cleaning nozzle 50 is shown in FIG. 7B. A second cleaning nozzle plate 52 may be engaged with an exterior surface of the second end wall 21b as shown in FIG. 7C, and fluid may be supplied to the second cleaning nozzle 50 via fluid conduit and/or piping 14 external to the main chamber 20 (as shown in FIGS. 1C & 7C) in combination with a second cleaning nozzle fluid conduit 54 positioned internal with respect to the main chamber 20 extending from the second end wall 21b to the weir 28 as shown at least in FIG. 1D. Other structures and/or methods may be used to provide fluid to the cleaning nozzles 40, 50 without limitation unless otherwise indicated in the following claims. A front view of an illustrative embodiment of a second cleaning nozzle plate 52 and a side view thereof are shown in FIGS. 7D and 7E, respectively, wherein various dimensions are provided. However, other second cleaning nozzle plates 52 having different dimensions and/or differently configured may be used without limitation unless otherwise indicated in the following claims.

Figure 12A:
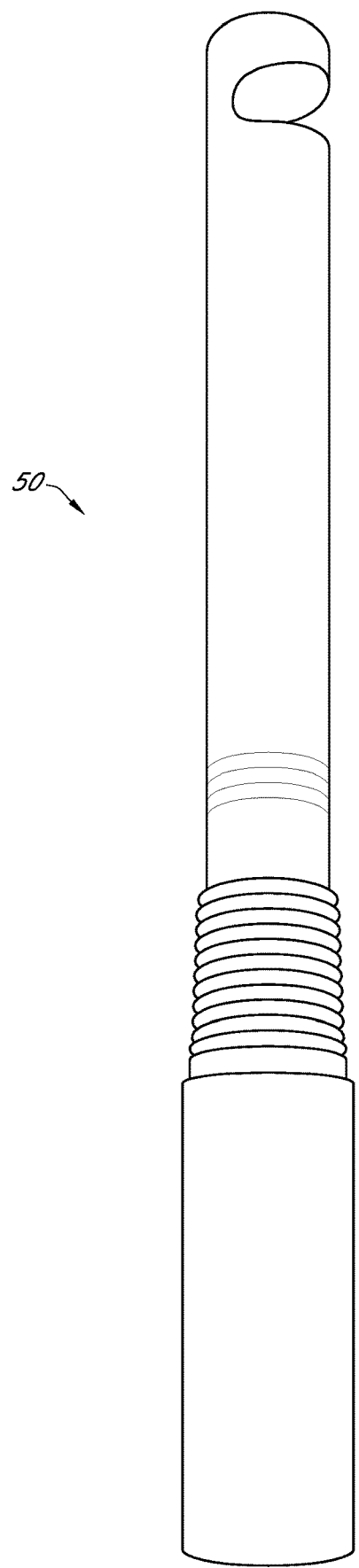
FIGS. 12A-12C provide various views of another illustrative embodiment of a second cleaning nozzle.
Figure 12B:
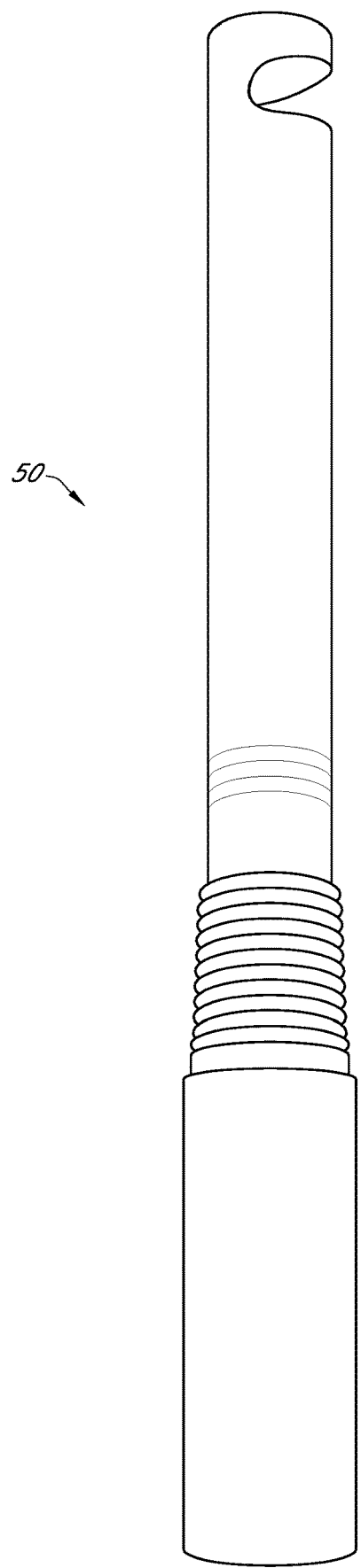
Figure 12C:
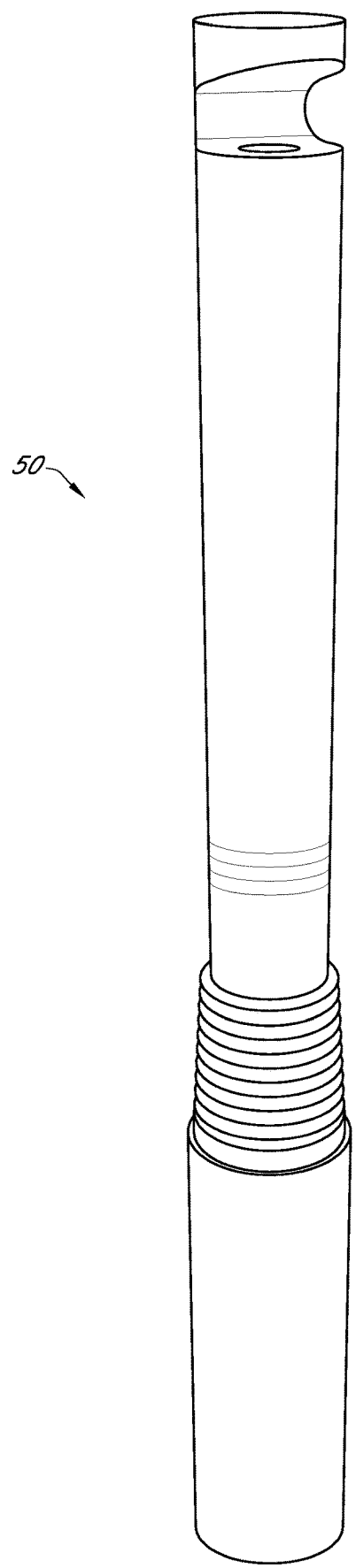
Figure 13A:
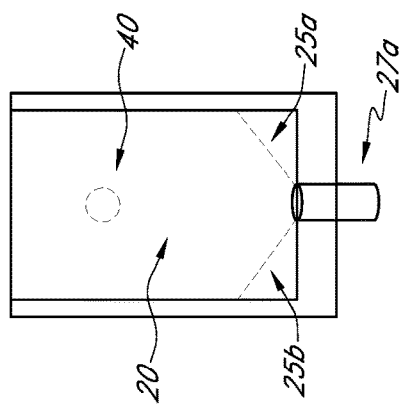
FIG. 13A is a side view of an illustrative embodiment of a portion of a flow cell showing various angles of a portion of the main chamber.
Figure 13B:
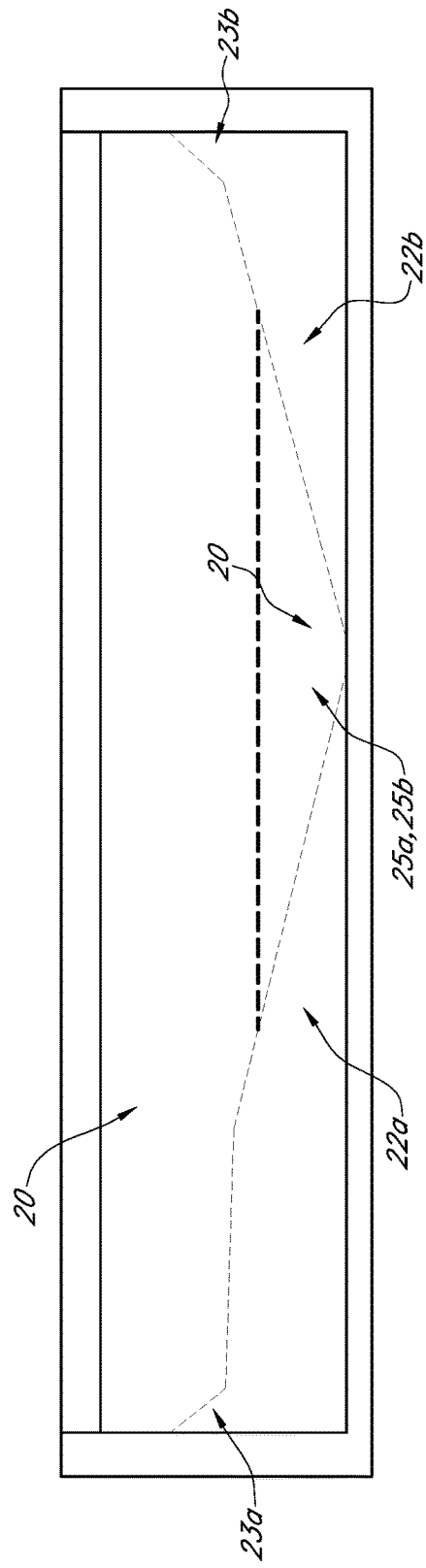
FIG. 13B is a side view of the embodiment of a portion of the flow cell shown in FIG. 13A.

Another illustrative embodiment of a second cleaning nozzle 50 (which may be configured with an outlet port and from materials as disclosed above from BETE) is shown in FIGS. 12A-12C. It is contemplated that the installation procedure for the embodiment of a second cleaning nozzle 50 shown in FIGS. 12A-12C as part of a retrofit kit (as described in further detail below) may be greatly simplified, which may impart a reduction in time required for the installation as well as eliminate/mitigate various potential mistakes during installation without limitation unless otherwise indicated in the following claims. Additionally, using the embodiment of a second cleaning nozzle 50 as shown in FIGS. 12A-12C may eliminate the need for a second cleaning nozzle fluid conduit 54, such that the required fluid conduit may be integrally formed with the second cleaning nozzle 54 without limitation unless otherwise indicated in the following claims. Finally, the embodiment of a second cleaning nozzle 50 as shown in FIGS. 12A-12C may eliminate the need for a second cleaning nozzle plate 52, which may further reduce installation time and eliminate/mitigate various potential mistakes during installation without limitation unless otherwise indicated in the following claims.

A first inlet passage 26a may be formed in the interior portion of the main chamber 20 such that a terminal end of the first inlet passage 26a may be positioned within the slight decline portion 24 of the main chamber. A second inlet passage 26*b* may be formed in the interior portion of the main chamber 20 such that a terminal end of the second inlet passage 26*b* may be positioned adjacent the interface between the slight decline portion 24 and the first ramp 22*a*. Finally, a third inlet passage 26*c* may be formed in the interior portion of the main chamber 20 such that a terminal end of the second inlet passage 26*b* may be positioned in the first ramp 22*a* in a position in relative proximity to the secondary drain 27*a*. However, other positions, orientations, configurations, etc. of the first inlet passage 26*a*, second inlet passage 26*b*, and/or third inlet 26*c* may be used with the flow cell 10 as disclosed herein without limitation unless otherwise indicated in the following claims. Additionally, in other embodiments of the flow cell 10 a different number of inlet passages 26*a*, 26*b*, 26*c* may be used without limitation unless indicated in the following claims. Generally, it is contemplated that during use, sample fluid may flow into the main chamber 20 through one or more inlet passages 26*a*, 26*b*, 26*c* until the level of sample fluid is greater than the height of the weir 28, wherein the sample fluid may flow over the weir 28 and exit the main chamber through the primary drain 27*b* without limitation unless otherwise indicated in the following claims.

Referring now specifically to FIG. 1B, an illustrative embodiment of a base plate 30 may be formed with a first base plate inlet 32*a* and a second base plate inlet 32*b*, wherein each base plate inlet 32*a*, 32*b* may be engaged with piping 14, fluid conduit, and/or various fittings without limitation unless otherwise indicated in the following claims. It is contemplated that for some applications it may be advantageous to configure the first base plate inlet 32*a* as a primary inlet for sample fluid (which fluid may be analyzed by one or more sensors positioned in the flow cell 10) into the flow cell 10 and to configure the second base plate inlet 32*b* as a secondary inlet for sample fluid without limitation unless otherwise indicated in the following claims. The second base plate inlet 32*b* may also be configured as a pressurized sample inlet flushing mechanism 55 to supply a wash fluid to various portions of the flow cell 10 as described in further detail below and without limitation unless otherwise indicated in the following claims.

The base plate 30 may be formed with an inlet header 34 along a specific portion thereof, wherein the inlet header 34 may be in fluid communication with both the first and second base plate inlets 32*a*, 32*b*. The inlet header 34 may also be in fluid communication with the first, second, and third inlet passages 26*a*, 26*b*, 26*c* formed in the main chamber 20, such that pressurized sample fluid and/or wash fluid supplied to the inlet header 34 may be fluidly communicated to the inlet passages 26*a*, 26*b*, 26*c* and into the interior portion of the main chamber 20.

The base plate 30 may further be configured with a secondary drain passage 37*a* corresponding to the secondary drain 27*a* formed in the main chamber 20 and a primary drain passage 37*b* corresponding to the primary drain 27*b* in the main chamber for fluid to be removed from the main chamber 20. A secondary drain valve 38 and/or associated fluid conduit may be engaged with and in fluid communication with the secondary drain passage 37*a* and a primary drain valve (not shown) and/or associated fluid conduit may be engaged with and in fluid communication with the primary drain passage 37*b* to assist in fluid control within the main chamber 20. It is contemplated that for most applications it may be advantageous to not make the inlet header 34 in fluid communication with the secondary drain passage 37*a*, although in other applications it may be advantageous to selectively control such fluid communication by means of another valve and/or other suitable structure and/or method without limitation unless otherwise indicated in the following claims.

Figure 4A:
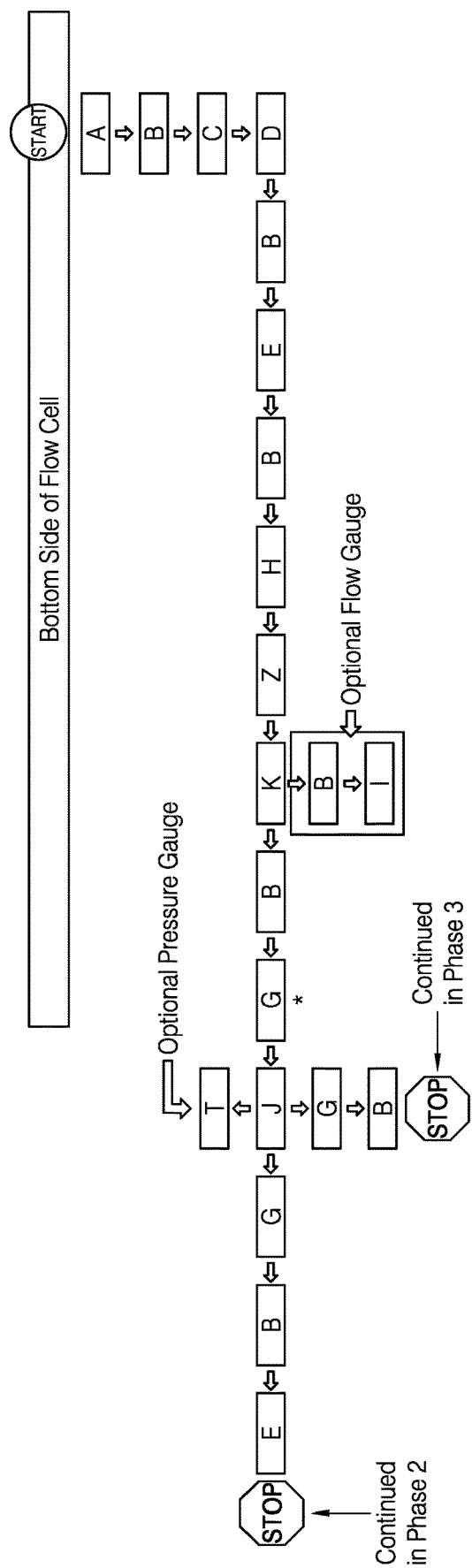
FIG. 4A is a block diagram representing the various fluid conduit connectors and elements that may be used to construct the illustrative embodiment of a portion of the piping for the flow cell shown in FIGS. 1A-3E.
Figure 4B:
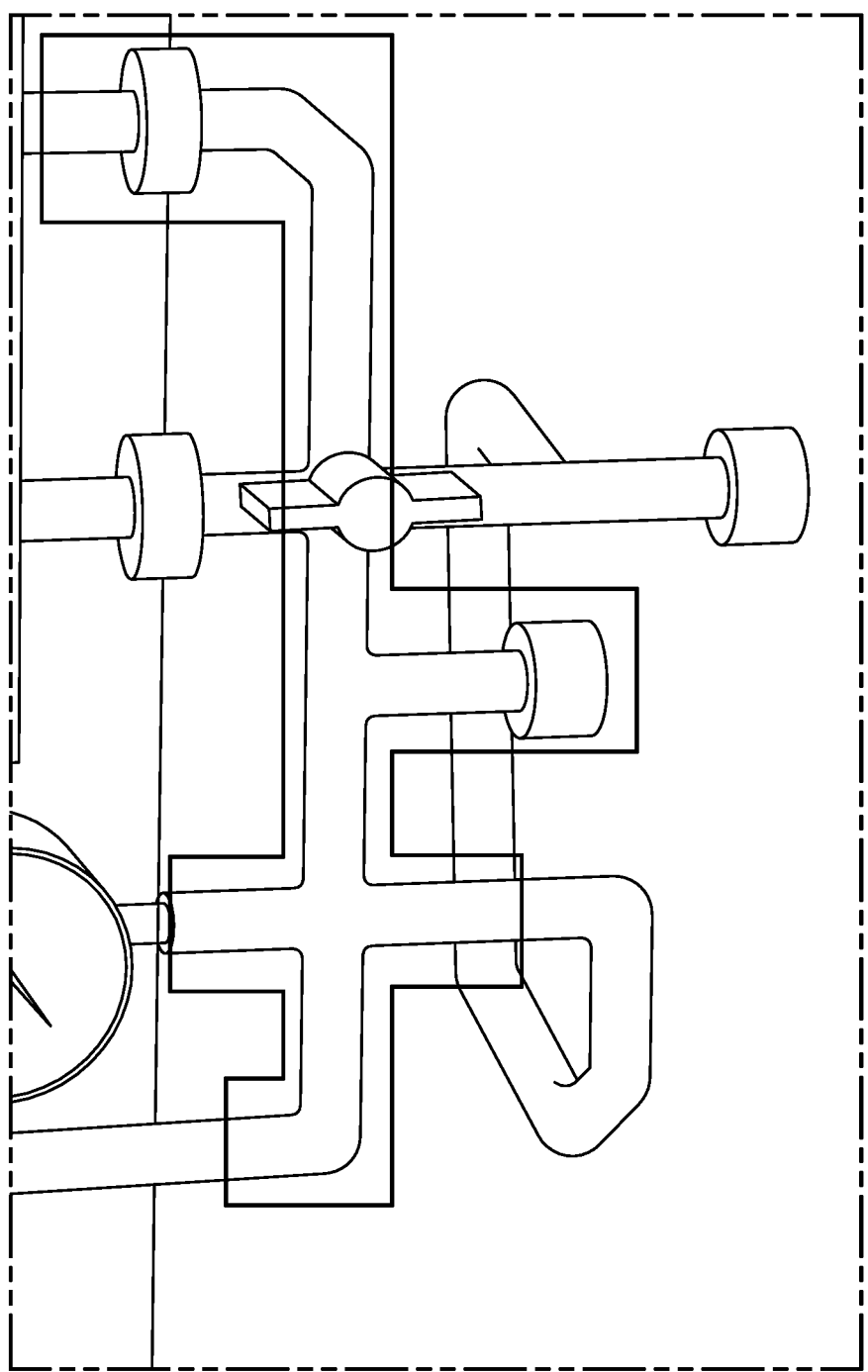
FIG. 4B is a front view of the portion of the piping represented by FIG. 4A.
Figure 4C:
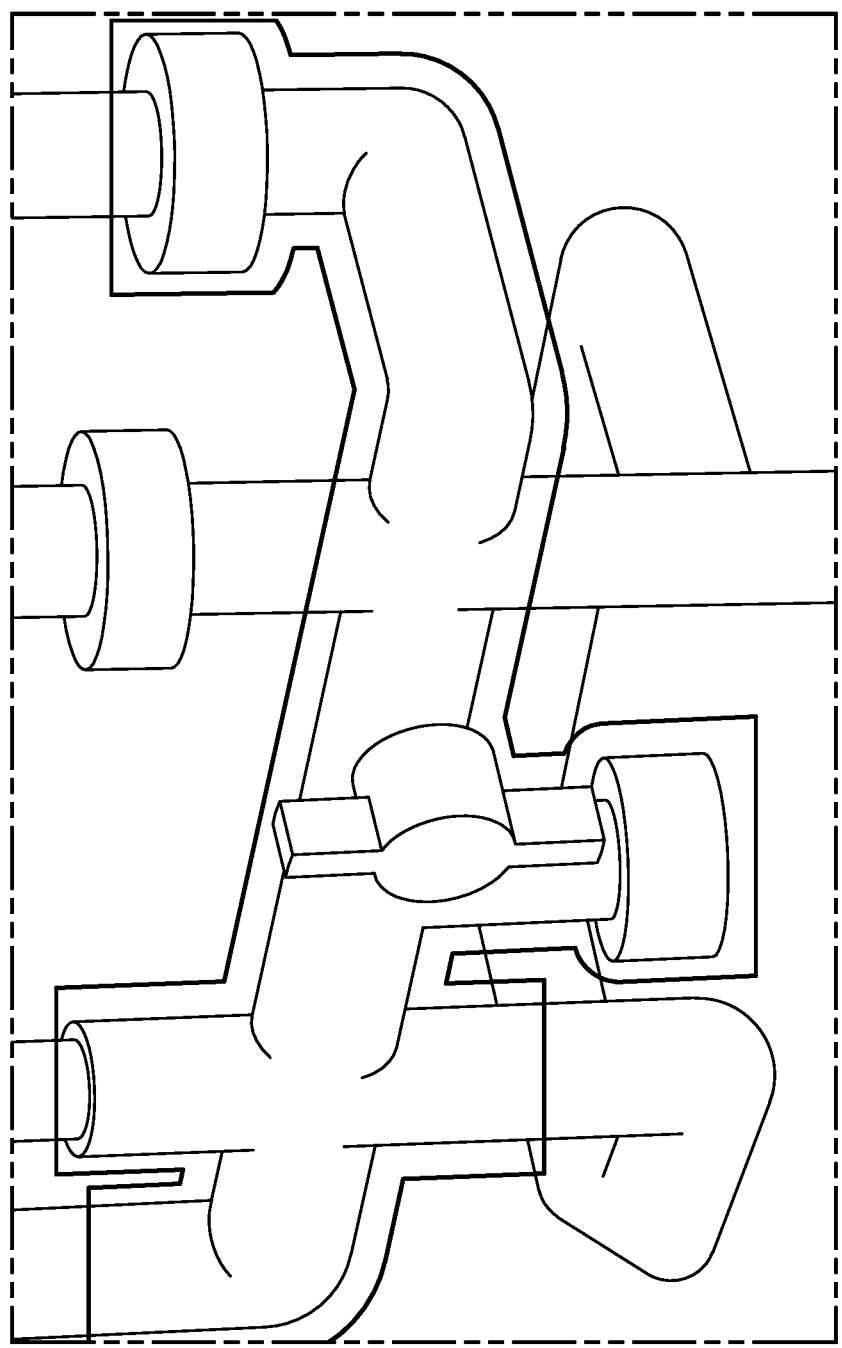
FIG. 4C is a perspective view of the portion of piping represented by FIG. 4A.
Figure 5A:
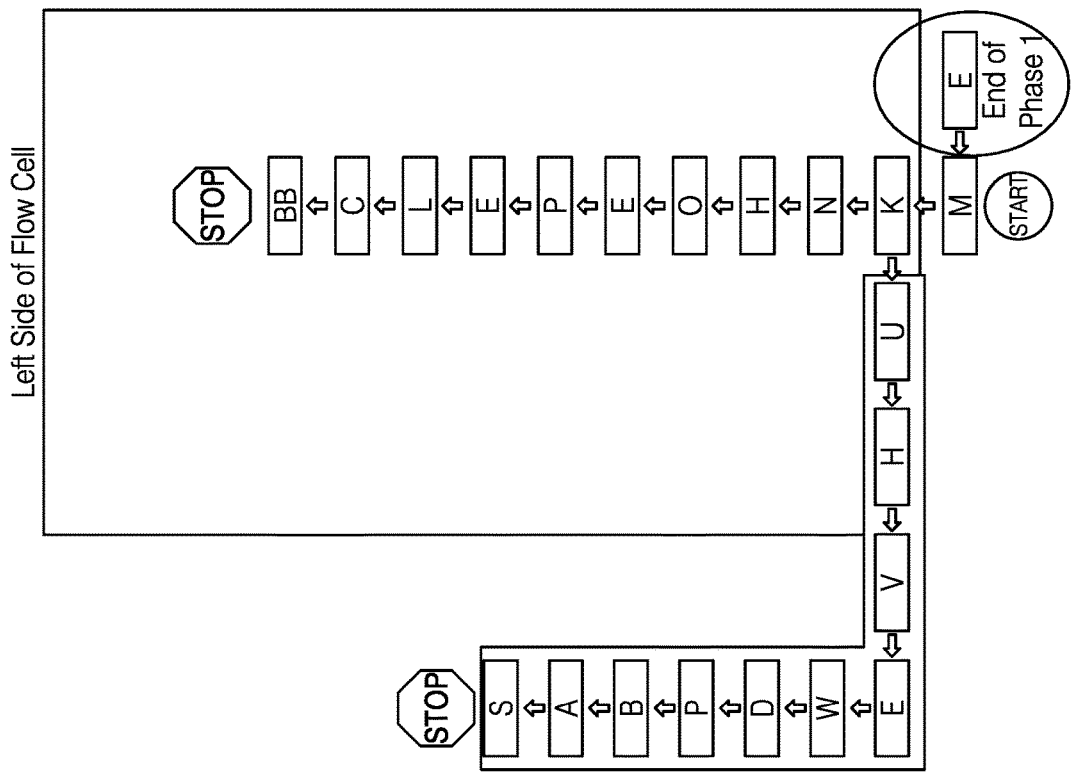
FIG. 5A is a block diagram representing the various fluid conduit connectors and elements that may be used to construct the illustrative embodiment of another portion of the piping for the flow cell shown in FIGS. 1A-3E.
Figure 5B:
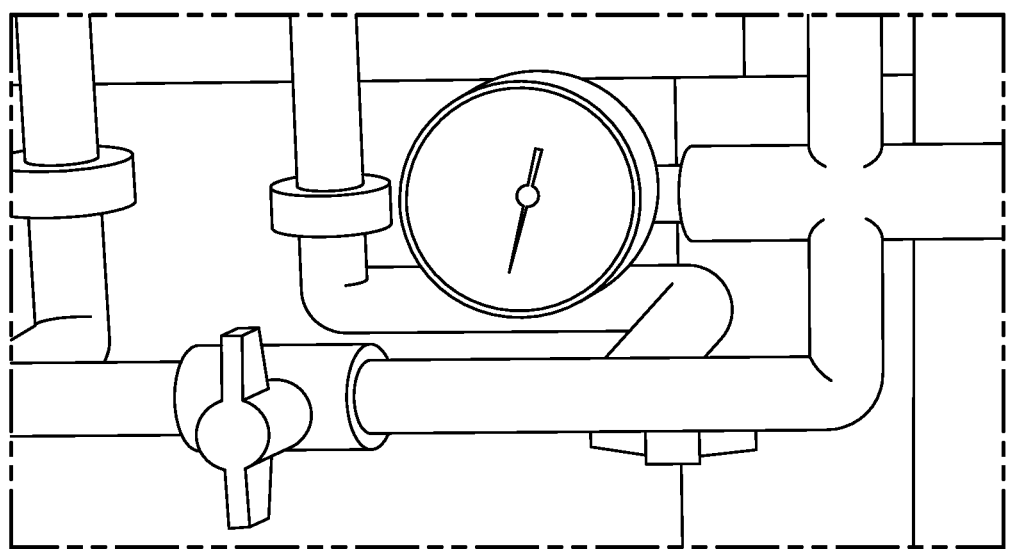
FIG. 5B is a front view of the portion of the piping represented by FIG. 5A.
Figure 5C:
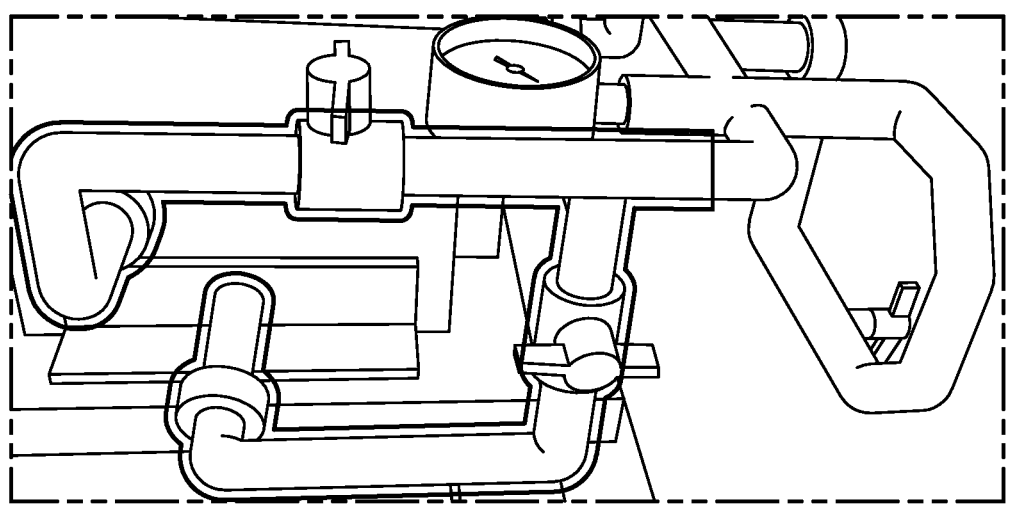
FIG. 5C is a perspective view of the portion of piping represented by FIG. 5A.
Figure 6A:
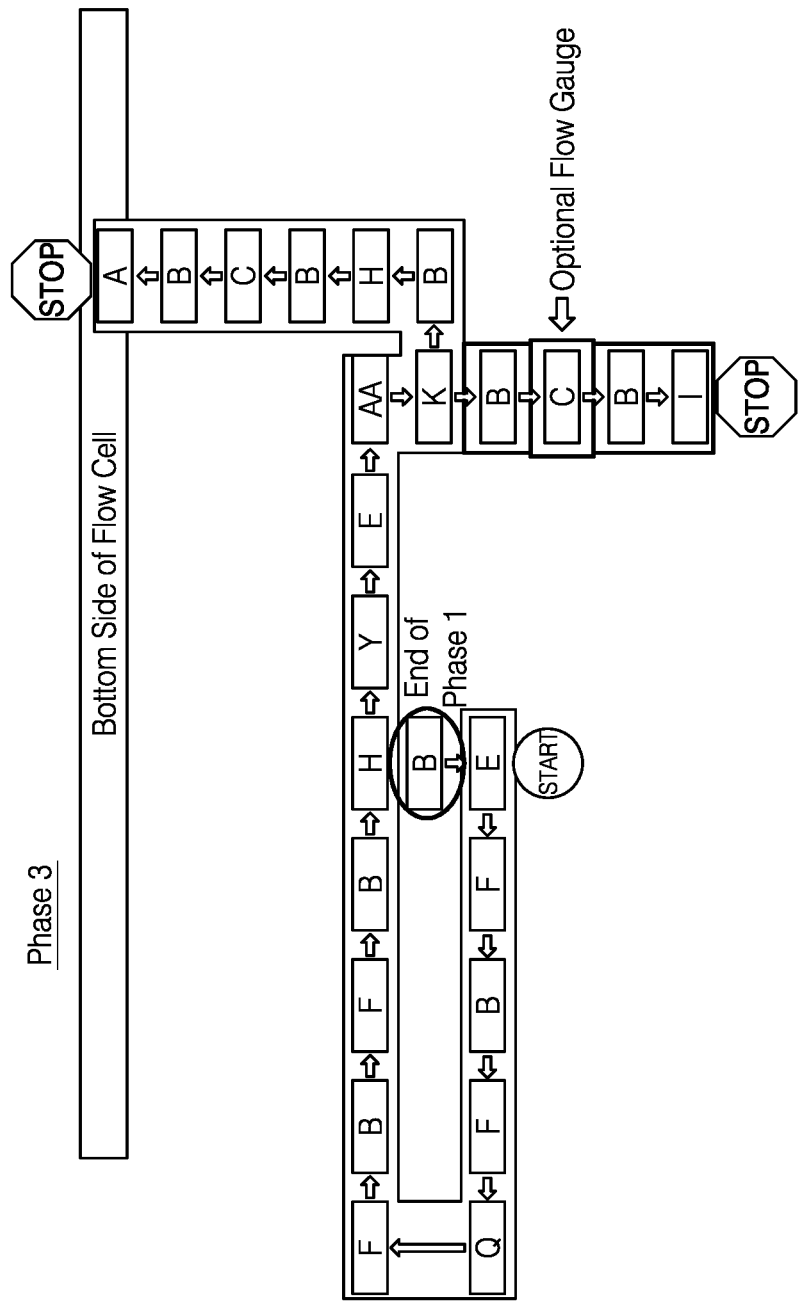
FIG. 6A is a block diagram representing the various fluid conduit connectors and elements that may be used to construct the illustrative embodiment of another portion of the piping for the flow cell shown in FIGS. 1A-3E.
Figure 6B:
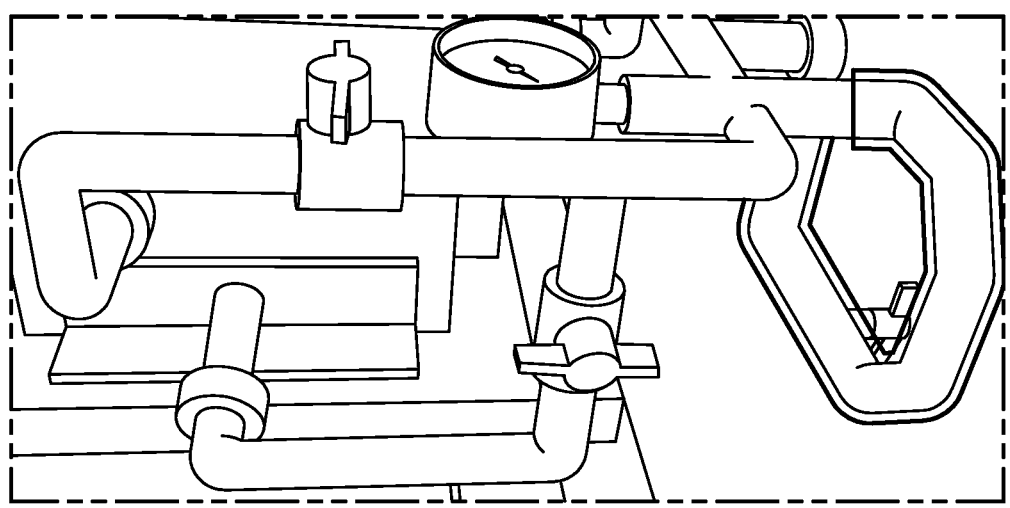
FIG. 6B is a perspective view of the portion of the piping represented by FIG. 6A.
Figure 6C:
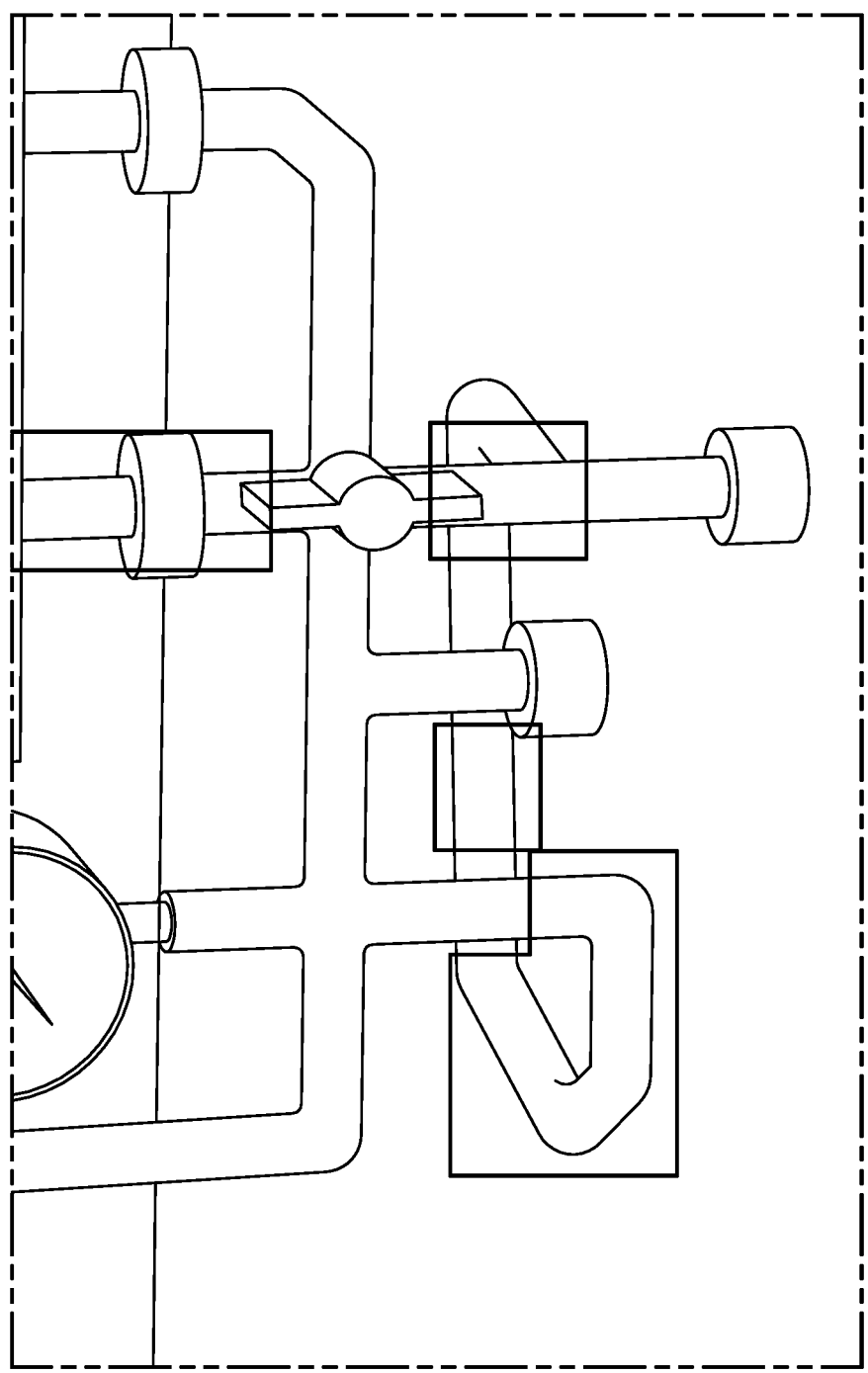
FIG. 6C is a front view of the portion of piping represented by FIG. 6A.
Figure 6D:
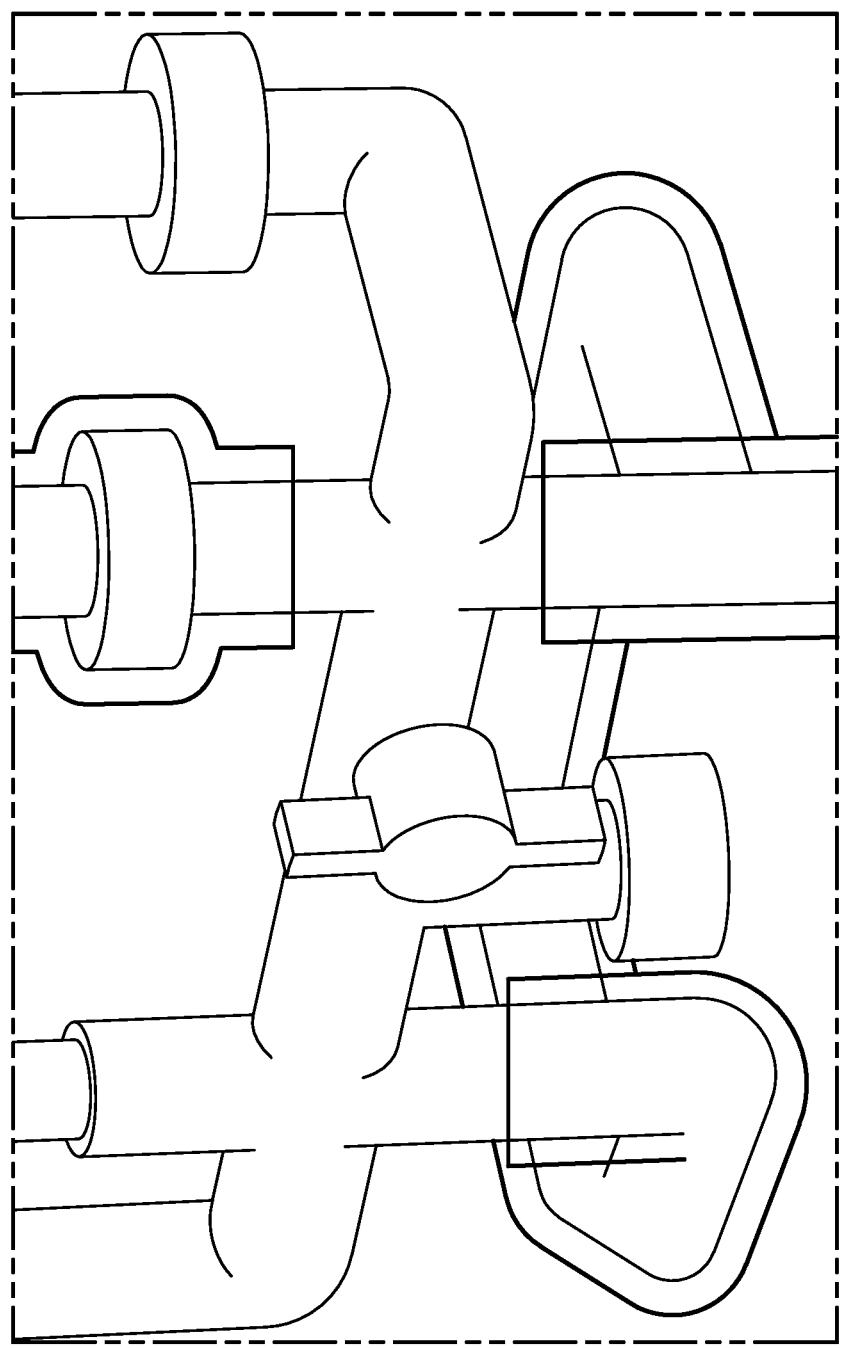
FIG. 6D is a perspective view of the portion of the piping represented by FIG. 6A.

Referring now to FIGS. 2B-3E, an illustrative embodiment of piping 14 that may be used in a flow cell 10 according to the present disclosure may include multiple valves 12, wherein the illustrative embodiment pictured herein includes 5 valves engaged with the piping 14 adjacent the first end wall 21*a* of the main chamber 20. The specific fittings and configuration thereof for the piping 14, valves 12, pressure gauge 15, and flow meter 16 used for the illustrative embodiment thereof pictured in FIGS. 1A, 1B, 2A-3E, 4B, 4C, 5B, and 5C are represented by the diagrams shown in FIG. 4A (which corresponds to the valves 12 and piping 14 shown in detail in FIGS. 4B & 4C) and FIG. 5A (which corresponds to the valves 12 and piping 14 shown in detail in FIGS. 5B & 5C). As shown in FIG. 6 and in the table immediately below, each specific letter in FIGS. 4A & 5A corresponds to a specific fitting and/or piping element. Additional details regarding each component is provided in Appendix A, which is included herewith and made a part of this disclosure. Other embodiments of a flow cell 10 according to the present disclosure may have a greater or fewer number of valves 12, piping 14, fittings, different dimensions, different configurations thereof, etc. without limitation unless otherwise indicated in the following claims.

A—½" CPVC Male Adapter
B—½" CPVC Tube×2.5 cm
C—½" CPVC Union
D—½" CPVC Street Elbow
E—½" CPVC Elbow
F—½" 45° CPVC Elbow
G—½" Coupling CPVC
H—½" CPVC Socket×Socket Ball Valve
I—½" Slip×½" FPT CPVC Adapter
J—½" PVC Cross (8×8×8)
K—½" Tee Scb 40
L—½" CPVC Tube×3.8 cm
M—½" CPVC Tube×3.5 cm
N—½" CPVC Tube×5.5 cm
O—½" CPVC Tube×5.7 cm
P—½" CPVC Tube×3.2 cm
Q—½" CPVC Tube×2.8 cm
R—½" CPVC Cap
S—½" CPVC×½" PIP Drop Ear Elbow
T—½"×¼" Flush Spigot Threaded PVC
U—½" CPVC Tube×3.7 cm
V—½" CPVC Tube×5.0 cm
W—½" CPVC Tube×10.2 cm
X—½" CPVC Tube×5.2 cm
Y—½" CPVC Tube×5.3 cm
Z—½" CPVC Tube×3.9 cm
AA—½" CPVC Tube×3.1 cm
BB—Left Spray Nozzle*
CC—⅜" OD×½" NPTF Plastic Quick Connect
DD—⅜"OD×⅜" MIP Plastic Quick Connect Second half of C is constructed/designed within the sprayer. Sprayer screws into block prior to attaching Water Feed Pipe assembly.

Generally, in the illustrative embodiment of a flow cell 10 the valves 12 and piping 14 may be configured to provide at least two external inlets, wherein a first external inlet may be configured for use primarily as a sample fluid inlet and a second external inlet may be configured for use primarily as a wash fluid inlet (and as a secondary sample fluid inlet). The valves 12 and piping 14 may be configured such that the user may direct flow to either the first base place inlet 32*a* and/or second base plate inlet 32*b* by closing certain valves 12 and opening certain valves 12 in conjunction with supplying the sample fluid to the desired external inlet(s) as shown at least in FIGS. 4A & 5A.

Additionally, the valves 12 and piping 14 may be configured such that the user may direct a flow of wash fluid to the first cleaning nozzle 40 and/or second cleaning nozzle 50 (separately or simultaneously), and/or to the inlet header 34 (separately or simultaneously with respect to the first or second cleaning nozzles 50). Wash fluid may be supplied to the inlet header 34 via the second base plate inlet 32*b*, and the valves 12 and piping 14 may be configured such that the wash fluid may be used to flush various portions of the valves 12 and piping 14 with wash fluid (e.g., first external inlet with which the supply of wash fluid is not directly engaged), various portions of the inlet header 34, the first base plate inlet 32*a*, and/or the inlet passages 26*a*, 26*b*, 26*c* formed in the main chamber 20 without limitation unless otherwise indicated in the following claims. In other embodiments the wash fluid may be supplied to the flow cell 10 in a different manner (e.g., via the first base plate inlet 32*a*, via a different inlet, etc.) and the flow cell 10 may be configured such that the wash fluid may differently flush the same or other portions of the flow cell 10 without limitation unless otherwise indicated in the following claims.

It is further contemplated that the flow cells 10 described herein may provide a viable solution to a pre-existing flow cell (trough), used within the municipal industry for water analysis. The flow cell, a critical component to an online analytical instrument (analyzer), may come in a variety of shapes and sizes, and is responsible for supplying water to an array of sensors, each monitoring a specific parameter within the body of water flowing through the trough. The dependability, reliability, and precise and accurate data output of this instrument is critical, but not seen with all end users that utilize the options found in the prior art. The flow cells 10 disclosed herein may offer an easy, turn-key solution, for owners of certain prior art designs (such as the Hach Source Water Monitoring Panel), without having to invest thousands of additional dollars on a newly designed trough. That is, certain aspects of the flow cells 10 disclosed herein may be offered as a retrofit kit for certain Hach brand Source Water Monitoring Panels. The retrofit kit may provide an affordable solution that not only resolves multiple issues reported, but also delivers additional key features, providing more control and proactive measures, greatly improving the device's original capabilities.

In one illustrative embodiment a retrofit kit, the retrofit kit may include the following contents:

Modification Kit Contents
(1) ¾" Ball Valve
(2) ⅜"×⅜" NPTF Plastic Quick Connect Fitting
(1) Right Aluminum Mounting Bracket
(1) Left Aluminum Mounting Bracket with Wash Connect
(1) Left Side Sprayer Nozzle
(1) Right Side Sprayer Nozzle
(1) Water Feed Pipe Assembly
(1) Floor Insert
(1) Floor Insert Adhesive
(1) ¼" NPT Male Plug
(1) ¾" NPT Barb
(1) ⅜" OD Tube×76 cm
(1) ¾" NPT×3" Pipe Nipple w/O-Ring
(2) ½"×⅜" NPTF Plastic Quick Connect Fitting
(2) ½"×½" NPTF Plastic Quick Connect Fitting
(2) 5/32" 20×¾" SS Nut
(2) 3/16" SS Washer
(2) 5/32" 20×¾" SS Bolt
(1) PSI Pressure Gauge
(1) Flow Gauge CPVC Easy Connects
(1) Left Side Drilling Template
(1) Right Side Drilling Template
(1) Universal Bottom Drilling Template
(1) Tool Kit
(1) Thread Tape
(1) Instruction Manual
Tool Kit Contents (Optional Purchase)
(1) ½" Drill
(1) ¼" Drill
(1) 37/64" Drill
(1) 7/16" Drill
(1) 23/32" Drill
(1) 59/64" Drill
(1) ¾" Tap
(1) 7/16" Tap
(1) ¼" Tap
(1) ½" Tap
(1) ¾" Tap
Not Included in Kit
(1) Flow Gauge It is contemplated that various embodiments of a flow cell 10 constructed using an illustrative embodiment of the retrofit kit may provide a field-tested solution to at least the following troubled areas that may be found in the prior art without limitation unless otherwise indicated in the following claims:

1. The cleaning process in the prior art may be time consuming and difficult.
2. In the prior art there may be clogging of sample ports, resulting in the instrument being offline for extended periods of time.
3. In the prior art there may be drifting and/or erratic values of the data received due to the accumulation of sediment, as well as monitoring stagnant water due to short circuiting of the sample, and/or loss of sample flow.
4. Prior art devices may exhibit an inability of the instrument to obtain high enough flow rates/sample pressure to aid in adequate sample turnover, as well as clog prevention.
5. The prior art may exhibit a lack of controls that in turn limits the end users' capabilities.
6. The prior art may not provide a cleaning system that is adaptable for all site locations.

Once the flow cell 10 has been configured according to those pictured and described herein, which may be accomplished via a retrofit kit as disclosed herein, the flow cell 10 may provide at least the following benefits and/or features without limitation unless otherwise indicated in the following claims:

1. The ability to withstand over triple the flow-rate capacity of sample fluid of the original design, reaching flow rates of sample fluid in excess of 10,000 mL/min (and in some applications in excess of 12,000 mL/min compared to approximately 4,000 mL/min in the prior art), while maintaining a sample PSI greater than 10 during normal operation.
    a. This may provide the instrument with quicker sample turnover for faster detection of current water conditions.
    b. This may provide higher sample pressures (PSI) aiding in keeping sample ports within the flow cell cleared of any obstruction.

c. This may provide longer life to the sample pump being utilized to pump your raw sample to the flow cell.
d. This may provide the ability to use the flow cell with a larger variety of sensors and applications.
2. The ability to use 3 separate washing ports (independently or simultaneously, wherein the prior art only provides one cleaning nozzle on the left side of the flow cell) for optimum cleaning/rinsing of the sample well/main chamber 20, all raw water sample ports (first inlet passage 26a, second inlet passage 26b, third inlet passage 26c), as well as any sensors being utilized.
   a. With the optional pressure gauge, the end user can easily see if their facility's clean water supply is providing enough pressure to effectively clean all three rinsing locations simultaneously. If not, illustrative embodiments of the flow cell 10 (and specifically the configuration of the valves 12 and piping 14) may be configured to allow each washing port to be used individually (i.e., one at a time), isolating all available water pressure to each area independently for optimum cleaning.
   b. Supplemented by a new floor design in the main chamber 20, as well as a centralized secondary drain 27a, the flow cell 10 can be fully clean, including sensors left inside the main chamber 20 during cleaning, within a couple minutes, eliminating the frustration of a time-consuming cleaning process.
3. Redundancy in the ability to feed raw sample fluid at the clean water junction port.
   a. In the event an obstruction makes its way into a portion of the raw sample port of the main chamber 20 and/or base plate 30 (i.e., first base plate inlet 32a, inlet header 34, inlet passage(s) 26a, 26b, 26c), which obstruction may block and/or impede sample fluid flow to the flow cell, simply isolating various valves 12 redirects raw sample fluid flow into the main chamber, utilizing all sample ports, keeping this instrument up and running, eliminating the instrument from being offline.
4. The ability to monitor and backwash the raw sample fluid line from the source, all the way to the flow cell.
   a. A user may utilize a pressurized clean water supply to back feed the length of the sample line, clearing any clogs and/or debris that may form. By utilizing the optional pressure gauge, a user may monitor the degree of obstruction by observing the amount of back pressure that is occurring. This indication also allows the end user to know when the sample line has become fully cleared, by the pressure gauge no longer indicating the presence of any back pressure.
   b. With the optional raw sample fluid flow gauge, a user may easily monitor and trend flow going to the flow cell, allowing the end user to detect clogs forming within the sample line, triggering the end user to execute a sample line backwash. This early detection capability allows the analyzer to stay online, eliminating a lengthy time spent offline.
5. Provide the end user with the tools to obtain a constant stream of quality data that can be trusted.
   a. By providing sensors with an environment that is optimum for monitoring water quality parameters, the sensors will do just that.
   b. Providing a system to the end user that is less labor intensive, easily maintained and kept clean, more controls and features to further safeguard against public health and operational inefficiencies, the intended usefulness of this analyzer surfaces.

Additional benefits/advantages (shown in the second column) that may be attributable to one or more features (shown in the first column) of an illustrative embodiment of a flow cell 10 as modified by an embodiment of a retrofit kit are shown in Table 1 below. These modifications/features are not meant to be an exhaustive list, nor are the attributable benefits/advantages associated therewith unless otherwise indicated in the following claims.

TABLE 1 features of and illustrative embodiment of a flow cell 10 and at least some advantages that may be attributed to such feature.

| Feature | Advantage |
|---|---|
| Sample ports (hydraulic modification) | Aids in clog prevention and short circuiting of sample. Allows system to withstand higher sample flows and pressure. |
| Bracket re-design | Aids in increasing sample flow capacity and right-side washing. |
| Sprayer Module | Allows for right-side washing. |
| Centralized drain | Allows for quick and easy removal of sediment. |
| Trough floor re-design | Directing all sediment towards centralized drain leaving no areas of sediment |
| Independent valving installed | Allows for complete cleaning while accommodating for sites with low clean water pressure availability. Also allows for other features, such as sample line backwashing, and utilizing backup raw sample port. |
| Sample port flushing | Keeps sample flowing evenly, eliminating short circuiting. Clears blockages caused by sediment. |
| Left and right-side flushing | Allows for a complete sediment removal of the trough, as well as sensors (higher clean water PSI required for rinsing of sensors). Aids in preventing fouling of sensors due to sediment |
| PSI monitoring | Monitoring the degree of your obstruction during sample line backwashing. Provides operator guidance if your clean water supply pressure is adequately cleaning, guiding you to use sprayer washers independently, rather than simultaneously, for optimum cleaning. When in conjunction with the sample line backwashing feature, also allows the operator to visually see to what degree is the sample line clogged, as well as when the sample line is fully cleared. |
| Raw flow monitoring | Allows the operator to maintain an exact desired flow rate that best suits the sensors being utilized. Also provides facilities the ability to catch the formation of clogs within the sample line, before a clog occurs. This proactive feature, coupled with the new ability to backwash the sample line, always allows the analyzer to remain online. |
| Secondary raw sample | Allows the analyzer to stay functioning, utilizing the same sample hydraulic path as the primary inlet, but from a second location. This feature provides redundancy, allowing the analyzer to remain online if a clog occurs within the sample port from any obstruction (Example - Zebra Mussel becomes lodged). |

TABLE 1-continued features of and illustrative embodiment of a flow cell 10 and at
least some advantages that may be attributed to such feature.

| | |
|---|---|
| Sample line backwashing | Allows the analyzer to fully flush out the sample line feeding the analyzer within minutes. Coupled with the PSI monitoring feature, the operator will be aware of a clog forming before sample is cut off to the analyzer, allowing proactive measures to be executed. |

Another advantage of a flow cell 10 as disclosed herein is that the data obtained by sensor(s) (not shown) utilized therewith may collect data that is considered "clean" (e.g., reliable, accurate, etc.) and validated such that it may be used to program alarm settings. In one illustrative embodiment the final percentile calculations for statistical alarm settings were found to be as follows without limitation unless otherwise indicated in the following claims: (1) pH: 7.5 (2.3%), 8.5 (76.2%); (2) DO: 8.5 (32.4%), no high alarm; (3) Turb: 10 (17%), 100 (95.6%); (3) Conductivity: 150 (8.35%), 450 (72%); (4) ORP: no low alarm, 600 (99.99%); and, (5) UVAS: 15 (36.5%), 40 (99.9%).

Generally, this functionality may be extremely beneficial in many applications because various flow cells 10 are placed in an application such that the flow cell 10 and/or sensors engaged therewith are intended to be used as a warning system for the presence of contaminants and/or other undesirable fluid characteristics. If the data is not reliable, the user cannot create and set operational alarms that provide any meaningful alert. In certain configurations, the alarm setpoints may communicate with a SCADA system, such that an operator may be alerted to any operational aspect outside the norm. A flow cell 10 configured according to the present disclosure may allow alarm settings to be determined based off the statistical analysis of the "clean" data obtained from sensors engaged with the flow cell 10. Such capability may directly relate to both compliance and public health scenarios.

Additional Embodiments of Fluid Monitoring Systems & Methods

Referring now to FIGS. 15-25I, other illustrative embodiments of a flow cell 110 and/or components thereof are shown therein. Generally, and without limitation unless otherwise indicated in the following claims, the embodiments of a flow cell 110 and/or components thereof shown in FIGS. 15-25I may provide at least the advantages, functionality, and/or other benefits as previously described above for illustrative embodiments of a flow cell 110 and/or components thereof shown in FIGS. 1-14B and simultaneously may provide additional advantages, functionality, and/or other benefits. Additionally, throughout FIGS. 16A-23, illustrative dimensions and/or relative positions of various features of the flow cell 110 and/or components thereof may be shown. However, these dimensions are for illustrative purposes only and in no way limit the scope of the present disclosure unless otherwise indicated in the following claims, though it is contemplated that for certain applications one or more listed dimensions may constitute a portion and/or feature of a preferred embodiment. Additionally, in light of the present disclosure it will be apparent to those skilled in the art that various fittings, connections, interfaces, etc. may be advantageously configured as providing a hermetic seal between respective components without limitation unless otherwise indicated in the following claims.

Figure 15:
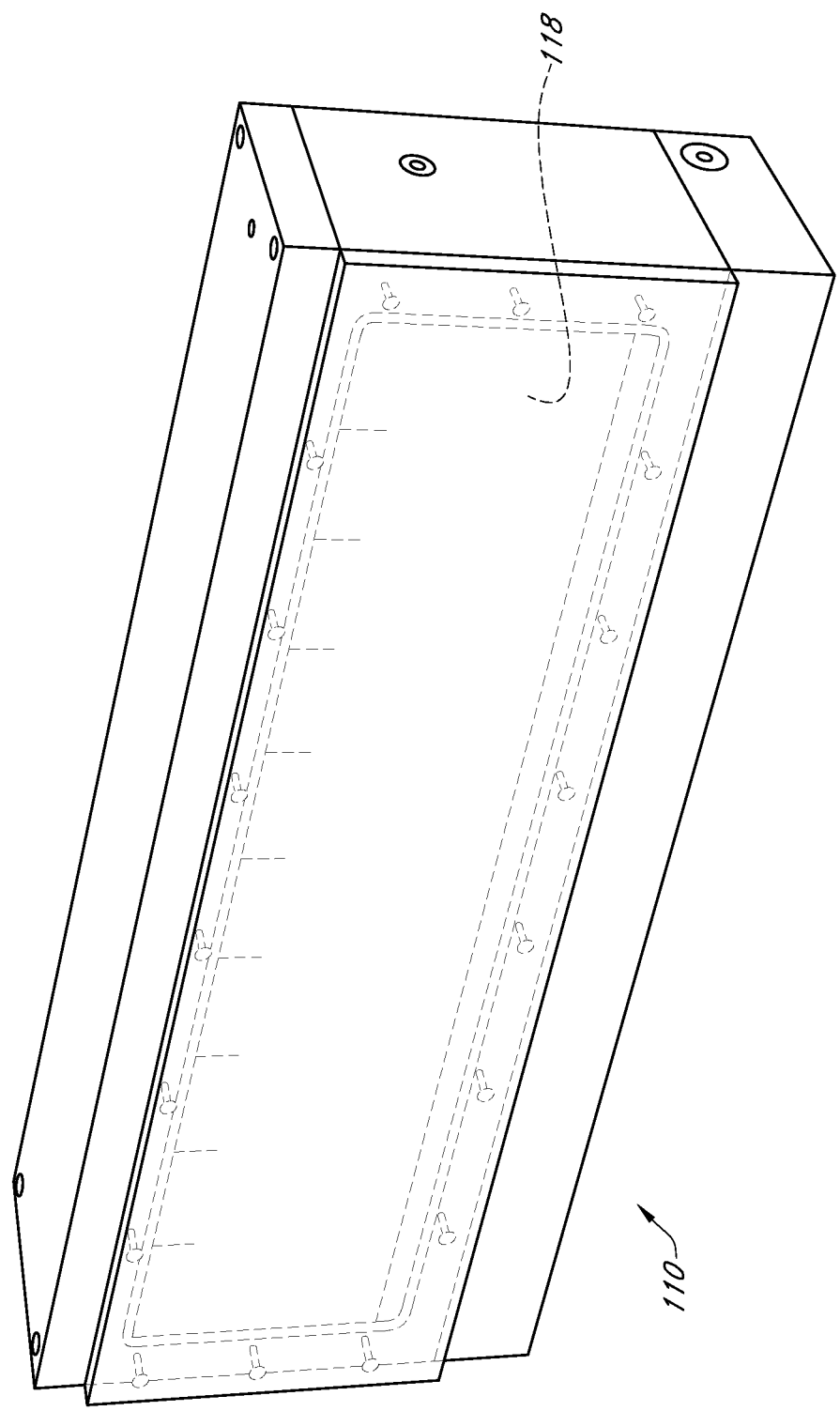
FIG. 15 provides a perspective view of a second illustrative embodiment of a flow cell.

Referring now specifically to FIG. 15, a perspective view of an illustrative embodiment of a flow cell 110 is shown therein. In this embodiment, a transparent panel 118 may be engaged with a portion of the main chamber 120 to allow a user to visually inspect various interior aspects of the flow cell 110, fluid flow within a portion of the flow cell 110, and/or various characteristics of the sample fluid without limitation unless otherwise indicated in the following claims.

Additionally, the flow cell 110 may be configured with a backup power supply 184 (which in one illustrative embodiment may be configured as a rechargeable battery as shown at least in FIG. 27C) to provide enough power to allow the flow cell 110 an communications to operate adequately for a predetermined amount of time if a power outage to a facility occurs. Such a configuration may make the flow cell ideal for remote locations as well as providing an extra layer of security due to the ability to continue to monitor/control a process in the event of a power loss. A programmable logic controller (PLC) and/or programmable automation controller (PAC) in communication with the flow cell 110 may be configured to automatically switch the power supply to a battery and may be configured to alert certain personnel to the loss of power such that reactive measures may be taken while continually keeping the process online.

The illustrative embodiment of a battery and flow cell 110 may be in communication with a PLC and/or PAC, which PLC and/or PAC may in turn be configured to allow a user to interact with the PLC and/or PAC locally via a human-machine interface (HMI, which is described in further detail below) engaged with the flow cell and/or remotely via a graphical user interface (GUI) displayed on a computing device (e.g., smart phone, tablet, computer, etc.) for controlling the PLC and/or PAC and/or flow cell 110, which GUI may be accessed via a wireless connection such as Bluetooth, cellular, mobile broadband, various 802.11 protocols and/or any other suitable method. The PLC and/or PAC may be configured to alert various personnel when certain conditions are present, such as a loss of power without limitation unless otherwise indicated in the following claims.

An illustrative embodiment of a communication scheme for various components that may be implemented with a flow cell 110 is shown in FIG. 26A, which provides a schematic of the illustrative embodiment of a communication scheme and a brief description of each Roman Numeral I, II, III, and IV is shown below. However, the specific communication scheme in no way limits the scope of the present disclosure unless otherwise indicated in the following claims and are for illustrative purposes only.

I. Outfall Smartcell—Onboard I/O for internal functions
Hard wired to the PLC and/or PAC:
5 digital inputs
14 digital outputs
5 analog inputs
1 analog output
III. Outfall Smartcell interconnecting to an end-user's pre-existing transmitter(s) and sensor(s) Numerous I/O capacity to accommodate multiple fluid analysis sensors. I/Os are hard wired to the PLC and/or PAC.

The end user's transmitter completes the sole purpose of one illustrative embodiment of a flow cell 110, as a major feature of the onboard automation is to ensure water always remains flowing (taking corrective actions if needed), so the point of the manufacturing process being analyzed remains online. Removing the time process instrumentation is in an offline configuration, not only saves money, but also creates additional layers of safety. Embedding Industry 4.0 as an option for other illustrative embodiments that may provide further value to the end user.

IV. Aggregate of process control instrumentation—Depiction showing the collection and transfer of process data from various process control instruments, to be analyzed by data analytics software, then receive commands to initiate changes to the manufacturing process. These commands can be returned directly back to the process control instrument (if it has the capacity to monitor and control process change), and/or sent directly to the process control device (such as a pump).

128 nodes (I/O) per DA & C (distribution automation and control)/PLC. Multiple DA & C's can be utilized simultaneously, allowing end-users to add more if needed.

Multiple communication protocols can be used by the end-user, such as RS-232, RS-485, Modbus RTU, Profibus, etc., may also be incorporated without limitation unless otherwise indicated in the fold lowing claims.

Figure 26B:
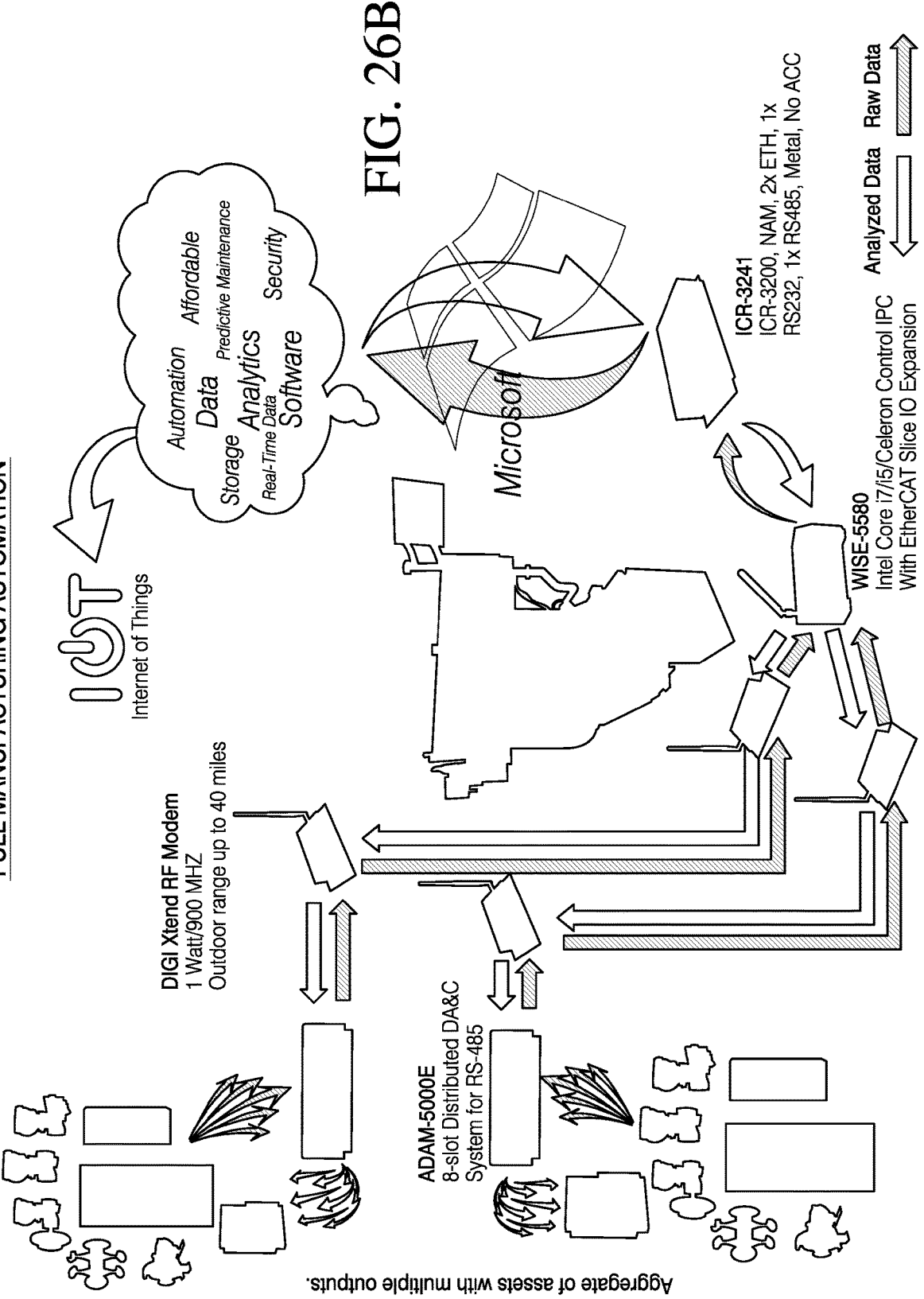

Another illustrative embodiment of a communication scheme for various components that may be implemented with a flow cell 110 is shown in FIG. 26B, which provides a schematic of the illustrative embodiment of a communication scheme. However, the specific communication scheme in no way limits the scope of the present disclosure unless otherwise indicated in the following claims and are for illustrative purposes only. Generally, such a communication scheme is not limited to use with a flow cell 110 as disclosed herein, but may be applicable across a wide range of industries and/or processes and may be used to monitor, control, and/or a wide range of components, processes, and/or equipment unless otherwise indicated in the following claims. Such a communication scheme may be employed in a manner that provides automation to a process by sending information directly to process control instruments and/or components, which may reduce the need for human involvement in the process.

For example, and without limitation unless otherwise indicated in the following claims, in one illustrative embodiment of a communication scheme, the communication scheme may be employed in multiple manufacturing settings, such as, but not limited to, the drinking water industry. In such an application, these facilities require multiple individual processes that must work together for a successful operation. The emergence of the multiple communication and automation technologies that lie within the Outfall Smartcell form a symbiotic relationship, allowing large amounts of data to be processed through data analytics software, and returned to the Outfall Smartcell and/or other component, at a high rate of speed. This computing power allows manufacturing facilities the ability to bring connectivity amongst all their individual machines, into a unified system, fully operated by artificial intelligence (AI). The Outfall Smartcell's ability to connect and allow for multiple data communication platforms to communicate with one another, supplemented by its computing capacity, has the ability to connect to, process, and manage, all process control devices (e.g., analyzers, pumps, pressure sensors, etc.), as well as chemical inventory. Additionally, in certain illustrative embodiments of a communication scheme according to the present disclosure, a flow cell 110 may not be required, and instead the proper data transmission components (such as those shown in FIG. 26B) may be in communication with other process components (e.g., welding robots, CNC machines, etc.) such that the scope of the present disclosure extends to other applications of the remote and/or automated feedback loop for controlling various processes, equipment, and/or parameters thereof without limitation unless otherwise indicated in the following claims.

Generally, the flow cell 110 may be comprised of a main chamber 120 having a base plate 130 engaged therewith on the bottom of the main chamber 120 and a cover 160 engaged therewith on an upper surface of the main chamber 120. The cover 160 may be sealed on the upper surface of the main chamber 120 with redundant gaskets, O-rings, and/or other sealing methods and/or apparatuses without limitation unless otherwise indicated in the following claims. It is contemplated that for most applications it may be advantageous to engage one or more sensors with the cover 160 (including but not limited to the sensors previously described herein above unless otherwise indicated in the following claims), wherein the sensors are in proximity to and/or in contact with a flow of sample fluid positioned within the interior portion of the main chamber 120 without limitation unless otherwise indicated in the following claims. In one illustrative embodiment the flow cell 110 is configured with an array of sensors, each monitoring a specific parameter within the body of sample fluid flowing through the trough.

Figure 20:
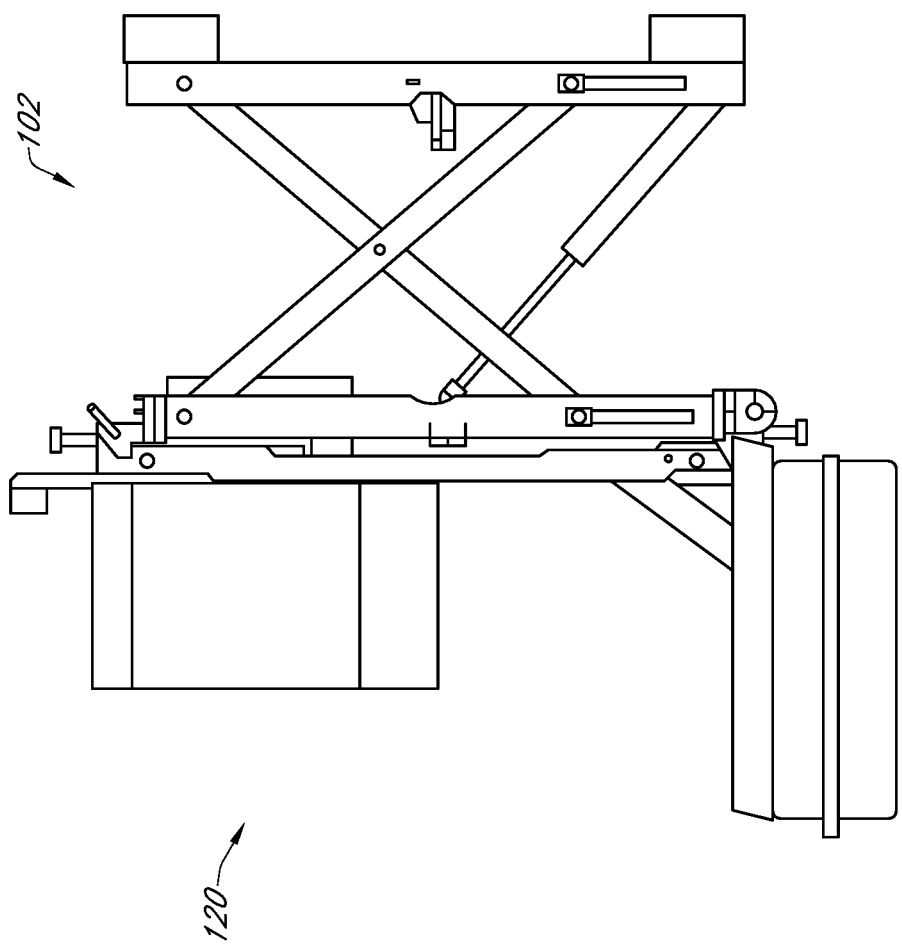
FIG. 20 right side view of an illustrative embodiment of a flow cell mount that may be used with various embodiments of a flow cell.

The flow cell 110 may be engaged with a mounting apparatus 102, as shown at least FIG. 20. As shown, an illustrative embodiment of a mounting apparatus 102 may be comprised of a scissor-type of linkage such that a user may adjust the distance between the flow cell 110 and a structural support (e.g., wall, stud, beam, etc.) with which the mounting apparatus 102 is engaged. It is contemplated that such a mounting apparatus 102 may allow a user to access the rear portion of the flow cell 110 in a relatively easy manner. The mounting apparatus 102 may also be configured with various leveling components to allow the user to level the flow cell 110 in at least two dimensions regardless of the structural support to which the mounting apparatus is engaged. Generally, any such mounting apparatus 102 that provides such functionality may be used without limitation unless otherwise indicated in the following claims, and certain applications may not require a mounting apparatus 102. The mounting apparatus 102 and flow cell 110 may further be configured such that the flow cell 110 may be disengaged from the mounting apparatus 102 with relative ease. A transparent panel 118 may be engaged with a front-facing portion of the main chamber 110 at an elevation between the base plate 130 and the cover 160. However, in other embodiments the transparent panel 118 may be omitted and/or differently configured without limitation unless otherwise indicated in the following claims.

A light system may be positioned adjacent the transparent panel 118 (which light system may be positioned in the cover 160) to allow for visual inspection of sample fluid flow (or wash fluid flow) through a portion of the main chamber 120 and/or base plate 130. In one illustrative embodiment a user may control the light system via a mobile device using a wireless connection (e.g., Bluetooth, 802.11 protocols, cellular connection, etc.). The light system may be configured as one or more LEDs that may be configured to emit light of a specific wavelength as dictated by the user, to vary based on a predetermined condition (e.g., a value of a specific fluid parameter, an operating condition of the flow cell 110, etc.). In an illustrative embodiment, the lighting system may be equipped with an onboard charging station to such that the lighting system may be operable at any time. Since in an illustrative embodiment the flow cell 110 and associated components may be powered by a 24V electrical power supply, a separate power converter may be utilized to provide a 12V electrical power supply to the lighting system, dropping 120V down to a 12V power supply.

Figure 16A:
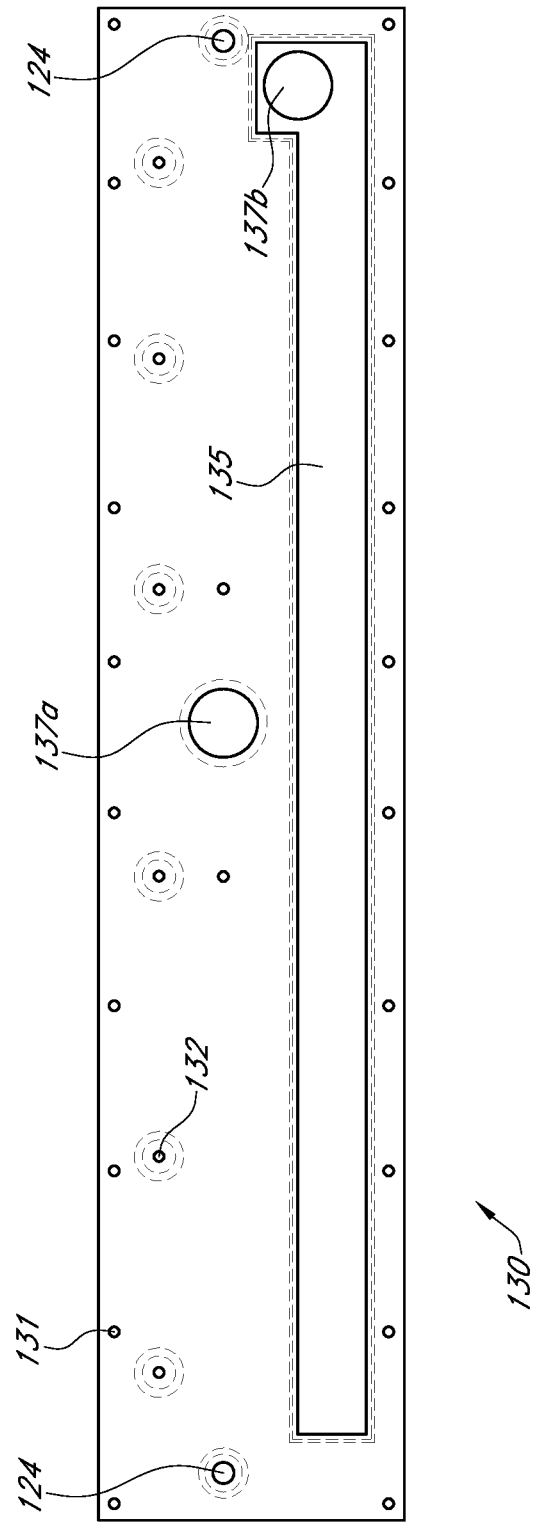
FIGS. 16A-16E provide various detailed views of an illustrative embodiment of a base plate that may be used with various embodiments of a flow cell.

Various views of an illustrative embodiment of a base plate 130 are shown in FIGS. 16A-16E, and illustrative dimensions of various features are shown therein, which dimensions may constitute a preferred embodiment of the base plate 130 for one or more applications thereof. However, the scope of the flow cell 110 and base plate 130 are not so limited unless otherwise indicated in the following claims. The illustrative embodiment of a base plate 130 may be used with the various embodiments of a flow cell 110 and may be specifically adapted for use with the flow cell 110 shown in FIG. 15. A top view of the base plate 130 is shown in FIG. 16A, wherein the upper edge of the drawing may be positioned toward the mounting apparatus 102 during use and the lower edge of the drawing may be positioned opposite the mounting apparatus 102 during use. Generally, unless otherwise indicated the term "front side" as used herein will refer to the surface of the flow cell 110 and/or component thereof opposite the mounting apparatus 102 during use, the term "rear side" as used herein will refer to the surface of the flow cell 110 and/or component thereof adjacent to the mounting apparatus 102 during use, the term "right side" as used herein will refer to the surface of the flow cell 110 and/or component thereof toward the right side thereof (i.e., right of center) from the vantage point of an observer viewing the front side of the flow cell 110 and/or component thereof, and the term "left side" as used herein will refer to the surface of the flow cell 110 and/or component thereof toward the left side thereof (i.e., left of center) from the vantage point of an observer viewing the front side of the flow cell 110 and/or component thereof.

Referring specifically to FIG. 16A (which provides a top view of an illustrative embodiment of a base plate 130), the illustrative embodiment shown therein includes a total of six base plate inlets 132 (one of which is marked with an "A" in FIG. 16A) evenly spaced along the length of the base plate 130. The dashed lines in FIG. 16A indicate an area that may be comprised as an optional seating groove for an O-ring or other sealing member without limitation unless otherwise indicated in the following claims. Sample fluid may flow into the base plate 130 from the sample fluid inlet line 111 through the base plate inlets 132 via a main inlet 133 (shown at least in FIG. 16E). The illustrative embodiment of the base plate 130 may also be formed with a plurality of mounting apertures 131 formed around the periphery of the base plate 130, wherein the mounting apertures 131 may cooperate with fasteners and corresponding receivers 126a (show at least in FIG. 19J) formed in the main chamber 120 to facilitate selective engagement and disengagement of the base plate 130 with the main chamber 120. Although some mounting apertures 131 may be positioned around the periphery of the base plate 130 for use with corresponding receivers 126a formed in the main chamber 120, it is contemplated that in illustrative embodiments one or more mounting apertures 131 and corresponding receivers 126a may be positioned inward with respect to the periphery of the base plate 130 and main chamber 120, respectively. It is contemplated that such inwardly positioned mounting apertures 131 and receivers 126a may serve to provide additional attachment points between the base plate 130 and main chamber 120, which may provide for a more even pressure distribution (which may in turn provide a more even compression on any seals, such as O-rings, so as to mitigate and/or eliminate leaks). Any suitable structure and/or method may be used to achieve such selective engagement and disengagement between or among various elements of the flow cell 110 without limitation unless otherwise indicated in the following claims. That is, the base plate 130 may be formed with a plurality of mounting apertures 131 positioned generally about the periphery of the base plate 130. Fasteners (not shown, but which may be configured as bolts, screws, etc. without limitation unless otherwise indicated in the following claims) may pass through each mounting aperture 131 and extend into a corresponding receiver 126a formed in a bottom surface periphery of the main chamber 120 to allow selective engagement between the base plate 130 and main chamber 120 at the bottom of the main chamber 120. Any suitable method and/or apparatus of engaging the base plate 130 with the main chamber 120 currently known or later conceived may be used without limitation unless otherwise indicated in the following claims (e.g., mechanical fasteners, chemical adhesives, combinations thereof, etc.). Additionally, in other embodiments of the flow cell 110, the base plate 130 and main chamber 120 may be formed as one integral unit, wherein such mounting apertures 131, receivers 126a, and fasteners are not required without limitation unless otherwise indicated in the following claims.

Illustrative fabrication methods and dimensions for features marked with letters A, B, C, D, P, F, G, and K are provided below, but are in no way limiting to the scope of the flow cell 110 and/or base plate 130 unless otherwise indicated in the following claims.

A: Sample ports inside dashed circle. Drilled to ¼" diameter and ½" depth to enter sample chamber (See base plate left side end view print). Dashed circles indicate O-ring seal placement—0.139 O-ring with a 0.437 ID, and a 0.687 OD at a depth of 0.124

B: 0.197" Drill Diameter. 20 places evenly spaced around perimeter of plate. Approximately 3" apart.

C: 1%4" Drill Diameter. Dotted circle is for an O-ring seal placement—0.139 O-ring with a 1.100 ID, and a 1.386 OD at a depth of 0.124

D: 1%4" Drill Diameter.

P: Area within "P" is milled to a 1½" depth. Corners are to be radiused. IMPORTANT When rounding corner, do not have the high point of the arch pass the line by drain hole (see red arrow) due to colliding into water jacket (G).

F: Area within "F" is milled to a 1⅜" depth, with a gradual decline down to P and D, with an ending depth of 1½".

G: Drilled ½". Dotted circle (O-ring seal)—0.139 O-ring with a 0.480 ID, and a 0.766 OD at a depth of 0.124.

K. 0.171" Drill through diameter for #10-24 bolt.

Other numbers, spacings, configurations, dimensions, etc. of base plate inlets 132, main inlet 133, and/or other features of the base plate 130 shown in FIGS. 16A-16E and/or described herein may be used without departing from the spirit and scope of the present disclosure unless otherwise indicated in the following claims.

Figure 16B:
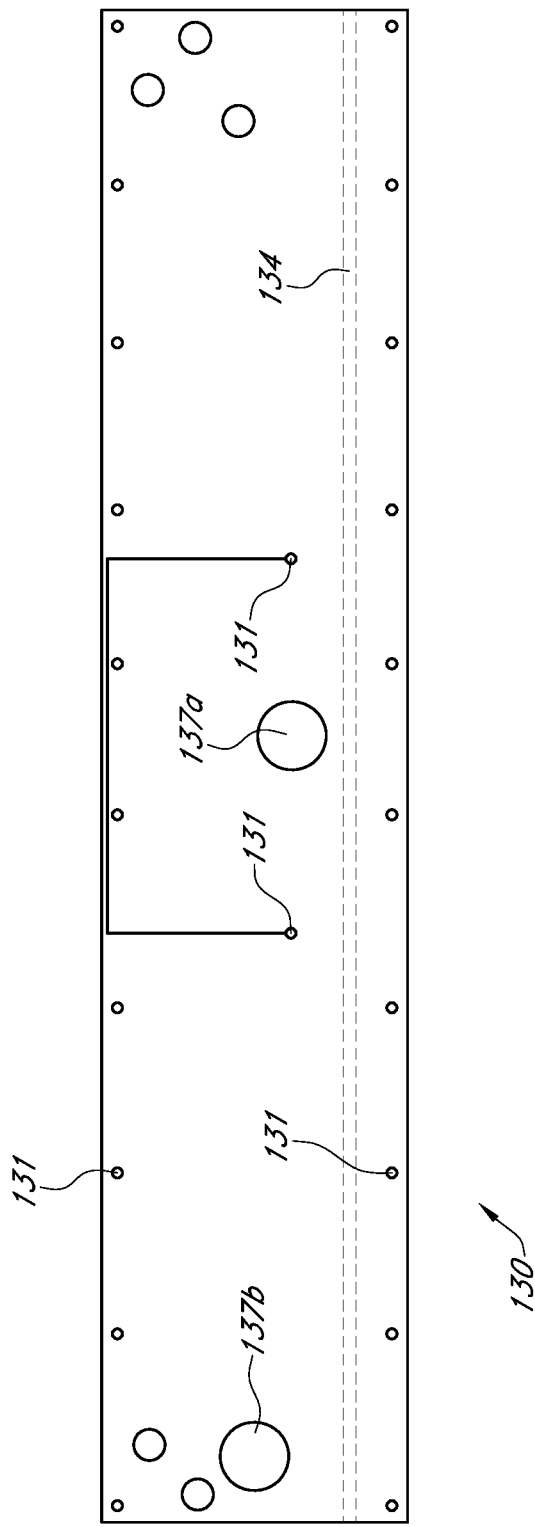

Referring now to FIG. 16B, which provides a bottom view of the illustrative embodiment of a base plate 130 shown in FIG. 16A, this embodiment may be formed with a secondary drain passage 137a and a primary drain passage 137b, both of which are also shown in FIG. 16A. Illustrative fabrication methods and dimensions for features marked with letters D, B, G, M, L, and K are provided below, but are in no way limiting to the scope of the flow cell 110 and/or base plate 130 unless otherwise indicated in the following claims.

D: Tap for 1" NPT Thread
B: Counterbore for #10-24 SCHS.
G: Drill for ½" NTP at a depth of ¾", then tap (IMPORTANT: NOT TO OPEN UP THE ENTIRE HOLE WITH TAP DRILL).
M: Drill and tap for ½" NTP at a depth of 1¾". Hole will merge into the end points of the 28"×½" bored hole (letter R shown in FIG. 16C).
L: Drill ½" diameter hole at a depth of 1", then drill for ½" NTP at a depth of ¾", then tap. (IMPORTANT: NOT TO OPEN UP THE ENTIRE HOLE WITH TAP DRILL).
K: Counterbore for SCHS utilizing #10-24.

Figure 16C:
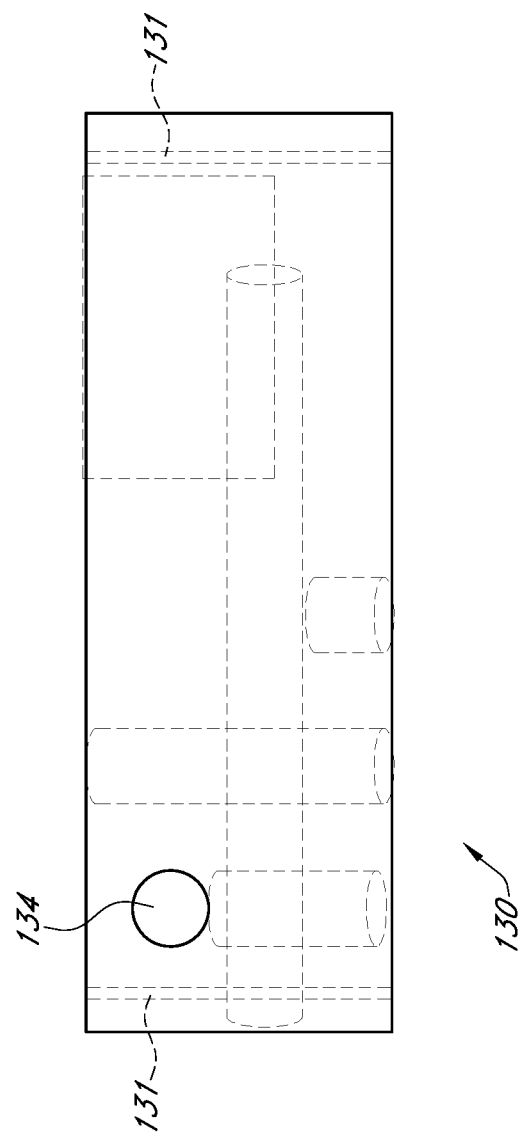

Referring now to FIG. 16C, which provides a left end view of the illustrative embodiment of a base plate 130 shown in FIGS. 16A & 16B, the illustrative embodiment of a base plate 130 may be formed with various internal passages and/or bores to accommodate the various functionalities/benefits as described herein, or which are inherently present, wherein dashed lines represent hidden surfaces/features. Illustrative fabrication methods and dimensions for the feature marked with letter R are provided below but are in no way limiting to the scope of the flow cell 110 and/or base plate 130 unless otherwise indicated in the following claims.

R: ½" Diameter. Drilled from both sides of plate (right side shown in FIG. 16D), then tap both sides ⅝"—18 plate hole to accommodate for a flat faced screw NPT socket plug with O-ring seal.

Figure 16D:
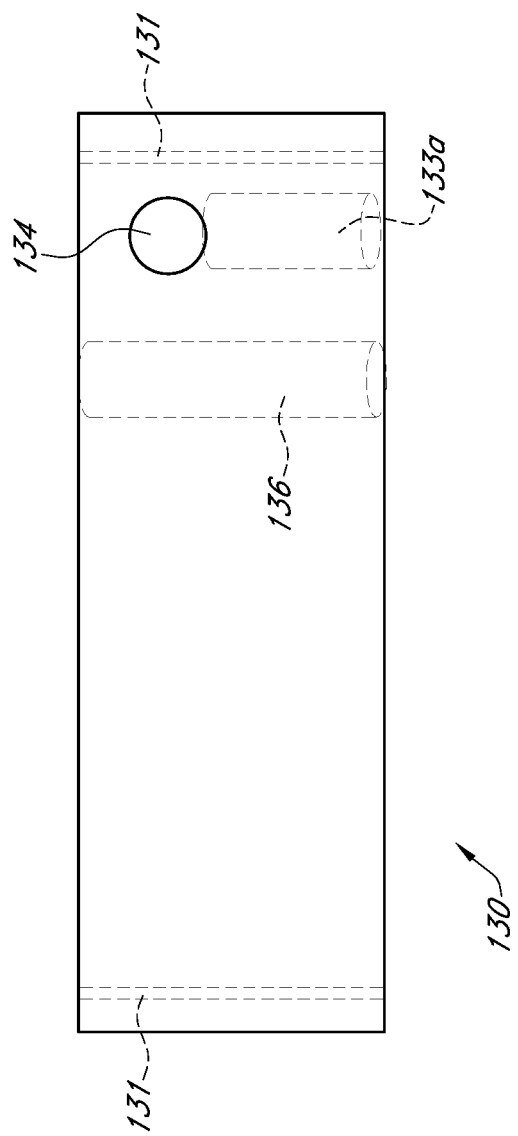
Figure 16E:
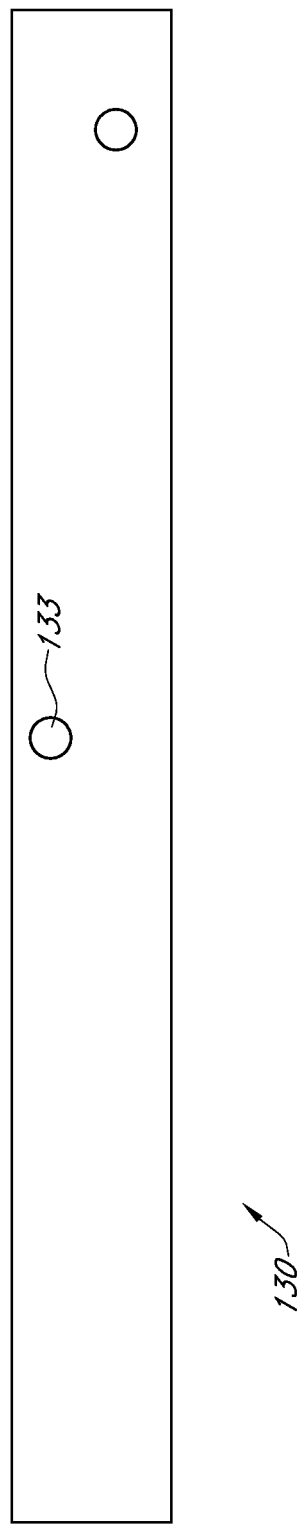

Referring now to FIGS. 16D & 16E, a right end view and rear side view, respectively, of the illustrative embodiment of a base plate 130 are shown therein. Generally, the feature marked "M" may provide an inlet to an interior portion of the base plate 130 for wash fluid and serve as a main wash fluid inlet 133*a*, which and may intersect the feature marked "R." Feature "R" may be configured to extend across a portion of the length of the base plate 130 and serve as the sample fluid channel 134. The feature marked "G" may be configured as a base plate cleaning nozzle passage 136 and serve to communicate wash fluid to the second cleaning nozzle 150 (engaged adjacent the second end wall 121*b*). The feature marked "S" on FIG. 16E may be configured as a fluid pathway to intersect with feature "L" (shown at least in FIG. 16C, and which feature "L" exits on the far-left end of the waste reservoir 135), wherein the exterior terminus of the fluid pathway may be plugged such that wash fluid may be provided to the waste reservoir 135 via a wash fluid supply in fluid communication with feature "L" without limitation unless otherwise indicated in the following claims. Illustrative fabrication methods and dimensions for features marked with letters S and T are provided below but are in no way limiting to the scope of the flow cell 110 and/or base plate 130 unless otherwise indicated in the following claims.

S: Drill ½" at a depth of 4". Then tap to ⅝"—18 plate hole to accommodate for a flat faced screw NPT socket plug with O-ring seal.
T: Drill and tap for ½" NTP at a depth of 1". Hole will merge into the center point of the 28"×½" bored hole (R).

Various views of an illustrative embodiment of a cover 160 (or "top plate" as indicated in some drawings herein) are shown in FIGS. 17A-17D, and illustrative dimensions of various features are shown therein, which dimensions may constitute a preferred embodiment of the cover 160 for one or more applications thereof. However, the scope of the flow cell 110 and cover 160 are not so limited unless otherwise indicated in the following claims. The cover 160 may be formed with one or more cover mounting apertures 161 formed around the periphery of the cover 160, wherein the cover mounting apertures 161 may cooperate with fasteners and corresponding receivers formed in the main chamber 120 to facilitate selective engagement and disengagement of the cover 160 with the main chamber 120. Again, any suitable structure and/or method may be used to achieve such selective engagement and disengagement between or among various elements of the flow cell 110 without limitation unless otherwise indicated in the following claims.

Figure 17A:
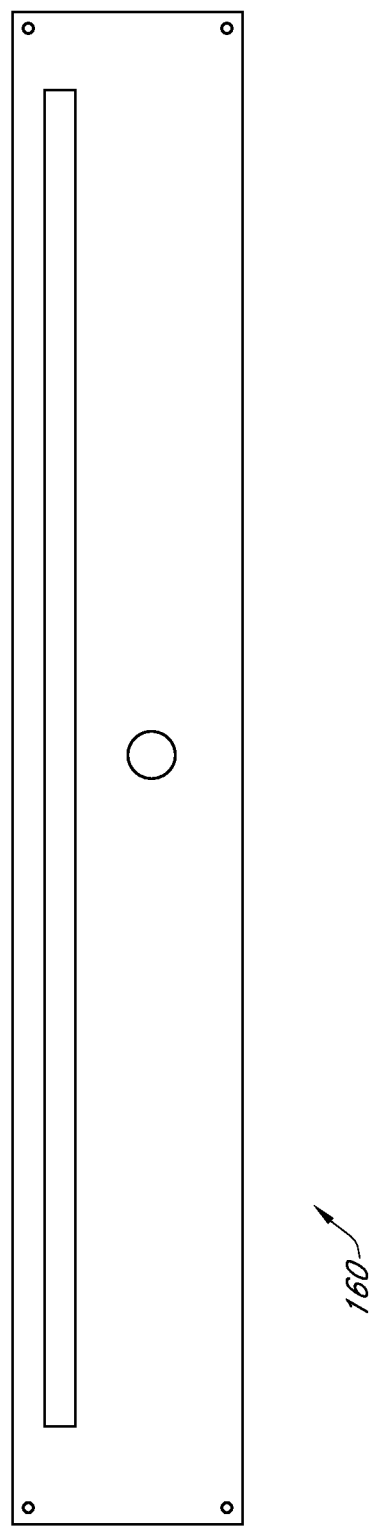
FIGS. 17A-D provide various detailed views of an illustrative embodiment of a cover that may be used with various embodiments of a flow cell.
Figure 17B:
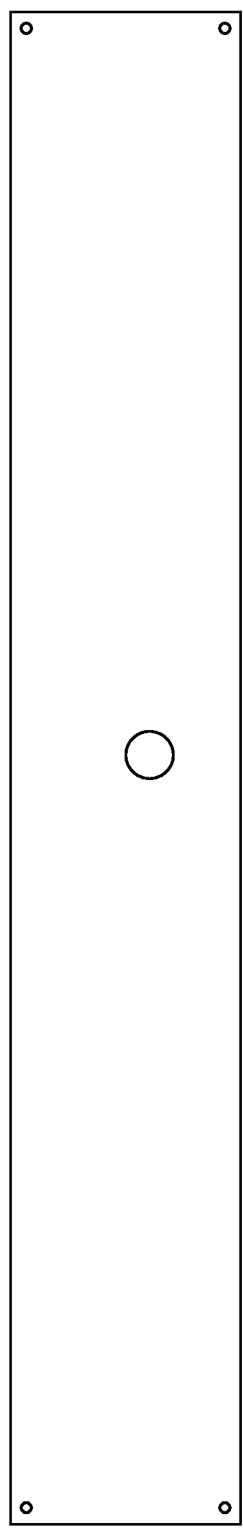
Figure 17C:
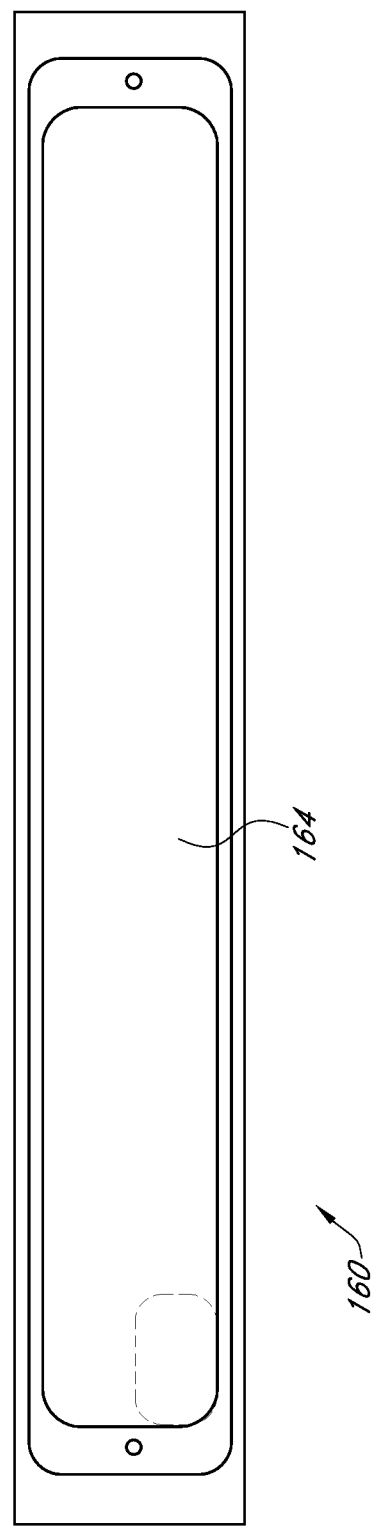
Figure 17D:
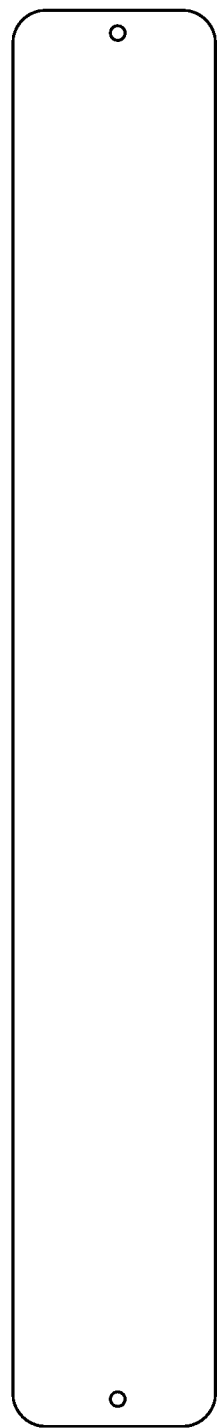

A bottom view of the illustrative embodiment of a cover 160 is shown in FIG. 17A, a top view in FIG. 17B, a right side end view in FIG. 17C, and a view of a cap 164 that may be engaged with the right end of the cover 160 is shown in FIG. 17D. Illustrative fabrication methods and dimensions for features marked with letters U, V, Q, Z, X, Y, and W are provided below but are in no way limiting to the scope of the flow cell 110, cover 160, and/or cap 164 unless otherwise indicated in the following claims.

U: 0.221" Drill Diameter, equally spaced at ¼" from the corners on all 4 corner locations.
V: Milled ⅜" deep
Q: Drill and tap for a M30×1.5 mm thread for sensor shown below.
Z: Milled to 1¾" depth. Keep all radius' ⅛".
X: After A is milled out, then mill B at a depth of 2". This will connect the channel groove on the bottom side operation.
Y: Drill and tap for 8-32 at a depth of ½" using a bottom tap.
W: Shaded perimeter is milled to a ⅛" depth.

A cap 164 that may be positioned on the right end of the cover 160 is shown in FIG. 17D. In one illustrative embodiment thereof the cap 164 may be constructed of Delrin, but the scope of the present disclosure is not so limited unless otherwise indicated in the following claims.

Y: Drill through to 0.190 diameter.
1: Keep all radius ⅛"
2: Thickness of cap is ¼".

Figure 18B:
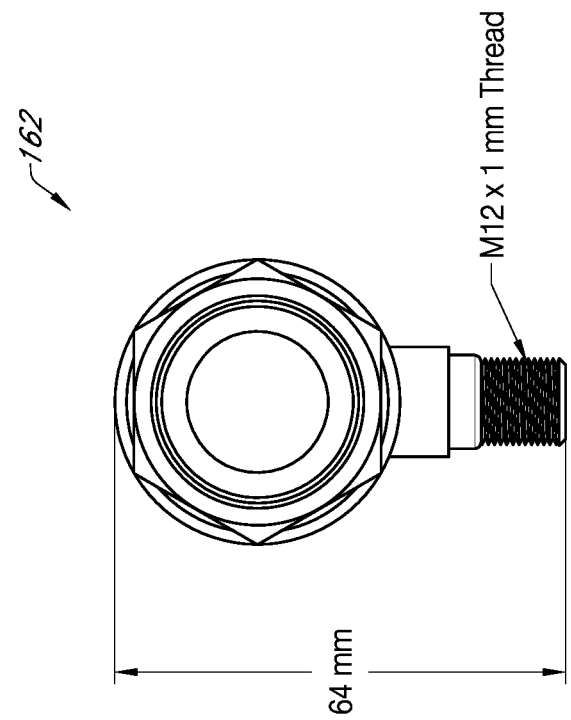
FIGS. 18A & 18B provide various detailed views of a sample level sensor housing that may be used with various embodiments of a cover.
Figure 18A:
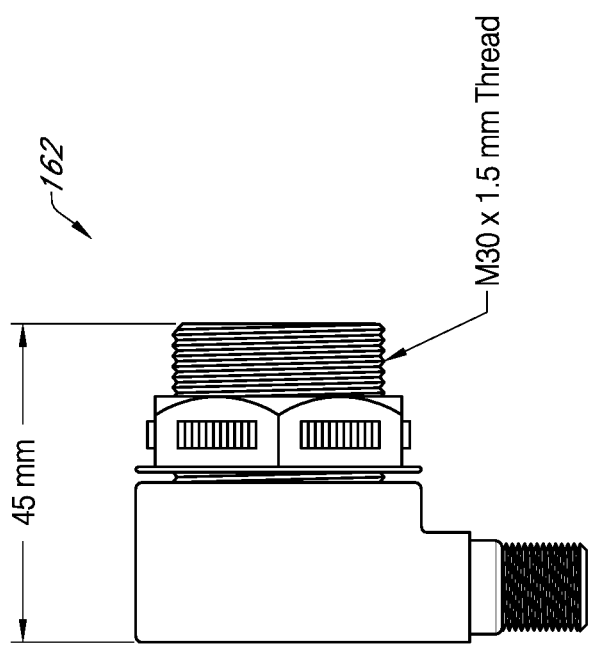

Referring now to FIGS. 18A & 18B, therein are provided side view and a front view, respectively, of an illustrative embodiment of a sensor 162 that may be engaged with the illustrative embodiment of a cover 160 at the position denoted with the letter "Q" in FIGS. 17A & 17B. However, differently positioned and/or configured sensors 162 may be used with other embodiments of the flow cell 110, 160, and/or cap 164 without limitation unless otherwise indicated in the following claims.

Various views of an illustrative embodiment of a main chamber 120 (or "aluminum block" as indicated in some drawings herein) and/or elements thereof are shown in FIGS. 19A-19J, and illustrative dimensions of various features are shown therein, which dimensions may constitute a preferred embodiment of the main chamber 120 for one or more applications thereof. However, the scope of the flow cell 110 and main chamber 120 are not so limited unless otherwise indicated in the following claims.

Illustrative fabrication methods and dimensions for various features shown in FIGS. 19A-19D marked with the letters A, Z, and/or shown in those drawings are provided below but are in no way limiting to the scope of the flow cell 110 and/or main chamber 120 unless otherwise indicated in the following claims.

Z: 0.203" Drilled Diameter, at a depth of ⅜", tapped for ¼-20, for all four corner locations.

A: Exterior vent hole (element 127bb) drilled ¼" at a depth of 1" to intersect with the ¼" vertical shaft originating from the baseplate well drain. This hole may be capped with a screen vent.

Both holes drilled to a ⁷⁄₁₆" diameter through to the other side (inside well).

Both ends (left and right side) tapped to ¼" NPS through to the other side (inside well).

Dotted tube represents the left and right-side water jackets intersecting with each sprayer.

Drill ⁹⁄₁₆" at a depth of 1" on both sides.

Tap both sides ⅜" NPS at a depth of ⅞"

⅜" NPS plate hole to accommodate for a flat faced screw NPS socket plug with O-ring seal.

The main chamber 120 may be configured with a receiver that is sized and shaped to receive an edge of the cover 160 (described in further detail below) such that the edge of the cover 160 may seat within the receiver, wherein the cover 160 may then be and selectively secured therein when the cover 160 is disengaged from the top side of the main chamber 120.

Figure 19A:
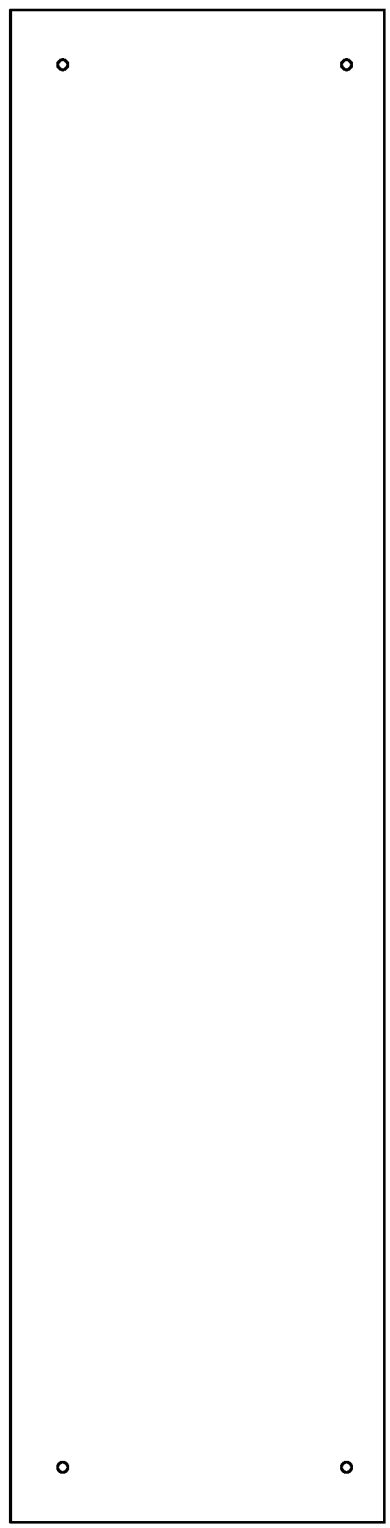
FIGS. 19A-19J provide various detailed views of an illustrative embodiment of a main chamber that may be used with various embodiments of a flow cell.
Figure 19C:
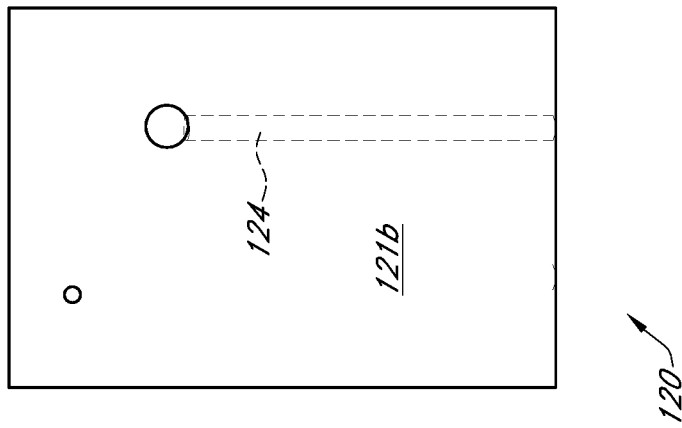
Figure 19B:
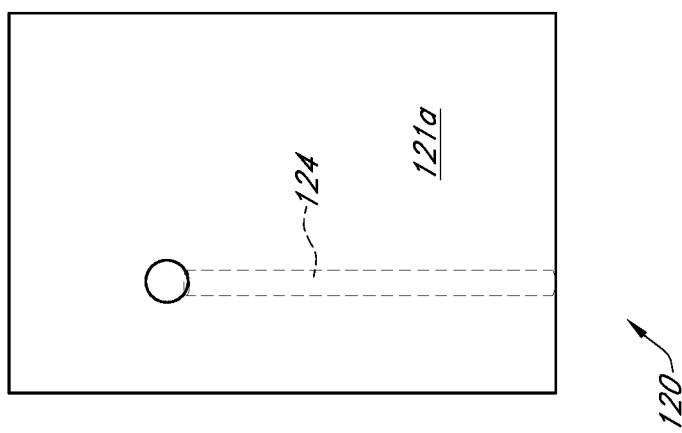
Figure 19D:
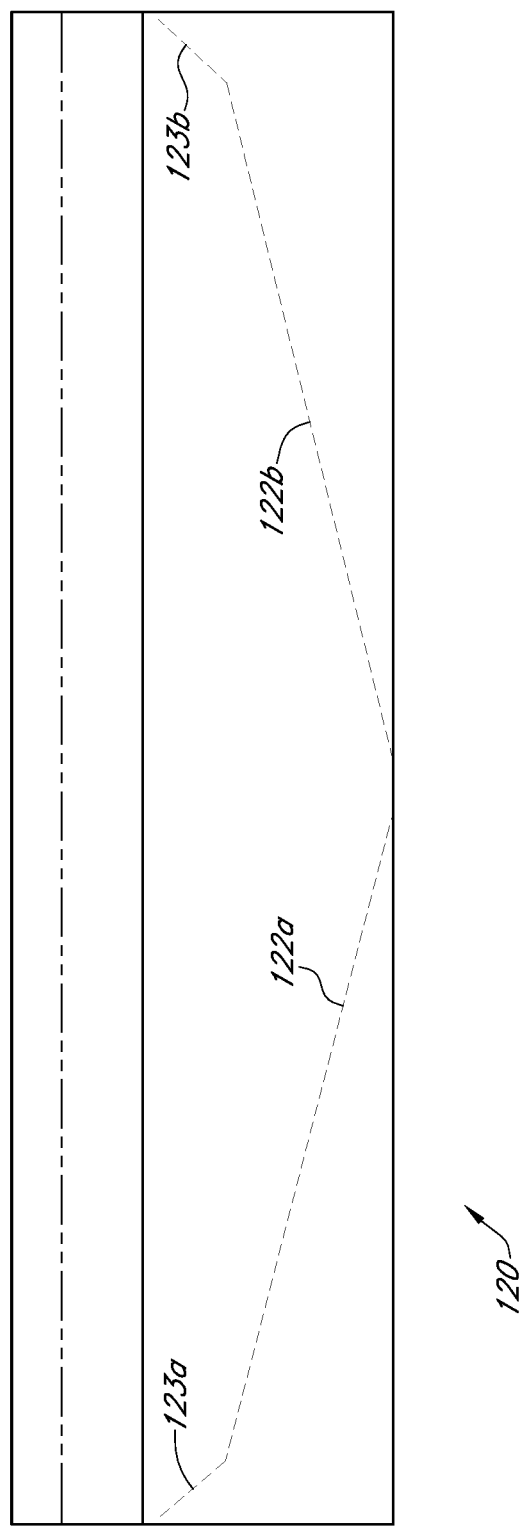

A rear view of the illustrative embodiment of the main chamber is shown in FIG. 19A, and right and left side end views thereof are shown in FIGS. 19B & 19C, respectively. Referring specifically to FIGS. 19D & 19H, which provide a front views of an illustrative embodiment of the main chamber 120, the main chamber 120 may be configured such that a first angled portion 123a (extending from the first end wall 121a) and first ramp 122a are symmetrical with respect to a second angled portion 123b (extending from the second end wall 121b) and second ramp 122b about the right and left ends of the main chamber 120. In the illustrative embodiment, the first and second angled portions 123a, 123b may be angled at 45 degrees from the vertical and the first and second ramps 122a, 122b may be angled at 15 degrees from the horizontal. In the illustrative embodiment, the first and second ramps 122a, 122b may terminate adjacent the center of the main chamber 120 at a secondary drain 127. However, the optimal configuration of these features may depend at least upon the type and/or configuration of cleaning nozzles 140, 150 utilized for the specific flow cell 110. Accordingly, other angles, lengths, configurations, dimensions, etc. of the first and second angled portions 123a, 123b and/or first and second ramps 122a, 122b may be used with other embodiments of the main chamber 120 (and may be preferred embodiments for different applications) without limitation unless otherwise indicated in the following claims.

Figure 19E:
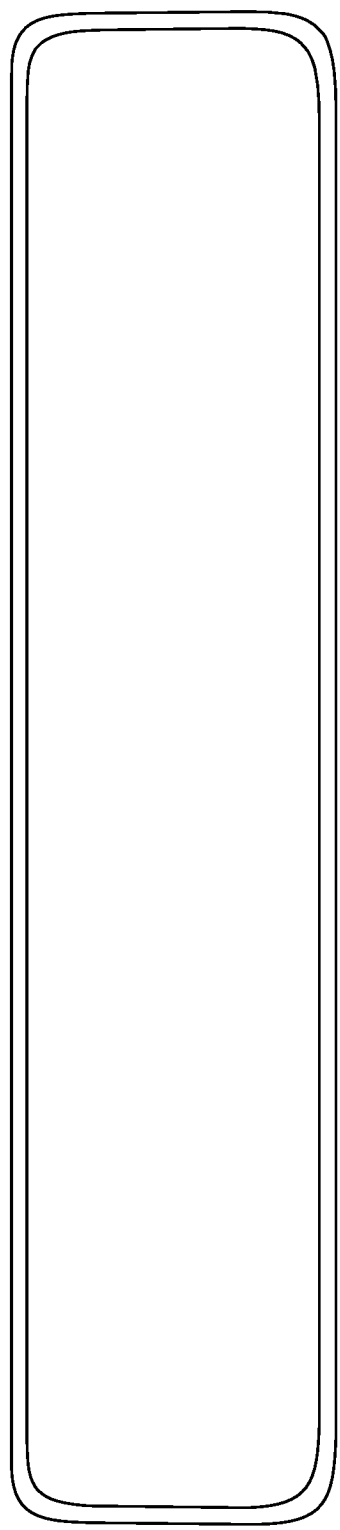
Figure 19F:
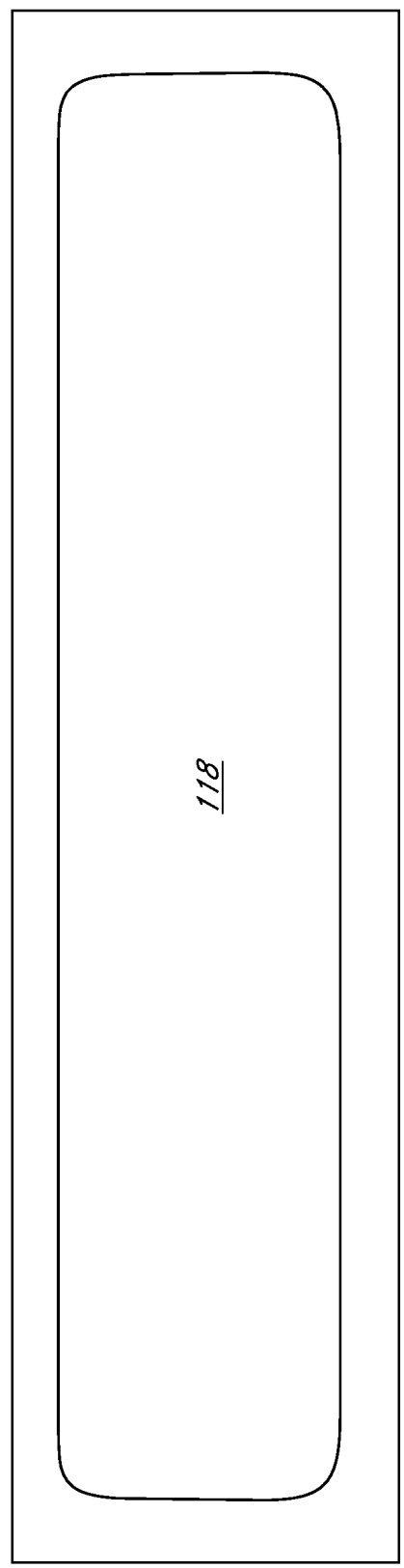

Referring now to FIG. 19E, a front view of a transparent panel 118 that may be engaged with the front surface of the illustrative embodiment of a main chamber 120 is shown therein, and a front view of the main chamber 120 with the transparent panel 118 engaged therewith is shown in FIG. 19F. It is contemplated that a transparent panel 118 may provide another inspection point for a user/operator of the flow cell 110 and allow visual inspection of numerous functions and/or features thereof, which may allow a user to mitigate and/or prevent errors, inaccurate readings, and/or various other problems or abnormalities that may be undesirable without limitation unless otherwise indicated in the following claims. The transparent panel 118 may be engaged with the main chamber 120 to form a hermetic seal therebetween, which may be accomplished via a seal (which may be an O-ring having a width of 0.139 inches and a depth of 0.120 inches) positioned around the periphery of the transparent panel 118. However, any suitable method and/or structure for adequately sealing the interface between the main chamber 120 and transparent panel 118 may be used without limitation unless otherwise indicated in the following claims.

Figure 19G:
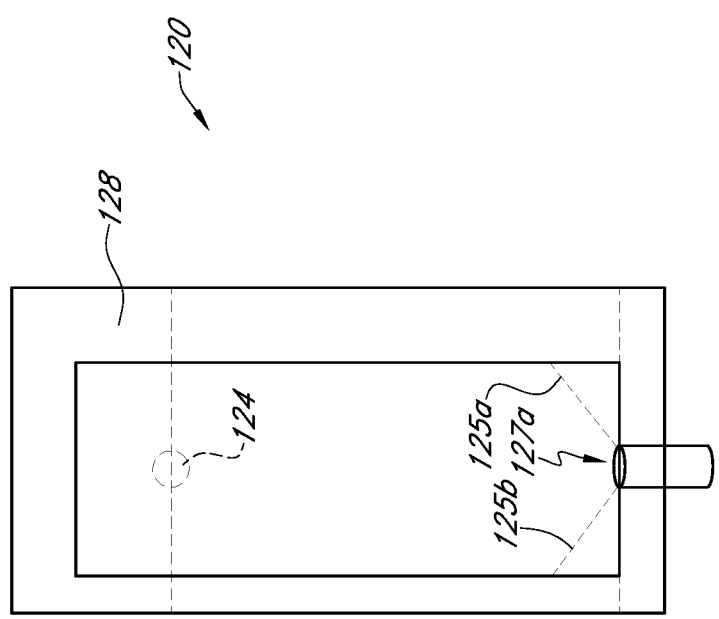
Figure 19H:
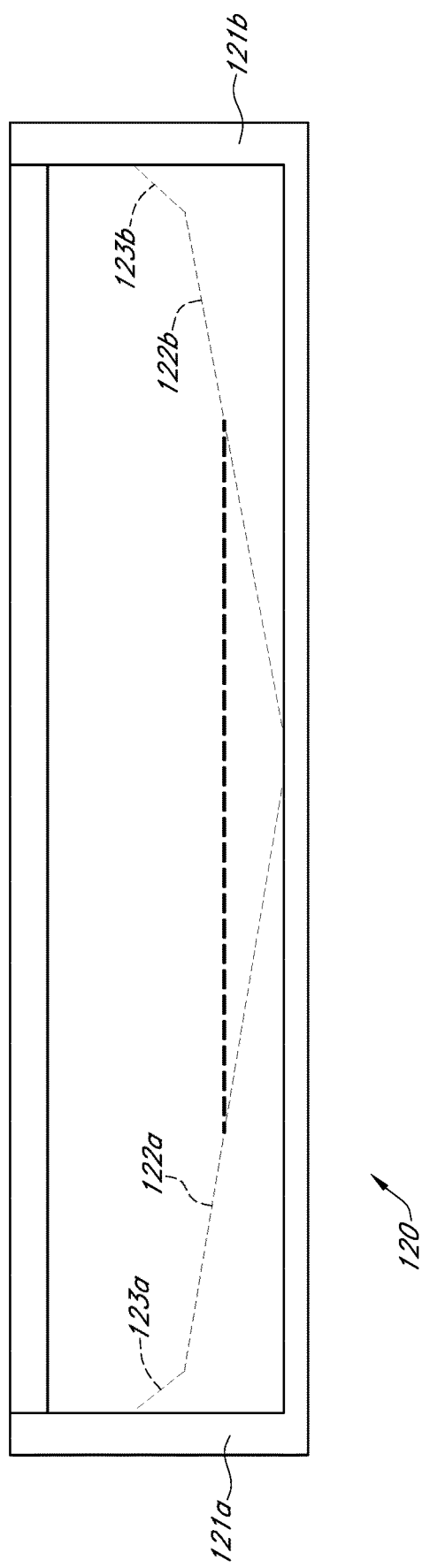

Another left side end view of the illustrative embodiment of a main chamber 120 is shown in FIG. 19G and another front view thereof is shown in FIG. 19H. Referring specifically to FIG. 19G, the front and rear walls adjacent the second drain 127a may be angled at 45 degrees from the vertical to facilitate fluid flow out of the main chamber 120 and through the second drain 127a via gravity. However, other angles and/or configurations may be used without limitation unless otherwise indicated in the following claims.

Figure 19I:
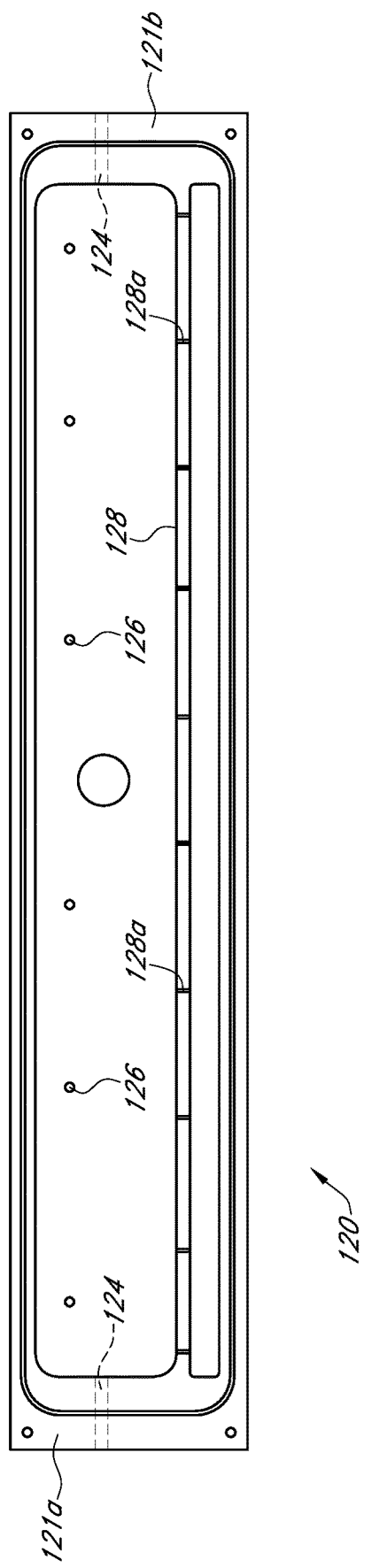
Figure 19J:
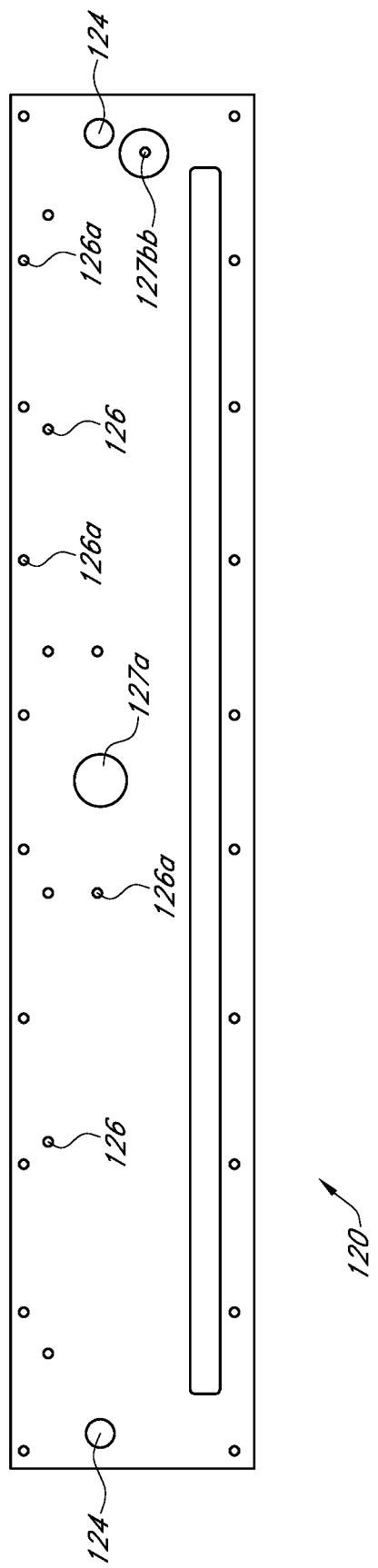

Referring now specifically to FIGS. 19I & 19J, which provide a top and bottom view, respectively, of the illustrative embodiment of a main chamber 120 without the various angled surfaces shown for purposes of clarity, the main chamber 120 may include a secondary drain 127a centered between the first end wall 121a and second end wall 121b. Generally, but without limitation unless otherwise indicated in the following claims, the interior portion of the illustrative embodiment of the main chamber 120 shown in FIGS. 19A-19J may be configured in a manner similar to the main chamber 20 previously described above with respect to FIGS. 1-14. The front edge of the main chamber 120 (which may constitute a weir) may be formed with a front wall 128 having one or more fluid control guides 128a positioned on a top edge thereof, which in the illustrative embodiment of the flow cell 110 may be configured as slots formed in the upper surface of the front wall 128 of the main chamber 120. As shown at least in FIG. 24E, in an illustrative embodiment of a main chamber 120, the interior surfaces of a front wall 128 and rear wall, the front-interior wall angled portion 125a and back-interior wall angled portion 125b, may be angled toward a secondary drain 127a. However, other configurations of the main chamber 120 may be used without limitation unless otherwise indicated in the following claims.

As fluid fills the main chamber (either from a cleaning nozzle 140, 150, sample fluid inlet port 126, etc.), it may rise to the fluid control guide(s) 128a and then fall down the front surface of the front wall 128 (e.g., between the front wall of the main chamber 120 and the transparent panel 118) and into the waste reservoir 135, and from the waste reservoir 135 to the primary drain passage 137b and/or primary drain 127b. The illustrative embodiment of the flow cell 110 may be configured with six equally spaced fluid control guides 128a along the length of the front wall 128 (i.e., the dimension from the first end wall 121a to the second end wall 121b), but the optimal configuration of the fluid control guides 128a may vary from one application of the flow cell 110 to the next. Accordingly, any suitable number, configuration, spacing, dimensions, etc. of fluid control guides 128a may be used without limitation unless otherwise indicated in the following claims. The main chamber 120 and various components thereof may be configured to provide a specific residence volume and level of sample fluid for a wide variety of residence times of sample fluid and/or flow rates of sample fluid.

Figure 21A:
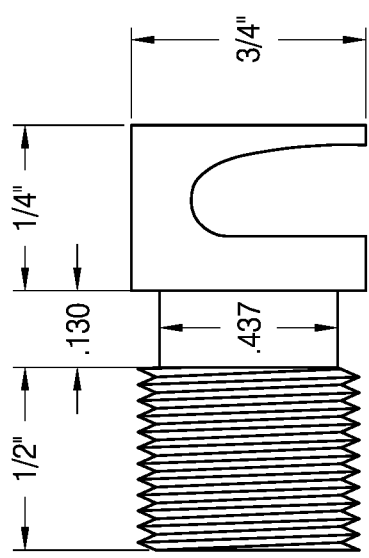
FIGS. 21A-21C provide various views of a cleaning nozzle that may be used with various embodiments of a flow cell.
Figure 21B:
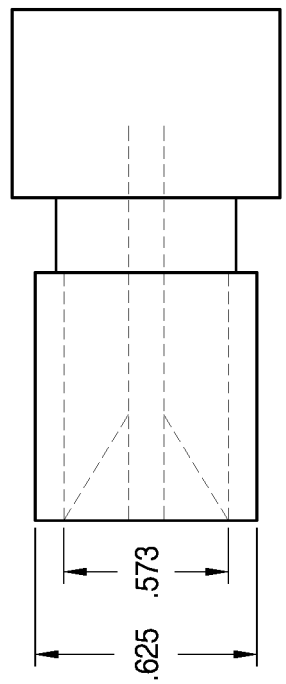
Figure 21C:
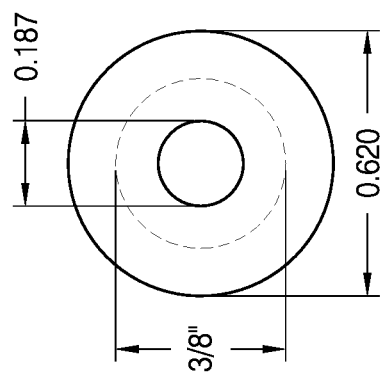
Figure 22:
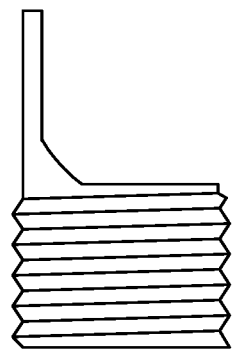
FIG. 22 provides a side view of an illustrative embodiment of a directional flow guide plug that may be used with various embodiments of a flow cell.
Figure 23A:
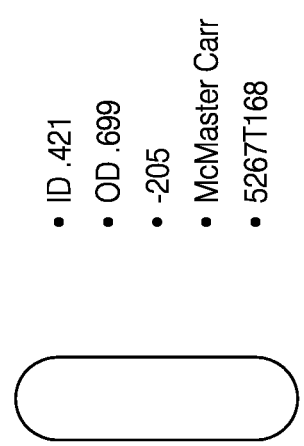
FIG. 23A provides a side view of an illustrative embodiment of an O-ring that may be used with various embodiments of a spray nozzle or directional flow guide plug.
Figure 23B:
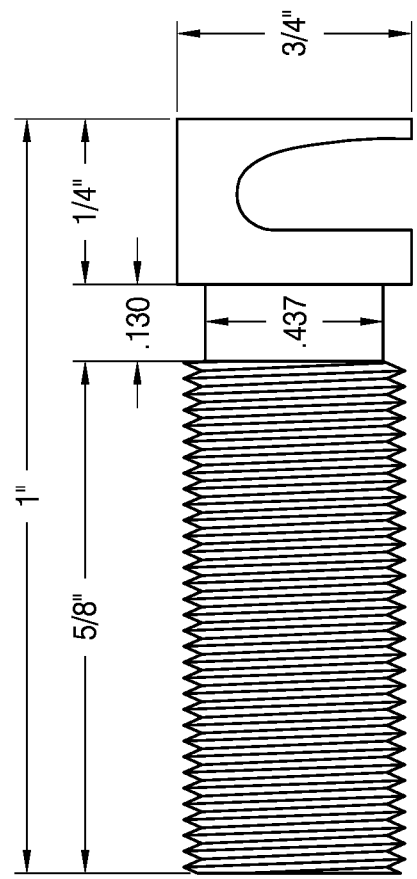
FIG. 23B provides a side view of another embodiment of a cleaning nozzle that may be used with various embodiments of a flow cell.

Referring now to FIGS. 21A-21C, therein are provided two side views and an end view, respectively, of an illustrative embodiment of a first or second cleaning nozzle 140, 150 that may be used with the illustrative embodiment of a flow cell 110. A side view of an illustrative embodiment of a directional flow guide plug is shown in FIG. 22 and a side view of an illustrative embodiment of an O-ring is shown in FIG. 23. However, differently positioned and/or configured cleaning nozzles 140, 150, directional flow plugs, and/or O-rings may be used with other embodiments of the flow cell 110 and/or cap main chamber 120 without limitation unless otherwise indicated in the following claims.

Illustrative Sample Fluid and Wash Fluid Flows

Referring generally now to FIGS. 24A-24F, various views of an illustrative embodiment of a flow cell 110 and/or portions thereof are shown. Additionally, FIGS. 24A-24F provide an illustrative method of sample fluid flow into, through, and from the illustrative embodiment of a flow cell 110, wherein various arrows are used to show various paths the sample fluid may take. Generally, the flow cell 110 and associated instrumentation, sensors, fluid handling components (e.g., valves, pumps, switches, etc.) may be controlled via a programmable logic controller (PLC) and/or programmable automation controller (PAC). The PLC and/or PAC may be configured to control/monitor one or more components positioned on, within, and/or local to the flow cell 110 in addition to one or more components that may be remote with respect to the flow cell 110. A user may provide the necessary logic, desired parameters, and/or rules, etc. to the PLC and/or PAC via a human-machine interface (HMI) that may be a component of the flow cell 110. In one illustrative embodiment, the HMI may be configured as a fold-out touch screen engaged with a side of the main chamber 120 without limitation unless otherwise indicated in the following claims.

Figure 24A:
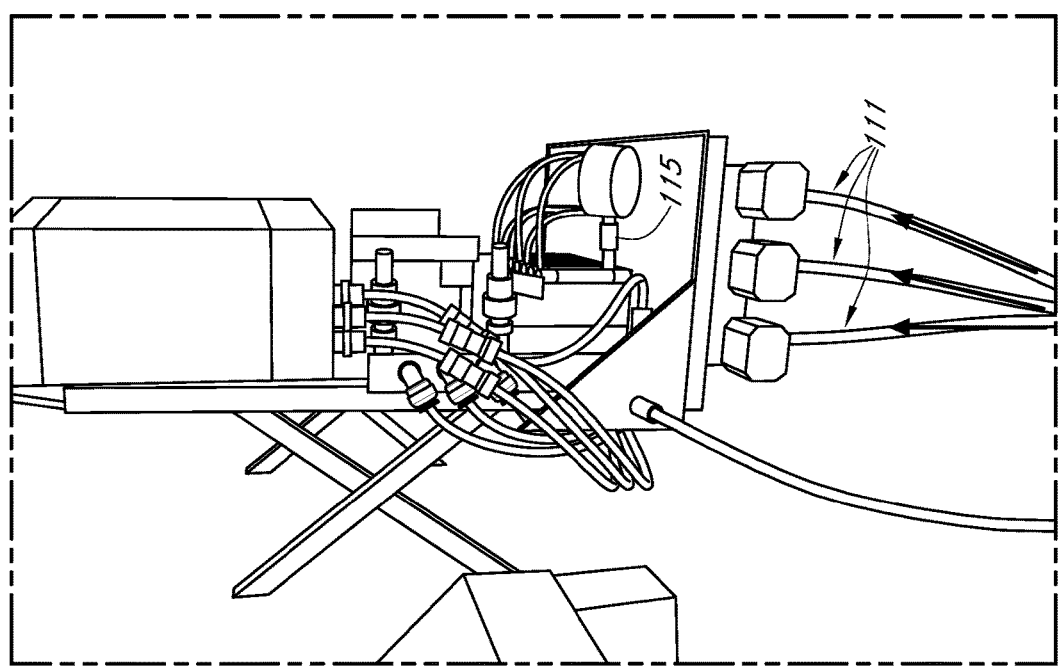
FIGS. 24A-24F provide various views of an illustrative embodiment of a flow cell highlighting a pathway for a sample fluid flow into, through, and out of the flow cell.

With specific reference to FIG. 24A, sample fluid may enter the flow cell 110 through a sample fluid line. In an illustrative embodiment the sample fluid line may be configured with a sample sequencer comprised of three separate sample fluid inlet lines 111 and three ball valves 112, but the sample fluid inlet to the flow cell 110 may be differently configured in other embodiments of the flow cell 110 without limitation unless otherwise indicated in the following claims (e.g., more or fewer sample fluid inlet lines 111, valves 112, etc.; differently positioned and/or configured sample fluid inlet lines 111, valves 112, etc.). A sample sequencer so configured may allow a single flow cell 110 to receive sample fluid from more than one source, and/or it may provide a redundant sample fluid inlet to the flow cell 110 in the event of a blockage or obstruction of a given sample fluid inlet line 111.

Figure 24B:
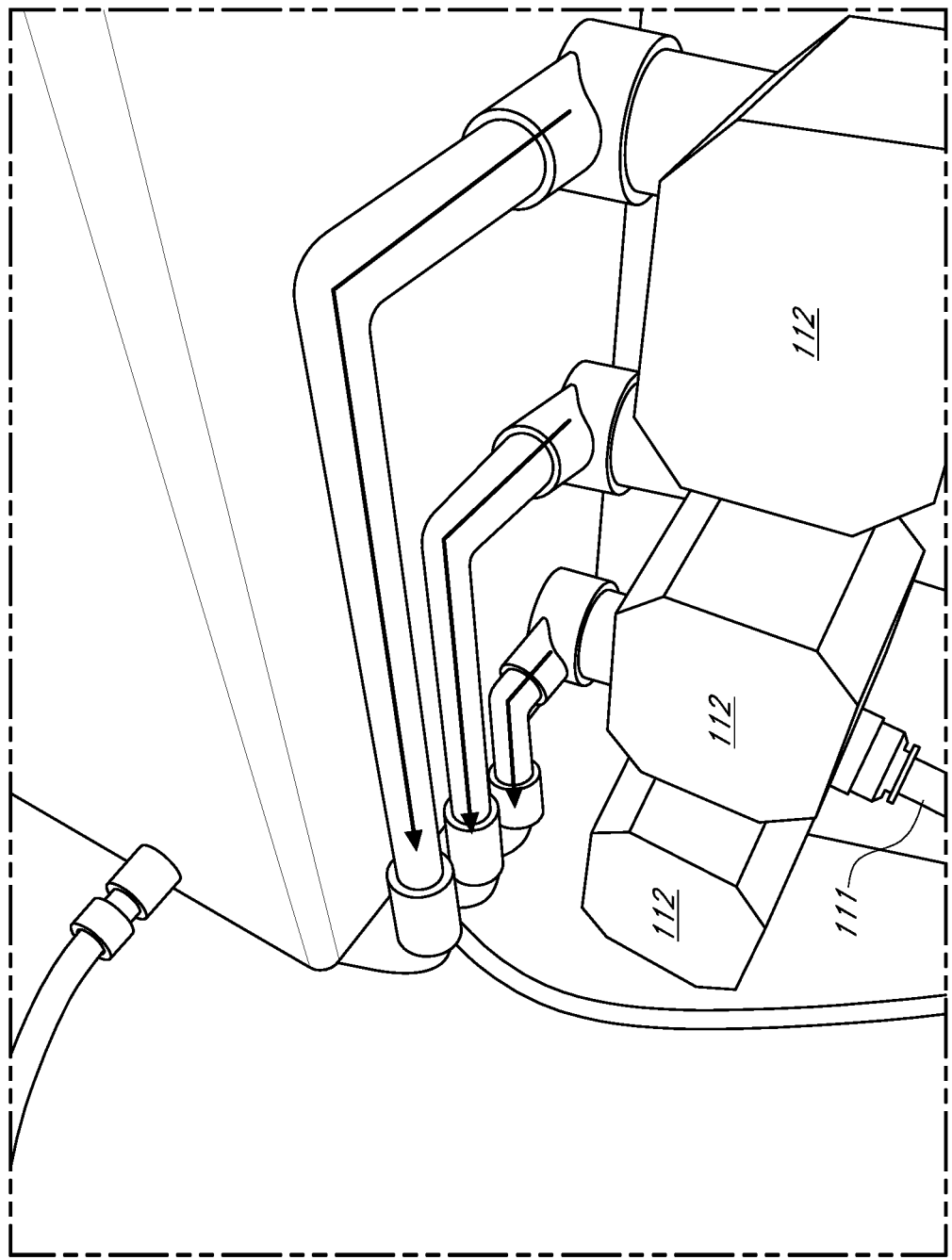
Figure 24C:
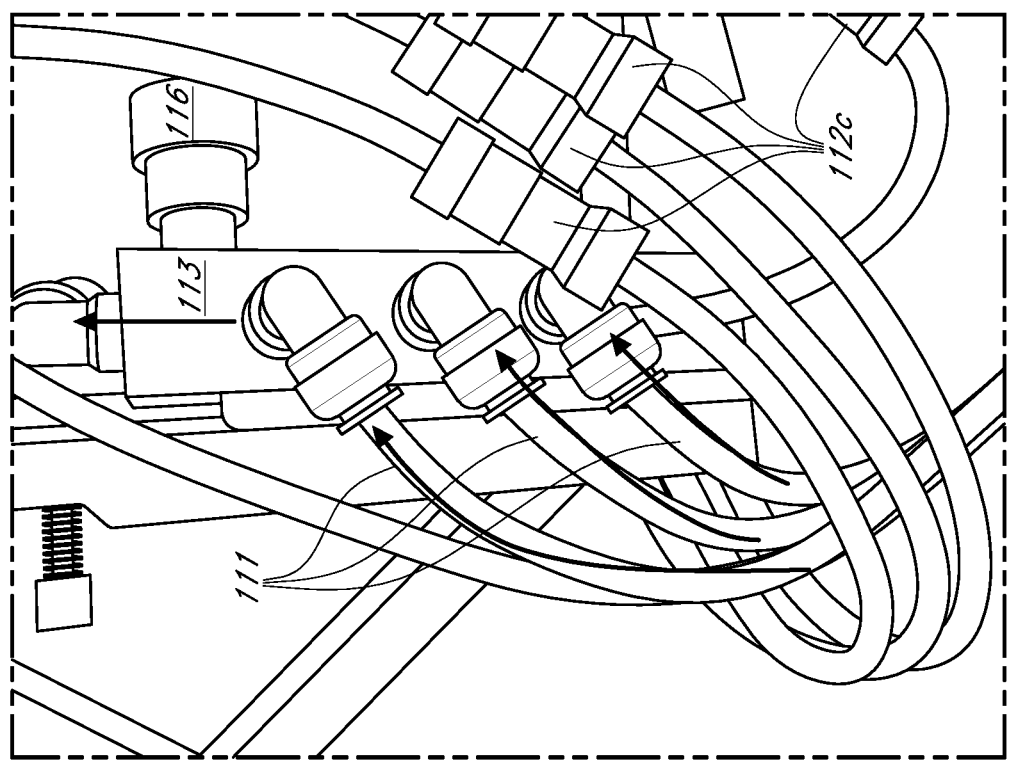

The PLC and/or PAC, which was previously mentioned above, and which is described in further detail below, may be configured to select one of the three sample fluid inlet lines 111 by opening a valve 112 associated with that specific sample fluid inlet line 111 and closing the valves 112 associated with the other sample fluid inlet lines 111. As shown in FIG. 24B, the sample fluid may then flow through the open valve 112 and into a sample fluid manifold 113 as shown at least in FIG. 24C. Within the sample fluid manifold 113 the sample fluid may pass through a flow switch 116. Generally, the flow switch 116 may work in cooperation with the PLC and/or PAC to notify same if there is sample fluid flow, or if there is no sample fluid flow, such that data from the flow switch 116 may allow the PLC and/or PAC to determine if and what corrective actions are needed, proper functioning of various components, and/or in determining if one or more components (e.g., sensor, valve, etc.) is malfunctioning and/or failing without limitation unless otherwise indicated in the following claims. Accordingly, the data from the flow switch 116 may aid the PLC and/or PAC in monitoring, controlling, and correcting issues in an illustrative embodiment of a fluid monitoring system and method. Another flow switch 116 may be utilized in the auxiliary sample system 170 as described in further detail below to provide similar functionality regarding the flow of sample fluid to one or more auxiliary systems, sensors, components, etc. without limitation unless otherwise indicated in the following claims. Still another flow switch 116 may positioned on the sample fluid manifold 113 (which may be referred to herein below as a "backwash flow switch") may provide the same functionality regarding the flow of wash fluid and associated components for providing wash fluid flow having a certain desired set of flow characteristics to certain portions of the flow cell 110 without limitation unless otherwise indicated in the following claims.

Sample fluid exiting the sample fluid manifold 113 may flow through the flow switch 116 as described above, which flow switch 116 may cooperate with other fluid handling components to achieve a desired action in response to specific conditions, and fluid flow characteristics (e.g., volumetric and/or mass flow rate, turbulence, etc.) of the sample fluid through at least one flow meter 116a engaged with the sample fluid manifold 113. The flow meter 116a may be configured at a Smart Magmeter flow meter 116a. This flow meter 116a and flow switch 116 may act as a type of critical monitoring point for the flow cell 110 in that if this flow meter 116a and flow switch 116 each indicate fluid flow has stopped at each monitoring point, it is likely that sample fluid is not moving through the flow cell 110. The PLC and/or PAC may be configured to take one or more corrective actions (e.g., back flush the current sample fluid inlet line 111, switch the valves 112 to select a different sample fluid inlet line 111, etc.). The sample fluid manifold 113 may also be equipped with at least one pressure sensor 115, an additional flow switch 116, and/or an additional flow meter 116a for providing data the PLC and/or PAC may use for monitoring, controlling, and/or correcting issues in the sample fluid or wash fluid systems and associated components as described in further detail below and without limitation unless otherwise indicated in the following claims.

If the PLC and/or PAC encounters a set of conditions that require the sample fluid provided to the flow cell 110 should come from a different sample fluid inlet line 111, the PLC and/or PAC may pause all local signal outputs (i.e., those signal outputs for components that are positioned on or adjacent to the flow cell 110) and open the valving associated with the secondary drain 127a (described in further detail below), and the control valve 112d on the sample fluid manifold 113 to fill the flow cell 110 and associated fluid handling components with sample fluid from the newly selected sample fluid inlet line 111 and remove sample fluid provided through the previous sample fluid inlet line 111 as quickly as possible.

Figure 27A:
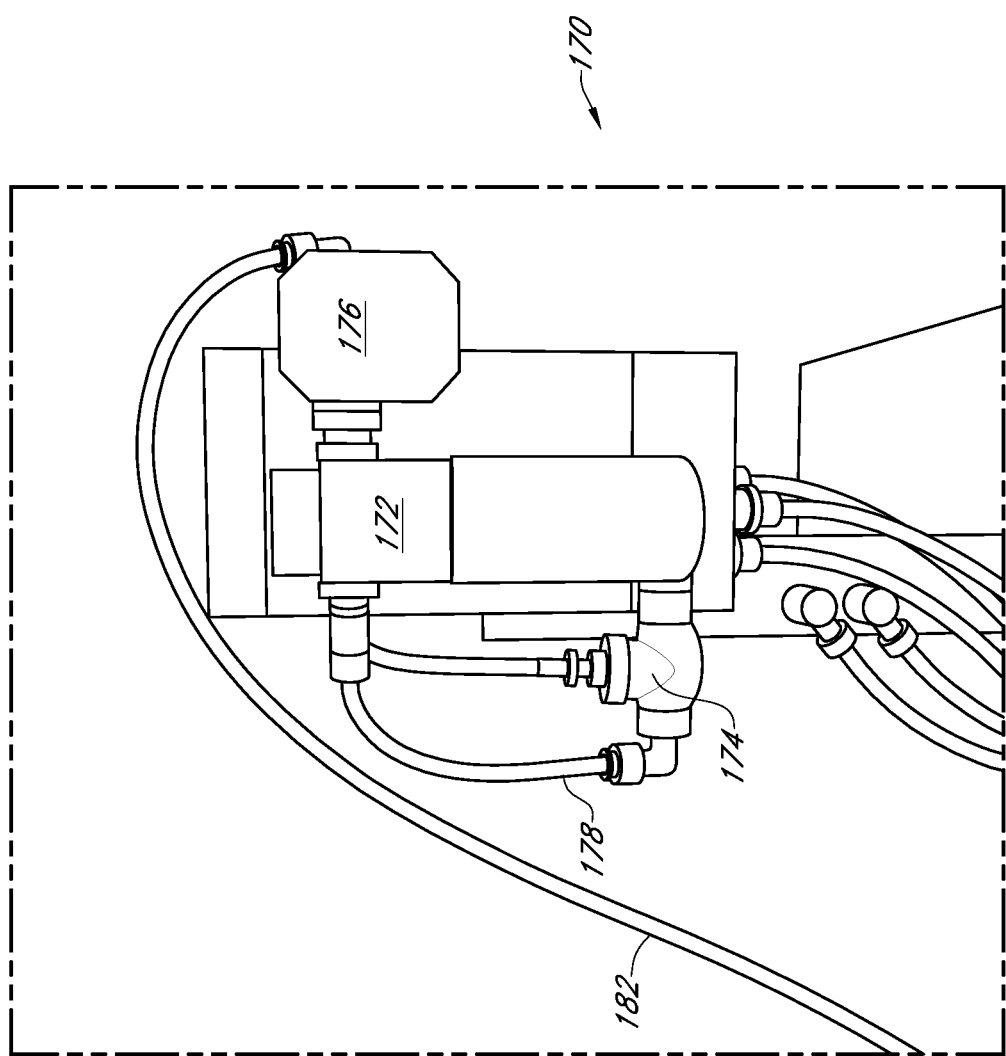
FIGS. 27A-27C provide various views of an auxiliary sample port and associated components.
Figure 27B:
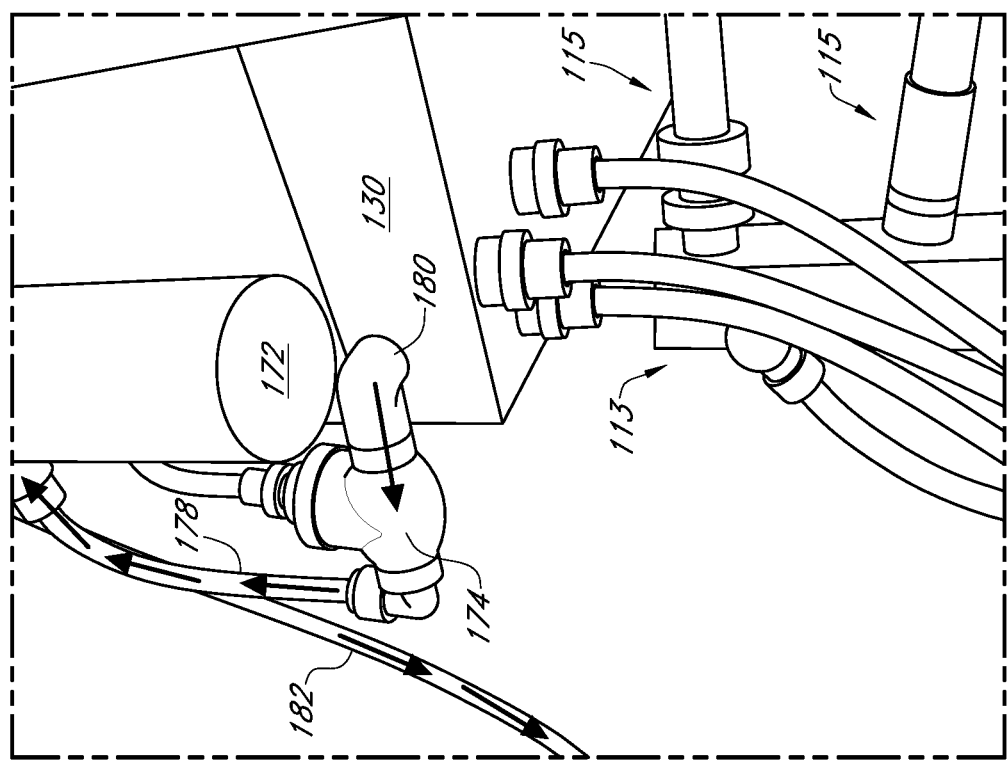
Figure 27C:
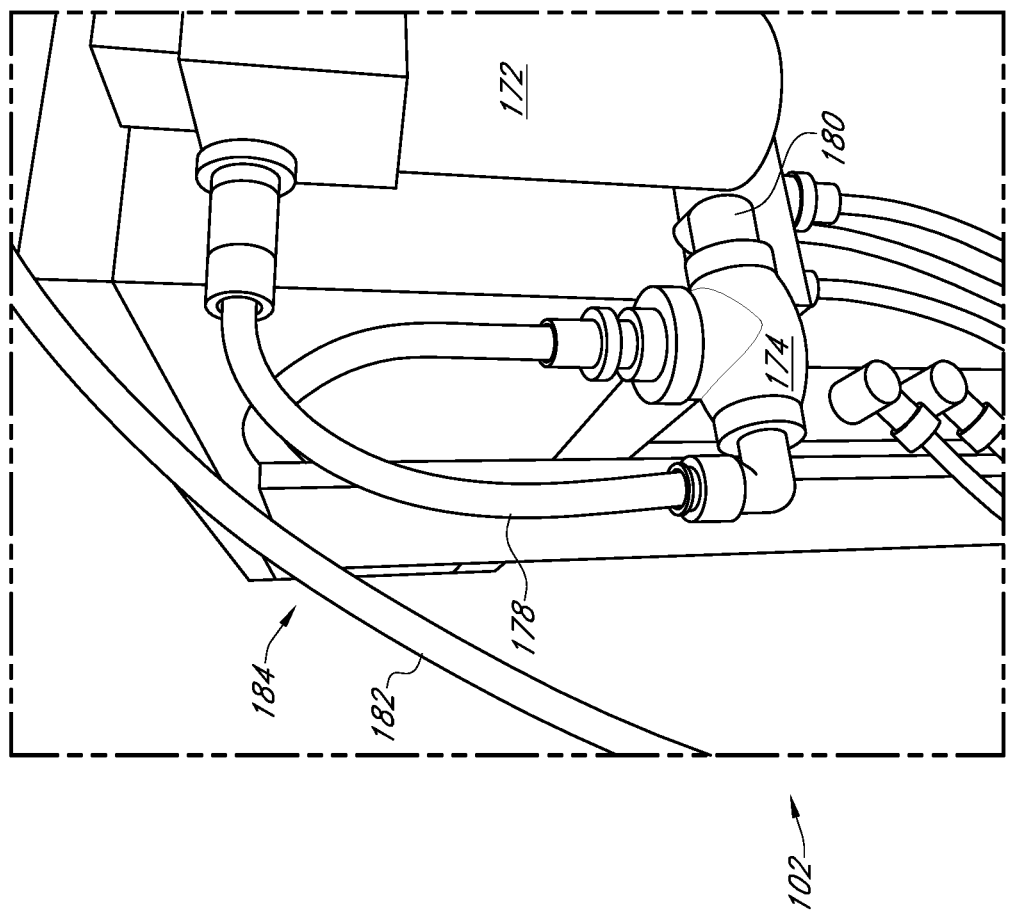

In an event in which signal outputs for sensors and/or analyzers in the flow cell 110, an auxiliary sample system 170 (an illustrative embodiment of which is shown in FIGS. 27A-27C and described in further detail below) may be especially beneficial. The auxiliary sample system 170 may be configured to ensure sample fluid flow is provided to any and all external sensors, analyzers, and/or components even when signal outputs for sensors and/or analyzers on the flow cell 110 have been paused without limitation unless otherwise indicated in the following claims.

After a suitable amount of time to ensure that the sample fluid within the flow cell 110 and associated fluid handling components is representative of the sample fluid provided from the newly selected sample fluid inlet line 111, the valving associated with the secondary drain 127a may be closed, and a fluid level sensor (which may be positioned on the cover 160 and is described in further detail below) may cooperate with control valve 112a adjacent off the side of the sample fluid manifold 113, a flow switch 116, on the sample fluid manifold 113 and a sample level detection sensor to fill the main chamber 120 with the desired amount of sample fluid as quickly as possible (which all may be controlled via the PLC and/or PAC), after which time those components may cooperate to adjust the sample fluid flow to the desired characteristics for steady state, continuous flow operation (all of which may be controlled via the PLC and/or PAC) without limitation unless otherwise indicated in the following claims. In such a manner, the flow cell 110 may be configured to accommodate pump variability, sample distance variability, residence time, etc. from one sample fluid inlet line 111 to the next. At this time (or earlier as described above after a suitable amount of time has passed to ensure that the sample fluid within the flow cell 110 and associated fluid handling components is representative of the sample fluid within the newly selected sample fluid inlet line 111) the local signal outputs may be resumed. The PLC and/or PAC may be programmed to store any data, parameters, etc. from this point forward in a new folder and/or otherwise provide an indication that a different sample fluid inlet line 111 has been selected.

Figure 24D:
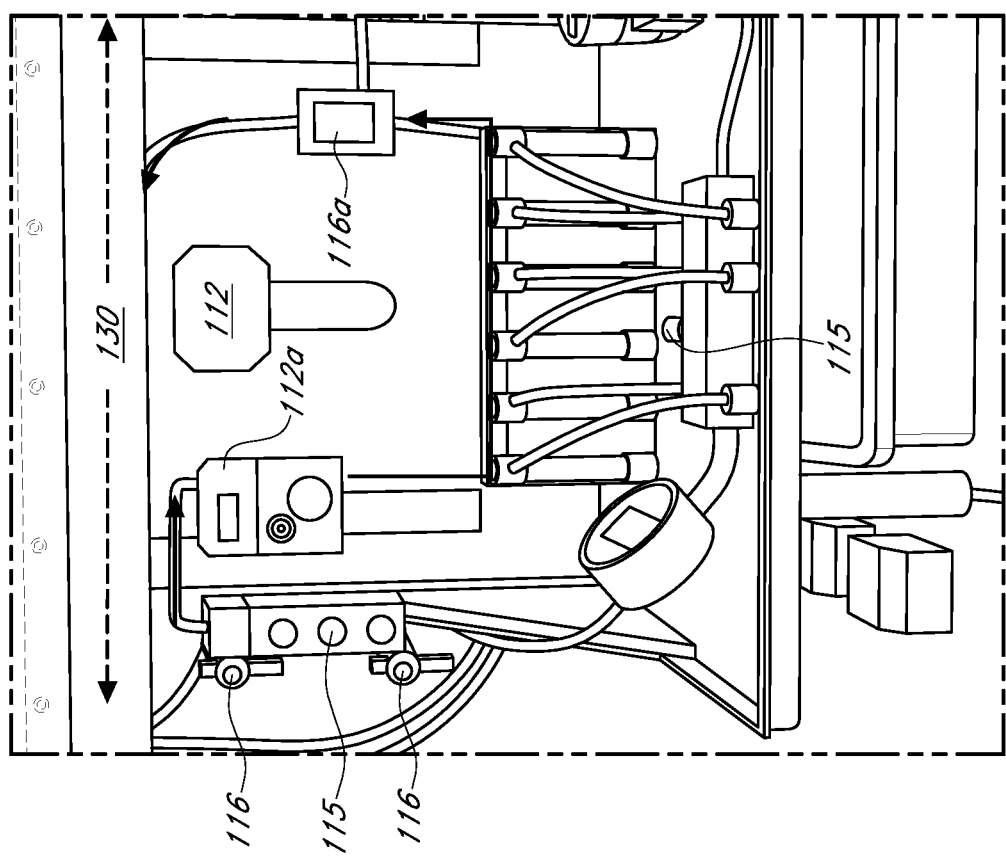

From the flow switch 116 sample fluid may pass through a control valve 112a, which for various illustrative embodiments may be configured as a proportional modulating ball valve without limitation unless otherwise indicated in the following claims) as shown at least in FIG. 24D. A control valve 112a so configured may provide several advantages compared to other types of fluid control apparatuses, such as durability, precision (e.g., fractions of a mL of fluid flow), the ability to handle multiple types of fluids, various entrained solids, slurries, etc.

From the control valve 112a the sample fluid may pass through a flow meter 116. In an illustrative embodiment, the control valve 112a may be configured as a smart control valve 112a that may allow a user to control and/or interface with the control valve 112a and/or flow meter 116 via a wireless connection through the user's mobile computing device (e.g., laptop computer, tablet computer, smart phone, etc.). The flow meter 116 may also be configured with a conductivity sensor, temperature sensor, and a flow meter without limitation unless otherwise indicated in the following claims. Various control valves 112a may be in communication with one another and/or other components of the flow cell 110 in accordance with certain logic and/or parameters that may be determined by the user utilizing the HMI. The control valve(s) 112a and/or other components of the flow cell 110 may cooperate to maintain specific flow characteristics (e.g., volumetric or mass flow rate, turbulence, linear speed, etc.) of the sample fluid through the flow cell 110. Generally, ensuring a continual, steady flow of a predetermined amount may be critical to achieving reliable and accurate data, and it is contemplated that the illustrative configuration of a control valve 112a may contribute so such a reliability and accuracy without limitation unless otherwise indicated in the following claims.

From the flow meter 116, the sample fluid may enter the base plate 130 of the flow cell 110. In the illustrative embodiment pictured herein, the sample fluid may enter the base plate 130 at a main inlet 133. In the illustrative embodiment pictured in FIG. 16A, the main inlet 133 may be configured at the center of the base plate 130 generally toward the rear side of the base plate 130, intersecting the sample fluid channel 134 as shown at least in FIG. 16B, at a position generally centered between the base plate inlets 132 shown in FIG. 16A. However, other configurations and/or positions of a main inlet 133 may be used with the flow cell 110 without limitation unless otherwise indicated in the following claims. From there the sample fluid flow may be split such that a portion flows in a first direction (e.g., to the left) and another portion flows in a second direction (e.g., to the right) through a sample fluid channel 134, which may be configured as a 0.5 inch diameter horizontal bore extending along the length of the base plate 130 from the left side to the right side of the base plate 130, which horizontal bore may generally be positioned closer to the rear side of the base plate 130 than the front side thereof along a line defined by the base plate inlets 132 shown in FIG. 16A. However, other configurations of sample fluid flow (e.g., entering at a position other than the center of the base plate 130, configuration and/or position of the sample fluid channel, flowing in a linear manner along the length of the base plate 130, not separating sample fluid flow into two differently directed streams, etc.) may be used without limitation unless otherwise indicated in the following claims.

Figure 24E:
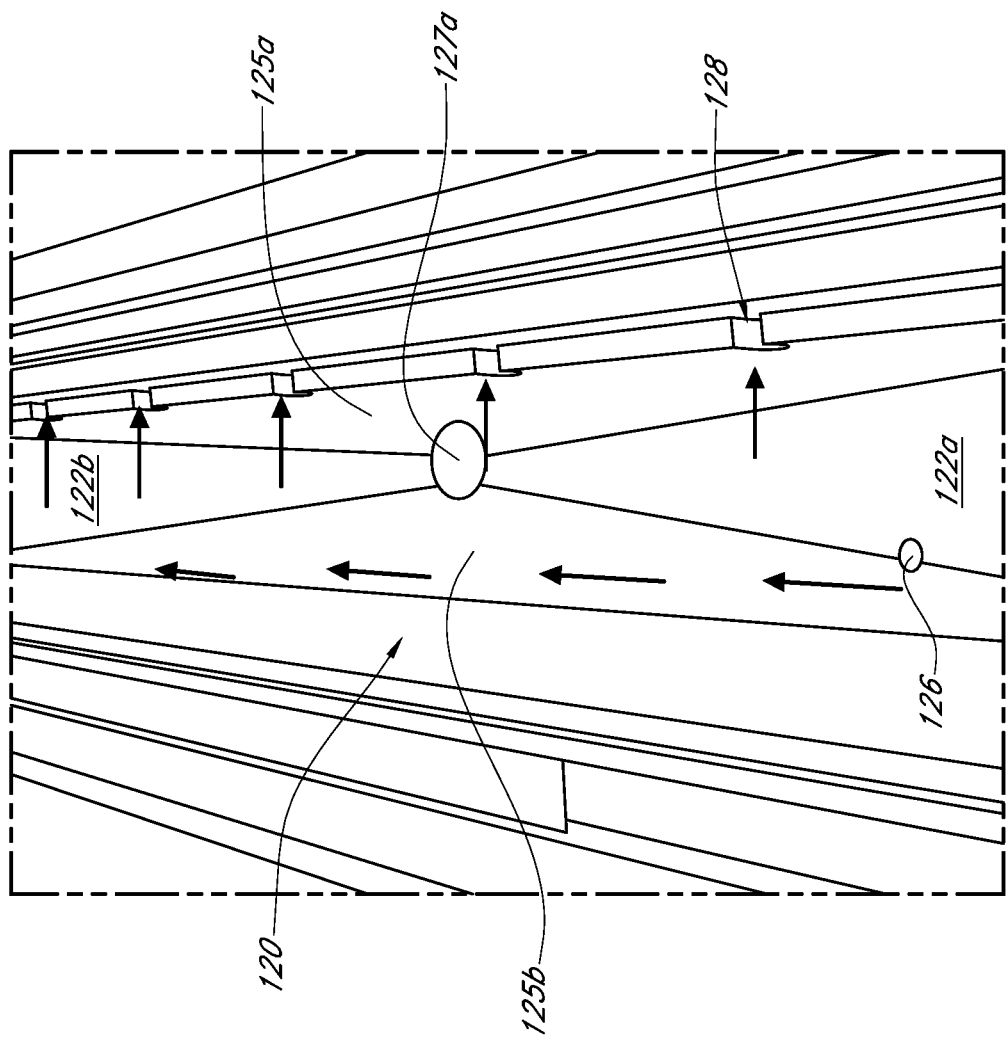
Figure 24F:
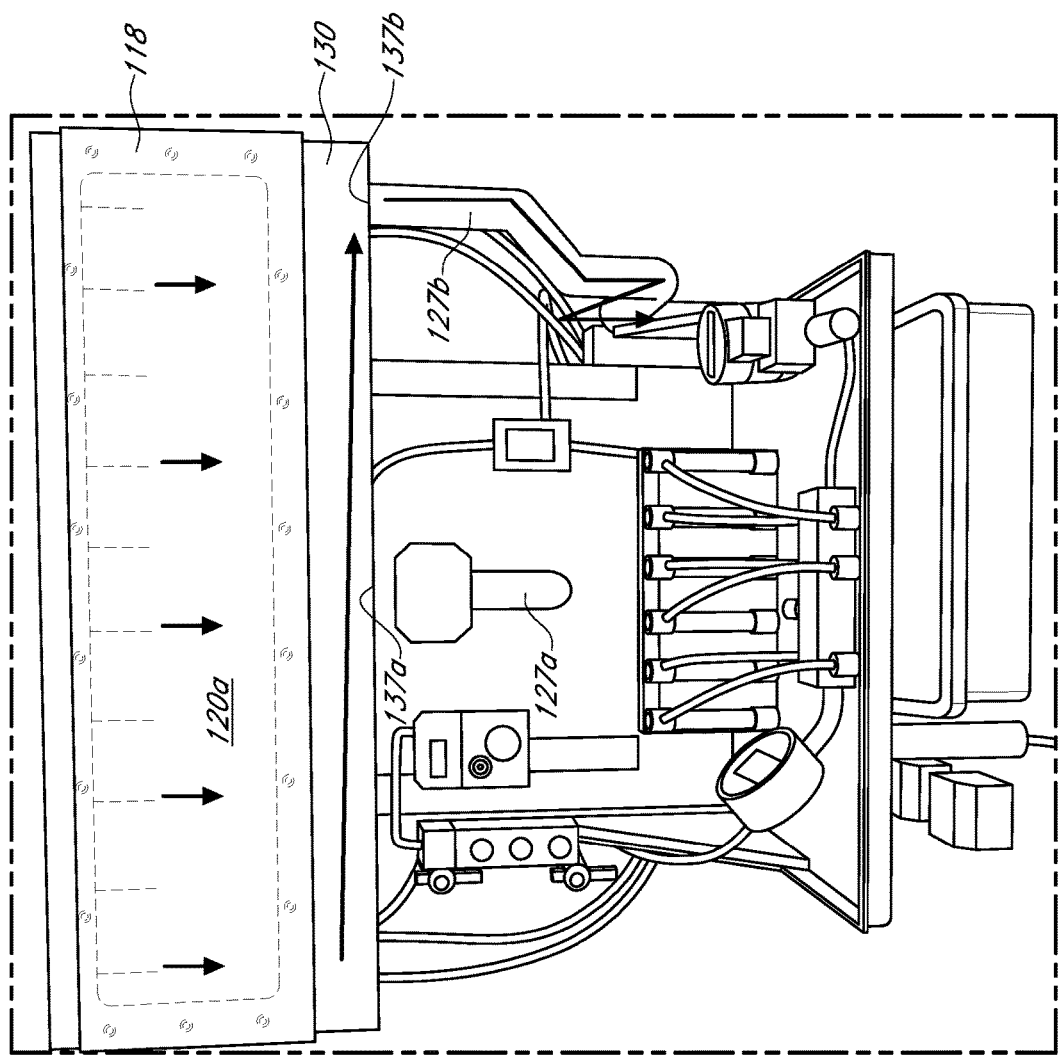

With specific reference to FIG. 24E, which provides a perspective view of an interior portion of and illustrative embodiment of a main chamber 120, from the base plate 130 sample fluid may flow upward into the main chamber 120 through one or more sample fluid inlet ports 126. In the illustrative embodiment pictured herein, the main chamber 120 may be configured with a plurality of evenly spaced sample fluid inlet ports 126 along its length, and in a preferred embodiment for certain applications there may be a total of six sample fluid inlet ports 126. The sample fluid inlet ports 126 of the main chamber 120 may correspond to the base plate inlets 132. However, the scope of the present disclosure is not limited by the number, position, configuration, spacing, dimensions, etc. of the sample fluid inlet port(s) 126 in the main chamber 120 unless otherwise indicated in the following claims.

The sample fluid may flow upward in the main chamber 120 until it reaches a fluid control guide 128a, at least one of which may be formed in a front wall 128 of the main chamber 120. In the illustrative embodiment pictured herein, the main chamber 120 may be configured with a plurality of evenly spaced fluid control guides 128a along the length of the front wall 128 (i.e., from the right side thereof to the left side), and in a preferred embodiment for certain applications there may be a total of ten fluid control guides 128a. However, the scope of the present disclosure is not limited by the number, position, configuration, spacing, configuration, dimensions, etc. of the front wall 128 and/or fluid control guides 128a in the main chamber 120 unless otherwise indicated in the following claims.

Now with specific reference to FIG. 24E, the sample fluid may exit the main chamber 120 through the fluid control guides 128a down the front surface of the front wall 128 of the main chamber 120 and into a waste reservoir 135 formed in the base plate 130. The waste reservoir 135 may extend along a portion of or nearly the entire length (i.e., from the left side thereof to the right side) of the base plate 130, and it may be configured with a slight decline from one end to the next (which for the illustrative embodiment pictured herein is from the left side to the right) to allow for gravity to provide a motivation for material within the waste reservoir 135 to flow toward the primary drain 127b. The sample fluid may then flow through a primary drain passage 137b formed in the base plate 130 and through the primary drain 127b and out of the flow cell 110 to be discarded.

Generally, the flow cell 110 and associated components may be configured to allow for a relatively high sample fluid flow rate through the flow cell 110. This may be desirable to get a more accurate sample of current sample fluid conditions (i.e., the sooner the sample fluid reaches the flow cell 110 from the sample fluid source, the more accurate the various measured variables are for a given volume of fluid at the sample fluid source from where the sample fluid is collected). Accordingly, the base plate 130 and associated components may be configured to facilitate the egress of sample fluid from the flow cell 110 (and thereby mitigate and/or eliminate the likelihood that sample fluid will back up within the flow cell 110). As such, the main chamber 120 may be configured with a vent passage 127*bb*, which vent passage 127*bb* may be configured as a channel formed in the main body 120 that is open to the atmosphere at a first end thereof and in fluid communication with the primary drain passage 137*b* and/or primary drain 127*b* at a second end thereof. Such a vent passage 127*bb* may prevent any vapor lock and/or certain pressure differentials associated with sample fluid exiting the flow cell 110 via the primary drain passage 137*b* as well as allowing such sample fluid to exit the primary drain passage 137*b* at an increased and/or steady rate without limitation unless otherwise indicated in the following claims. In one illustrative embodiment, the vent passage 127*bb* may be configured as a horizontal bore extending inward from the exterior of a second end wall 121*b* by approximately one inch and there intersecting a generally vertical bore that is in fluid communication with the primary drain passage 137*b*. However, other structures and/or methods may be used to accommodate adequate sample fluid flow through the flow cell 110 without limitation unless otherwise indicated in the following claims. Generally, a vent passage 127*bb* so configured may allow the illustrative embodiment of a flow cell 110 to process relatively large volumetric flow rates of sample fluid, such as volumetric flow rates of 30,000 mL/min or greater.

Such a high volumetric flow rate may provide a more current representation of the user's process and conditions of the sample fluid at a given point in time because oftentimes sample lines from the point of a process where the sample originates to the flow cell 110 can be quite lengthy. At slower sample rates (i.e., smaller volumetric flow rates of sample fluid), by the time the sensors in the flow cell 110 collect a measurement of the process and/or sample fluid, the process and/or sample fluid conditions could very easily have changed. The quicker a facility is aware of these changes, the better a facility can optimize, as well as make corrections. Early detection of these events can be the difference between having a catastrophe or a near miss.

Figure 25A:
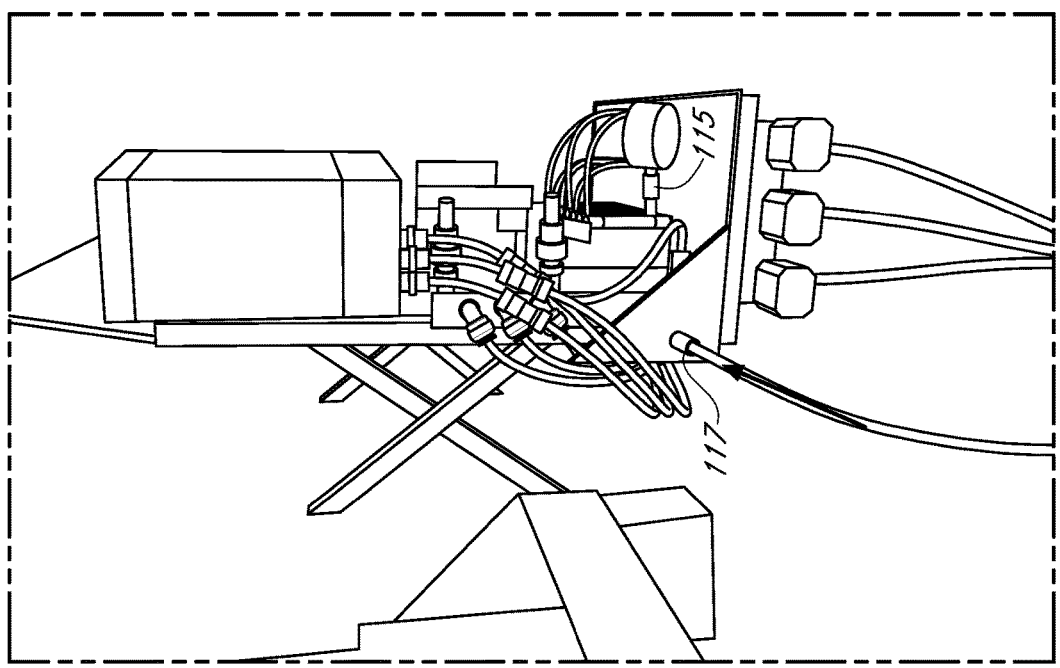
Figure 25B:
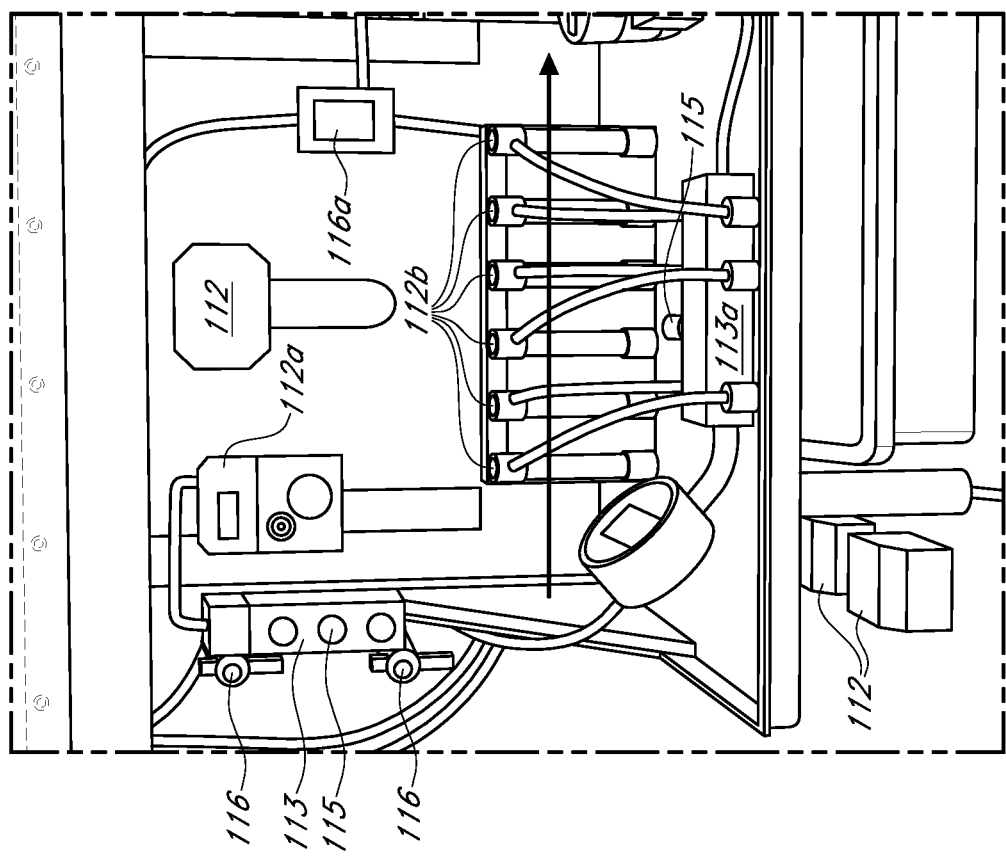

Referring generally now to FIGS. 25A-24I, various views of an illustrative embodiment of a flow cell 110 and/or portions thereof are shown. Additionally, FIGS. 24A-24I provide an illustrative method of wash fluid flow into, through, and from the illustrative embodiment of a flow cell 110, wherein various arrows are used to show various paths the wash fluid may take. With specific reference to FIG. 25A, wash fluid may enter the flow cell 110 adjacent the left side of the flow cell 110 via a wash fluid inlet 117. Now with reference to FIG. 25B, the wash fluid may flow through a conduit adjacent the rear side of the flow cell 110 to a pressure booster pump 119, and from the pressure booster pump 119 to a solenoid valve 112*b*. Once the PLC and/or PAC and/or operator directs the solenoid valve 112*b* to open, the wash fluid may pass through the solenoid valve 112*b* to the wash fluid manifold 113*a*. Additionally, in certain illustrative embodiments the wash fluid manifold 113*a* may be equipped with a pressure sensor without limitation unless otherwise indicated in the following claims.

Figures 25D, 25E:
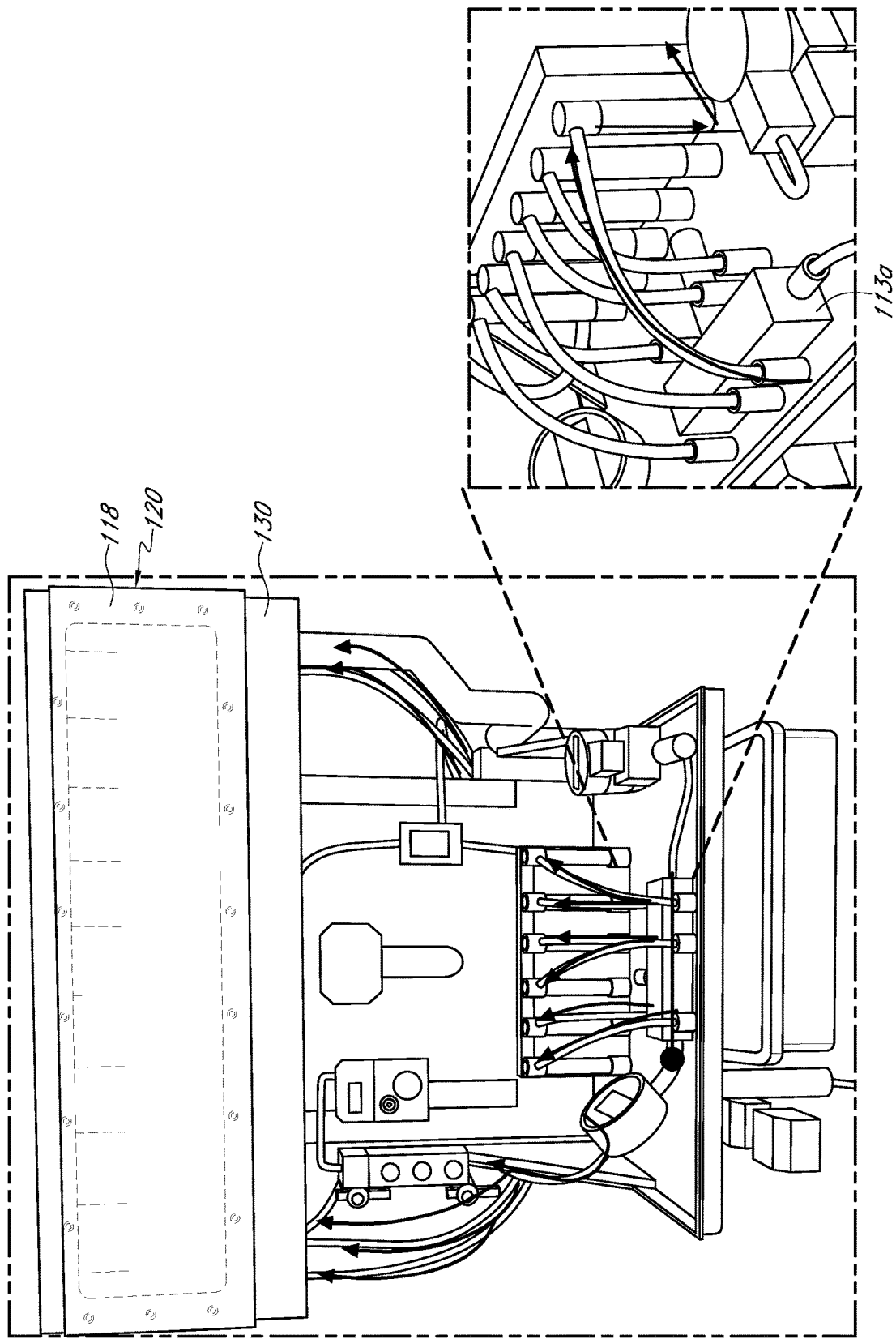

Referring specifically to FIGS. 25D & 25E, from the wash fluid manifold 113*a*, wash fluid may be dispersed in at least one direction, and in the illustrative embodiment pictured herein the wash fluid may be dispersed in up to six different directions, wherein each direction may be associated with a specific solenoid valve 112*b*. However, other embodiments may be differently configured for dispersing wash fluid (i.e., different numbers of directions, different locations, different fluid handling components (e.g., piping and/or valving configurations, flow meters, etc.), etc.) without limitation unless otherwise indicated in the following claims. Generally, in the illustrative embodiment the position of any given solenoid valve 112*b* may be dictated and/or determined by the PLC and/or PAC and/or an operator.

In the illustrative embodiment, the solenoid valve 112*b* labeled "1" and associated fluid handling components may be configured to direct wash fluid through the base plate 130 and up the right side of the main chamber 120 to the first cleaning nozzle 140 engaged with the main chamber 120. Generally, wash fluid may be supplied to either cleaning nozzle 140, 150 utilizing a cleaning nozzle passage 124 (a portion of which may be formed in the base plate 130) providing a fluid pathway from a wash fluid source (which may be engaged with the base plate 130) to the respective cleaning nozzle 140, 150. In the illustrative embodiment, each cleaning nozzle 140, 150 may be associated with a specific cleaning nozzle passage 124, wherein a portion of the first cleaning nozzle passage 124 may be formed in a first end wall 121*a* and a portion of a second cleaning nozzle passage 124 may be formed in a second end wall 121*b* of the main chamber 120 as shown at least in FIGS. 16A, 19B, and 19C. Another portion of each cleaning nozzle passage 124 may be formed in the base plate 130. However, other configurations of providing wash fluid to one or more cleaning nozzles 140, 150 may be utilized without limitation unless otherwise indicated in the following claims.

It is contemplated that for specific applications it may be desirable to reduce as many flow restrictions as possible along the fluidic path from the wash fluid manifold 113*a* to the first cleaning nozzle 140 to ensure as high of wash fluid velocity, volumetric flow, pressure, and/or mass flow as possible for more complete flushing/cleaning of a certain portion of the main chamber 120 without limitation unless otherwise indicated in the following claims.

The solenoid valve 112*b* labeled "2" and associated fluid handling components may be configured to direct wash fluid to the sample fluid inlet ports 126, a number of base plate inlets 132, and/or a portion of the sample fluid channel 134 (which portion thereof and sample fluid inlet ports 126 may be generally positioned on the right side of the main chamber 120).

Subsequently, any spent wash fluid and/or material collected thereby may exit the flow cell 110 through the secondary drain 127*a* and associated fluid handling components.

The solenoid valve 112*b* labeled "3" and associated fluid handling components may be configured to direct wash fluid to provide a backflush to a sample fluid inlet line 111 and/or sample fluid manifold 113. The wash fluid may enter the sample fluid manifold 113 at an end thereof opposite to the end in which the sample fluid enters, and the PLC and/or PAC may cause the control valve 112*a* adjacent the sample fluid manifold 113 to close to ensure wash fluid backflushes a specific valve 112 associated with a specific sample fluid inlet line 111.

The solenoid valve 112*b* labeled "4" and associated fluid handling components may be configured to direct wash fluid to provide a backflush to the waste reservoir 135. Generally, the flow cell 110 may be configured such that the wash fluid enters the waste reservoir 135 adjacent the left side thereof (e.g., opposite the primary drain passage 137b) such that the wash fluid may flush any sediment or other material out of the waste reservoir 135 out of the flow cell 110 through the primary drain passage 137b.

The solenoid valve 112b labeled "5" and associated fluid handling components may be configured to direct wash fluid to the sample fluid inlet ports 126, a number of base plate inlets 132, and/or a portion of the sample fluid channel 134 (which portion thereof and sample fluid inlet ports 126 may be generally positioned on the left side of the main chamber 120). Subsequently, any spent wash fluid and/or material collected thereby may exit the flow cell 110 through the secondary drain 127a and associated fluid handling components. In one illustrative embodiment, the solenoid valve labeled "5" and that labeled "2" may be opened simultaneously to flush/clean the entire sample fluid channel 134 and all of the base plate inlets 132 of the base plate 130 as well as the sample fluid inlet ports 126 simultaneously without limitation unless otherwise indicated in the following claims.

The solenoid valve 112b labeled "6" and associated fluid handling components may be configured to direct wash fluid through the base plate 130 and up the left side of the main chamber 120 to the second cleaning nozzle 140 engaged with the main chamber 120 as described above. It is contemplated that for specific applications it may be desirable to reduce as many flow restrictions as possible along the fluidic path from the wash fluid manifold 113a to the second cleaning nozzle 150 to ensure as high of wash fluid velocity, volumetric flow, pressure, and/or mass flow as possible for more complete flushing/cleaning of a certain portion of the main chamber 120 without limitation unless otherwise indicated in the following claims. In one illustrative embodiment, the solenoid valve labeled "1" and that labeled "6" may be opened simultaneously to flush/clean the entire portion of the main chamber 120 in which sample fluid typically resides simultaneously from both the first end wall 121a and second end wall 121b without limitation unless otherwise indicated in the following claims.

Figure 25F:
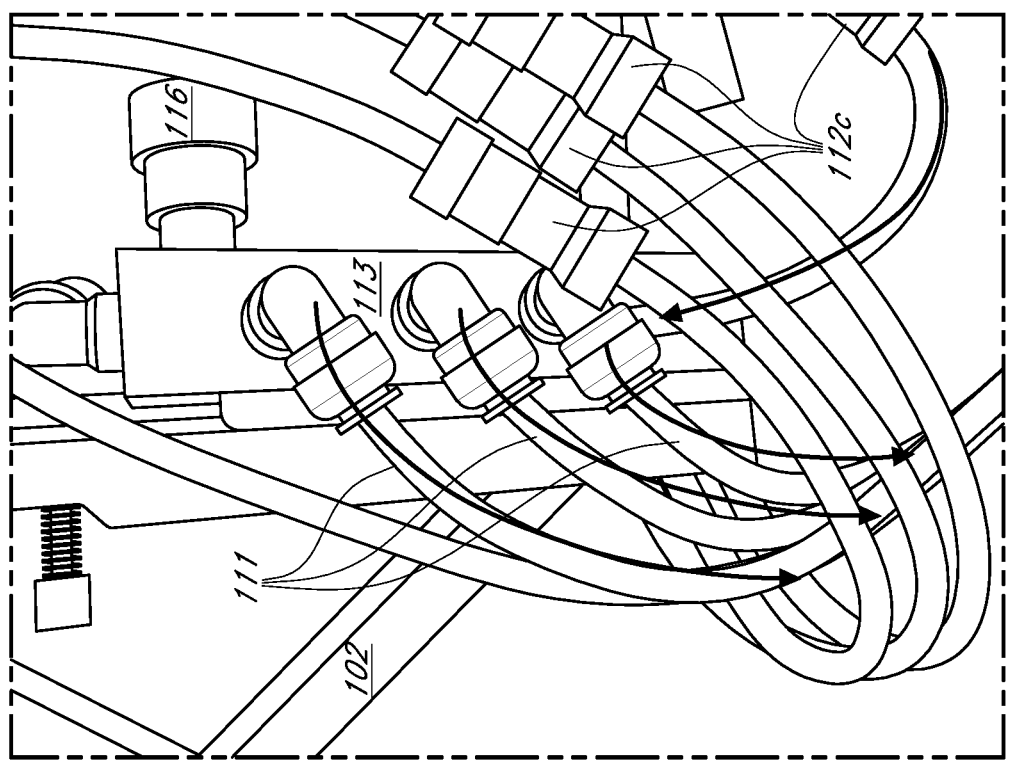
Figure 25G:
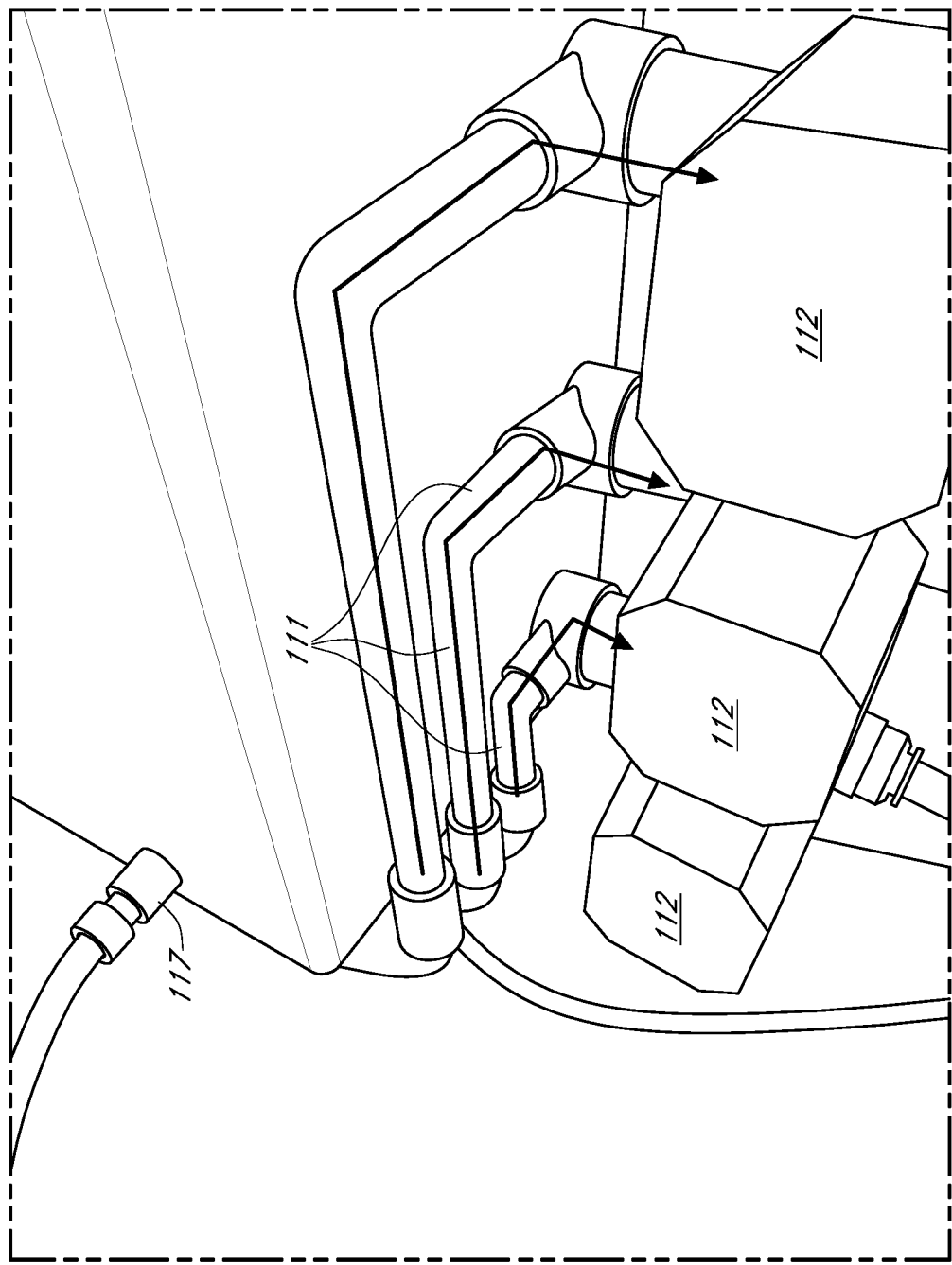

Referring to FIGS. 25F & 25G, when the solenoid valve 112b labeled "3" is selected, wash fluid may flow through the sample fluid manifold 113 in a direction opposite to the direction in which sample fluid flows therethrough during operation and continue flowing through each sample fluid inlet line 111 (three of which sample fluid inlet lines 111 are shown in the illustrative embodiment). The wash fluid may continue to flow through the sample sequencer. The valve 112 associated with the sample fluid inlet line 111 may be opened via the PLC and/or PAC and/or an operator such that the wash fluid may pass into and through the sample fluid inlet line 111 associated with the open valve 112.

Figure 25H:
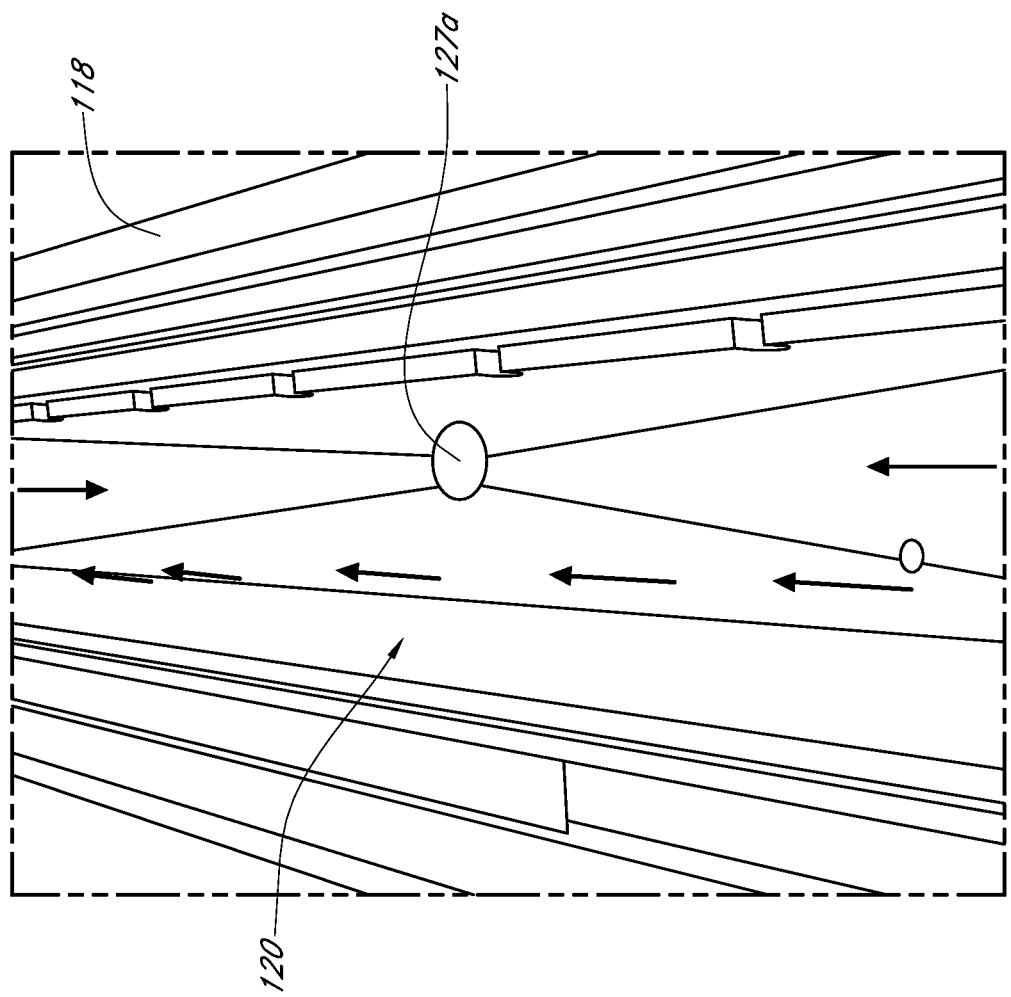

Referring to FIG. 25H, when the solenoid valve 112b labeled "2" is selected, wash fluid may flow through the sample fluid inlet ports 126 on the right side of the main chamber 120, and when the solenoid valve 112b labeled "5" is selected, wash fluid may flow through the sample fluid inlet ports 126 on the left side of the main chamber 120. When the solenoid valve 112b labeled "1" is selected, wash fluid may flow through the first cleaning nozzle 140, and when the solenoid valve 112b labeled "6" is selected, wash fluid may flow through the second cleaning nozzle 150. Any wash fluid positioned in the main chamber 120 that has been used to flush the sample fluid inlet ports 126 and/or exiting the first or second cleaning nozzles 140, 150 may be directed to the secondary drain 127a formed generally in the bottom center of the main chamber 120, which wash fluid may be directed thereto via gravity, directional spray from the first and/or second cleaning nozzle 140, 150, and/or a combination thereof.

Figure 25I:
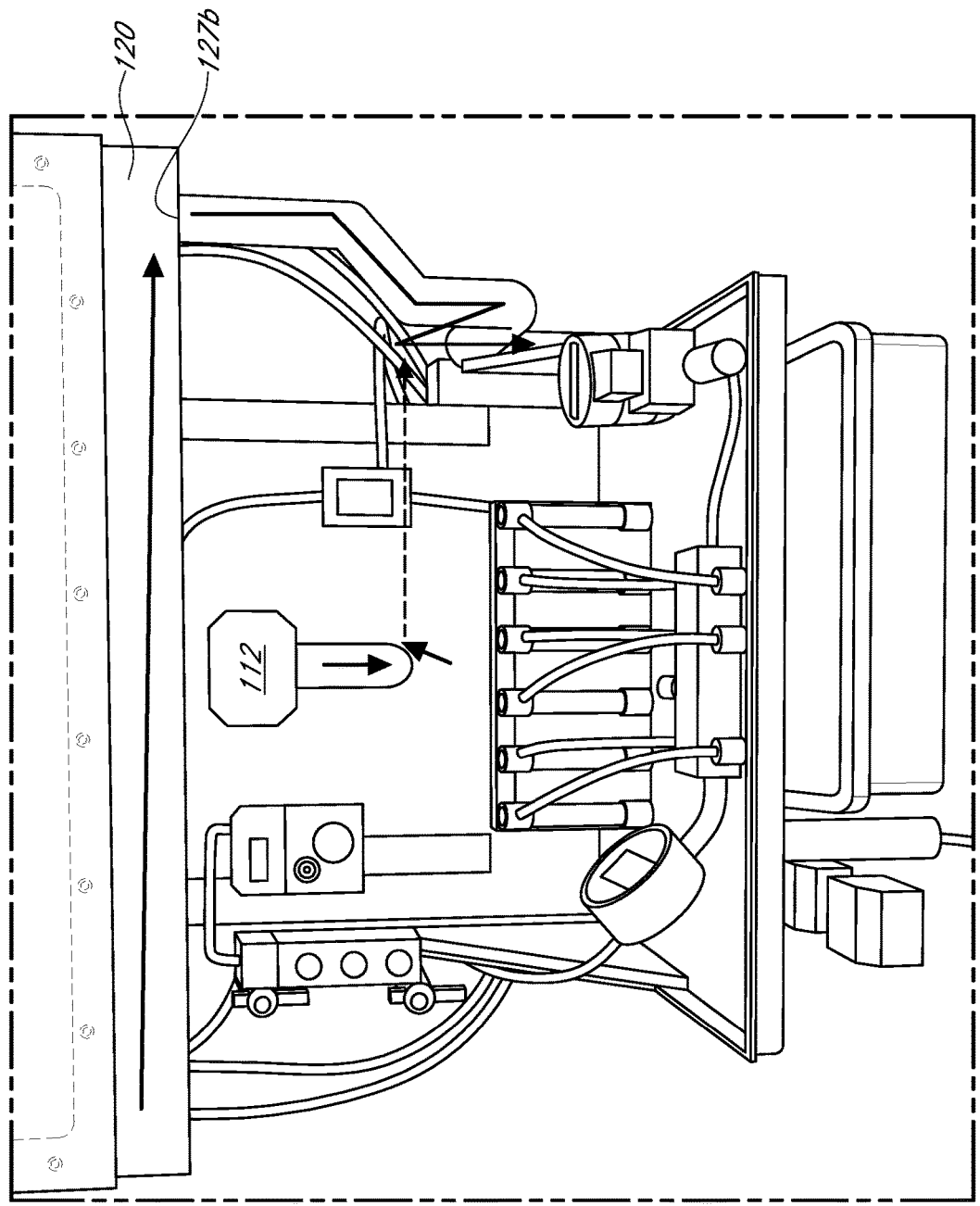

Referring now to FIG. 25I, used wash fluid may be collected in the waste reservoir 135 and flow toward the primary drain 127b, which flow may be accomplished via gravity. The secondary drain 127a may be in fluid communication with the primary drain 127b and both streams may exit the flow cell 110. Generally, it is contemplated that at least one valve 112 may be positioned in the fluid handling components between the secondary drain 127a and primary drain 127b to ensure proper flow of spent wash fluid and/or sample fluid.

Referring now to FIGS. 27A-27C, shown therein is an auxiliary sample system and associated components, wherein FIG. 27A provides an overview, FIG. 27B provides a detailed view with sample fluid flow indicated by arrows, and FIG. 27C provides a rear view of an auxiliary sample system. In the illustrative embodiment, the auxiliary sample system may be positioned generally on the left side of the flow cell 110, but the scope of the present disclosure is not so limited unless otherwise indicated in the following claims.

Generally, an illustrative embodiment of an auxiliary sample system 170 may be comprised of an auxiliary sample pump 172, auxiliary sample flow switch 174, auxiliary sample control valve 176, auxiliary sample inlet line 178, auxiliary sample inlet port 180, and an auxiliary sample feed line 182 along with associated fluid handling components (e.g., pipes, hoses, fittings, other fluid conduits, etc.) without limitation unless otherwise indicated in the following claims.

In the illustrative embodiment of an auxiliary sample system 170 pictured herein, sample fluid may enter the auxiliary sample system 170 via associated fluid conduit engaged with the base plate 130 at an auxiliary sample inlet port 180, which fluid conduit may be fluidly connected to an auxiliary sample flow switch 174 as shown at least in FIGS. 27A & 27B. The auxiliary sample flow switch 174 may be in communication with the PLC and/or PAC in the event flow becomes obstructed and/or deviates from a specific set point and may be configured to alert a user of same and/or take corrective action based on various programming scenarios. Fluid may exit the auxiliary sample flow switch 174 and enter the auxiliary sample pump 172 also as shown at least in FIGS. 27A & 27B through an auxiliary sample inlet line 178. Generally, the auxiliary sample pump 172 may be used to control the pressure of the sample fluid exiting the auxiliary sample pump 172 (and in some applications boost the fluid pressure to a specific amount, and in some illustrative embodiments at least 120 pounds per square inch without limitation unless otherwise indicated in the following claims).

From the auxiliary sample pump 174, sample fluid may enter an auxiliary sample control valve 176, which may provide selective fluid flow only when desired by the user and/or when called for via the PLC and/or PAC. In one illustrative embodiment, the auxiliary sample control valve 176 may be configured as a ball valve, but the scope of the present disclosure is not so limited unless otherwise indicated in the following claims. Accordingly, when the auxiliary sample control valve 176 is open, pressurized sample fluid may flow through an auxiliary sample inlet line 178 to provide sample fluid via an auxiliary sample feed line 182 to various sensors, instrumentation, fluid conduits, etc. that are external to the flow cell 110 without limitation unless otherwise indicated in the following claims. In an illustrative embodiment, the PLC and/or PAC may be configured to monitor various parameters of sample fluid flow through the auxiliary sample system 170 (e.g., pressure, flow rate, etc.) such that the PLC and/or PAC may respond according to predetermined programming logic if/when certain issues arise regarding sample fluid flow without limitation unless otherwise indicated in the following claims.

Referring now to FIGS. 28-32, various views of an illustrative embodiment of a fluid monitoring system & method are shown therein as well as associated components and at least one purpose for same. The illustrative embodiment shown therein, the various components thereof, and the listed purpose for each component are for illustrative purposes only and in no way limit the scope of the present disclosure unless otherwise indicated in the following claims.

| Letter | Component | Purpose |
|---|---|---|
| A | Operator's Screen | Monitor displaying processed information for operators to utilize. |
| B | Solenoid Valve - Right Side Sprayer | Allows the passing of a fluid from the wash fluid manifold, supplying the right-side sprayer. Pushes sediment towards centralized drain. |
| C | Solenoid Valve - Right Side Sample Port Flush | Allows the passing of a fluid from the wash fluid manifold, supplying the right-side sample port. Wash port flushes sediment buildup to waste and removes any blockages if present. |
| D | Solenoid Valve - Sample Line Backwash | Allows the passing of a fluid from the wash fluid manifold, supplying each sample line with pressurized fluid to remove blockages/clogs that cut off sample flow. |
| E | Solenoid Valve - Left Side Sample Port Flush | Allows the passing of a fluid from the wash fluid manifold, supplying the left-side sample port. Wash port flushes sediment buildup to waste and removes any blockages if present. |
| F | Solenoid Valve - Waste Well Flush | Allows the passing of a fluid from the wash fluid manifold, supplying the underdrain. Wash port pushes sediment and debris out of the well and to waste. |
| G | Solenoid Valve - Left Side Sprayer | Allows the passing of a fluid from the wash fluid manifold, supplying the left-side sprayer. Sprayer pushes sediment towards centralized drain. |
| H | Clean Fluid Manifold | Supplies the wash and corrective actions system with an immediate supply of pressurized fluid to perform autonomous functions. |
| I | Smart Magmeter | Monitors flow rate, temperature of sample, conductivity, and total volume. Data and control settings are communicated via Bluetooth or through hard wire. |
| J | Modulating Ball Valve | Provides precise and consistent flow control, allowing optimum sample conditions to accommodate a wide range of sensors and applications, as well as multiple automation operations. |
| K | Ball Valve - Secondary Drain | Utilized within the cleaning process to discard waste or to quickly turn overflow cell contents when switching between multiple sample streams. |
| L | Dike | Used for sample containment. Allows sample to discharge to waste at high flow rates. |
| O | Sample Sequencer Backwash Supply Line | Transports pressurized wash fluid from the wash fluid manifold to each of the three sample connection options during various automation functions. |
| P | Sample Line Backwash Check Valve | Keeps the sample fluid system separated from the clean fluid wash system. Protects all solenoid valves from contamination and free of foreign debris. Also allows both sides to maintain proper pressure, directing fluid as attended for in the design. |
| Q | 3-Channel Sample Stream Sequencer | Allows the Outfall to do the work of three process analyzers combined into one. By monitoring three independent sample streams, the amount of on-line process instrumentation needed onsite is reduced. |
| R | Clean Fluid Inlet | Connection point where clean fluid enters the system and charges the clean fluid line up to the Clean Fluid Master Solenoid Valve. |
| S | SSW Check Valves | SSW (Sample port, Sprayer, Well flush) Keeps the sample fluid system separated from the clean fluid wash system. Protects all solenoid valves from sample contamination and free of foreign debris, preventing valve failure due to particulate. Also allows both sides to maintain proper pressure, directing fluid as attended for in the design. |
| W | Cap/Sensor Mount | Customizable to mount sensors of your choice. Cap creates a leak-proof seal, keeping sample inside the unit at all times, even at high rates of flow. Also contains an LED lighting system controlled via Bluetooth. Allows for quick viewing to assure proper functioning. |
| Z | On-line Process Chloramination Analyzer | Process instrument monitoring total and free chlorine, monochloramines, and dichloramines. Used during proof of concept. |

Figure 28:
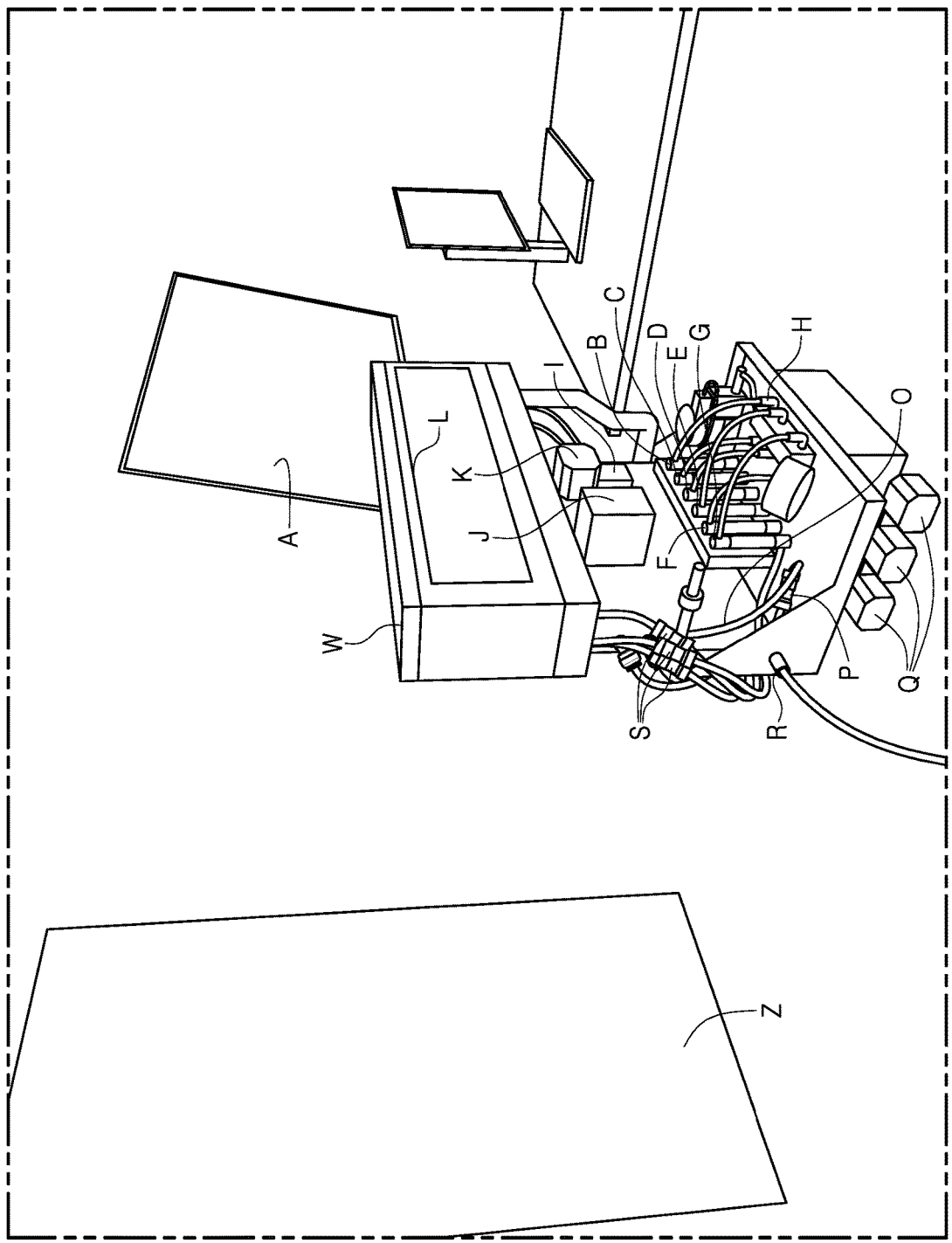
FIG. 28 provides a perspective overview of an illustrative embodiment of a fluid monitoring system & method.

Table 2 providing various components that may be used with various illustrative embodiments of a flow cell and specifically that shown in FIG. 28.

| Letter | Component | Purpose |
|---|---|---|
| A1 | Drain Vent | Allows the drain system to discard large amounts of fluid continuously without backing up. |
| B1 | LED Lighting Bluetooth Box | Bluetooth circuit board allowing the system's LED lighting to be controlled via smartphone or tablet. |
| C1 | Right Directional Flow Guide Plug | Minimizes flow velocity reduction by providing a smooth angle transition when the wash fluid's path is diverted; optimizes cleaning capacity. |
| D1 | Right Sample Canal Access Point | Serves as a maintenance function. Provides an entry point to access the 3-sample inlet ports on the left side. |
| E1 | Solenoid Valving Mount | Consists of three components that securely fastens and aligns the six solenoid valves used for cleaning and other preventative maintenance tasks. |
| F1 | Primary Drain Plumbing | Piping used to transport accumulated waste from the outlet of the Primary Drain inlet. |
| G1 | Pressure Booster Pump | Provides an adequate and consistent supply of clean fluid pressure. |
| H1 | PLC Enclosure | A waterproof, all weather NEMA 3X enclosure protecting the PLC. |
| J1 | Shelf | Provides a platform for various components. |
| L1 | Shallow Well Jet Pump | Used to supply and recirculate sample for testing purposes. Provides system with 50 LPM/75 PSI. |
| M1 | LED Lighting Manual on/off Switch | Turns the LED lighting system's power supply on or off. |
| N1 | Clean Fluid Manifold | Supplies the wash and corrective actions system with an immediate supply of pressurized fluid to perform autonomous functions. |
| O1 | Ball Valve - Secondary Drain | Utilized within the cleaning process to discard waste or to quickly turn overflow cell contents when switching between multiple sample streams. |
| Q1 | Primary Drain Inlet | Effluent of the system's waste after passing through the waste collection well within the system's Baseplate. |
| R1 | Baseplate | Bottom flow cell component consisting of an intricate network of fluid channels and a Waste Collection well. |
| S1 | Primary and Secondary Drain Plumbing | Junction point where waste from the secondary and primary drains merge. |
| T1 | Secondary Drain Plumbing | Piping used to transport accumulated waste from the outlet of the Secondary Drain inlet. |
| U1 | Secondary Drain Inlet | Effluent of the system's waste generated during the cleaning process. |
| V1 | Primary and Secondary Drain Effluent | Exit point of system's accumulated waste. |

Figure 29:
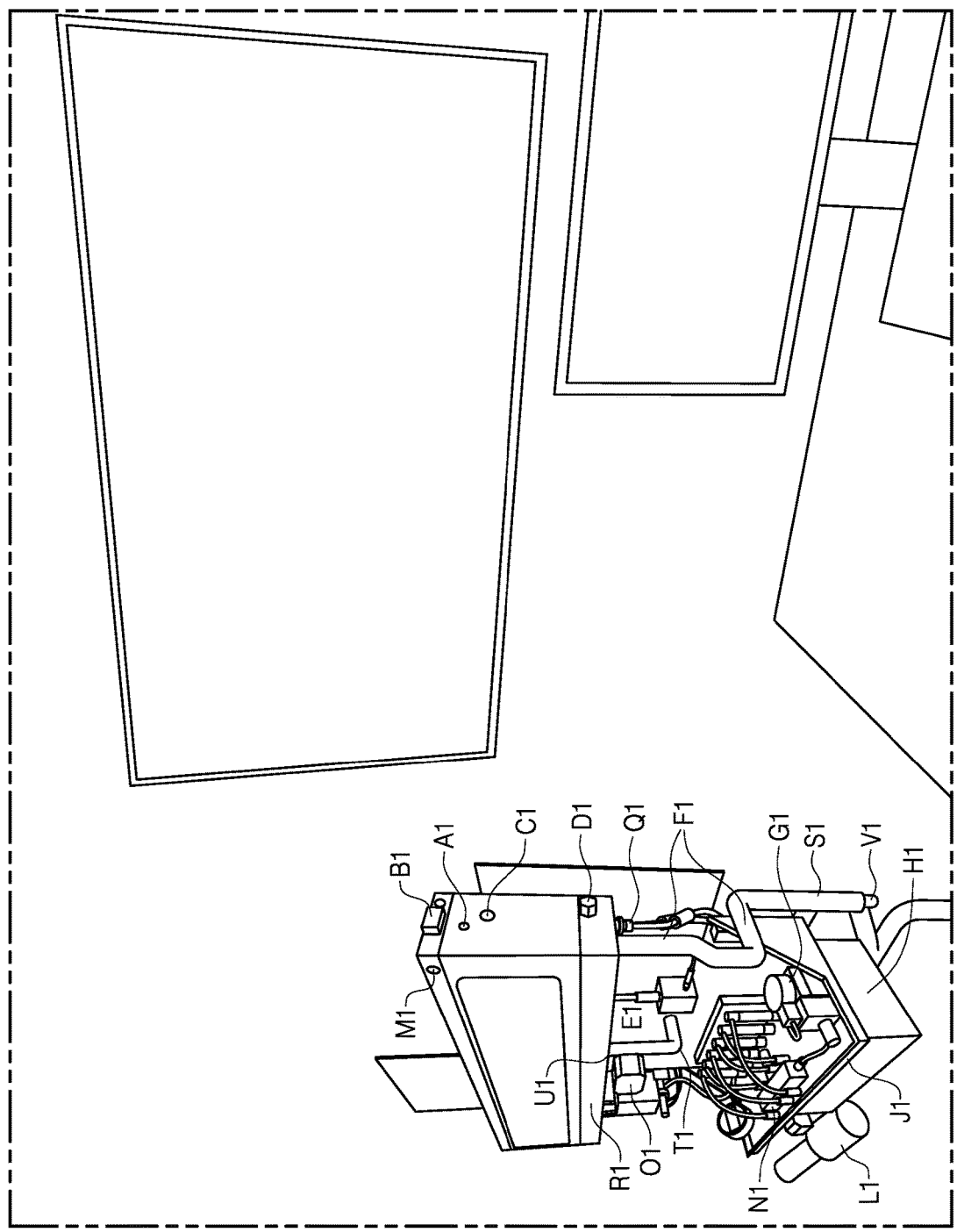
FIG. 29 provides another perspective overview of the illustrative embodiment of a fluid monitoring system & method shown in FIG. 28.

Table 3 providing various components that may be used with various illustrative embodiments of a flow cell and specifically that shown in FIG. 29.

| Letter | Component | Purpose |
|---|---|---|
| A2 | Sample Flow Switch | Used as a verification that sample flow is properly occurring. Also referenced for various indicators determining the need for the system to initiate a sample line backwash, as well as determining the proper functioning of the Modulating Ball Valve. |
| B2 | Backwash Flow Switch | Used as a verification that the backwash solenoid valve is properly functioning. Also referenced for various indicators for the system's backwash automation in determining process completion and built in safety features. |
| C2 | Sample Pressure Sensor | Monitors pressure within the Sample Manifold aiding in protecting various components. Also used as a reference measurement within the system's automation during the sample line backwash operations. |
| D2 | Clean Fluid Manifold | Supplies the wash and corrective actions system with an immediate supply of pressurized fluid to perform autonomous functions. |
| E2 | Pressure Booster Pump | Provides an adequate and consistent supply of clean fluid pressure. |
| F2 | 3rd Sample Stream Ball Valve | 3rd out of 3 ball valves that make up the 3-Channel Sample Stream Sequencer. |
| G2 | 2rd Sample Stream Ball Valve | 2nd out of 3 ball valves that make up the 3-Channel Sample Stream Sequencer. |

-continued

| Letter | Component | Purpose |
| --- | --- | --- |
| H2 | Clean Fluid Pressure Sensor | Monitors pressure within the Clean Fluid Manifold aiding in protecting various components and adequate pressure is being supplied. Also used as a reference measurement aiding in the corrective actions for various automatic actions. |
| I2 | Smart Magmeter | Monitors flow rate, temperature of sample, conductivity, and total volume. Data and control settings are communicated via Bluetooth or through hard wire. Aids in multiple autonomous actions. |
| K2 | Solenoid Valves 1-6 | Bank of valves for various automation functions (See Chart 1 for details), each receiving fluid from the Clean Fluid Manifold. |
| M2 | Left Sprayer Inlet | Connection point where pressurized fluid coming from solenoid valve 6 enters the Baseplate. |
| N2 | Well Flush Inlet | Connection point where pressurized fluid coming from solenoid valve 4 enters the Baseplate. |
| O2 | Right Sample Port Flush Inlet | Connection point where pressurized fluid coming from solenoid valve 2 enters the Baseplate. |
| P2 | Modulating Ball Valve | Provides precise and consistent flow control, allowing optimum sample conditions to accommodate a wide variety of sensors and applications. Utilized in multiple automation operations. |
| Q2 | Ball Valve - Secondary Drain | Utilized within the cleaning process to discard waste or to quickly turn overflow cell contents when switching between multiple sample streams. |
| S2 | Viewing Window O-Ring | Creates a sealed, water-tight perimeter, lying in between the viewing window and flow cell block. |

Figure 30:
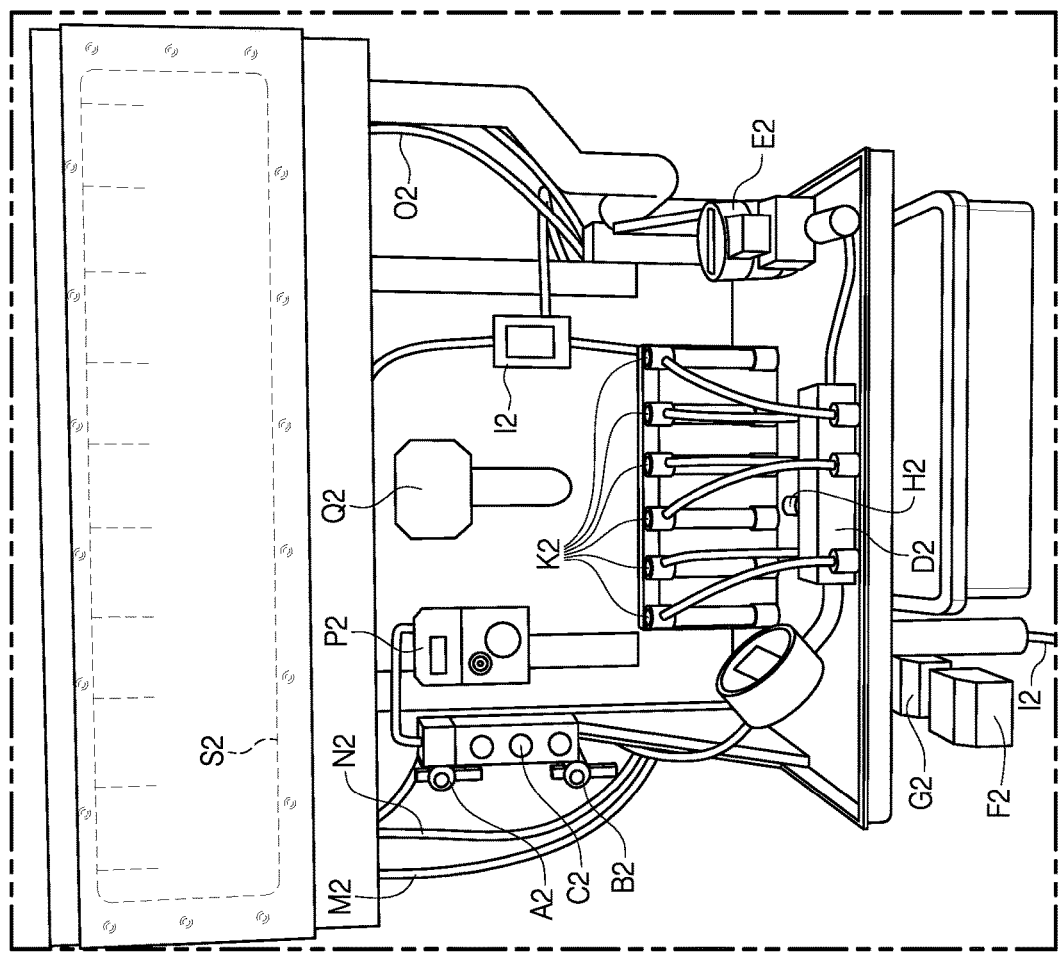
FIG. 30 provides another perspective overview of the illustrative embodiment of a fluid monitoring system & method shown in FIGS. 28 & 29.

Table 4 providing various components that may be used with various illustrative embodiments of a flow cell and specifically that shown in FIG. 30.

| Letter | Component | Purpose |
| --- | --- | --- |
| A3 | Left Sprayer Inlet | Connection point where pressurized fluid coming from solenoid valve 6 enters the Baseplate. |
| B3 | Well Flush Inlet | Connection point where pressurized fluid coming from solenoid valve 4 enters the Baseplate. |
| C3 | Left Sample Port Flush Inlet | Connection point where pressurized fluid coming from solenoid valve 2 enters the Baseplate. |
| D3 | Primary Sample Stream Manifold Inlet | Inlet connection point where sample from ball valve 1 within the 3-Channel Sample Stream Sequencer enters the Sample Manifold. |
| E3 | 2nd Sample Stream Manifold Inlet | Inlet connection point where sample from ball valve 2 within the 3-Channel Sample Stream Sequencer enters the Sample Manifold. |
| F3 | 3rd Sample Stream Manifold Inlet | Inlet connection point where sample from ball valve 3 within the 3-Channel Sample Stream Sequencer enters the Sample Manifold. |
| H3 | Clean Fluid Inlet | Connection point where clean fluid enters the system and charges the clean fluid line up to the Clean Fluid Master Solenoid Valve. |
| J3 | 3-Channel Sample Stream Sequencer | Allows the Outfall to do the work of three process analyzers combined into one. By monitoring three independent sample streams, the amount of on-line process instrumentation needed onsite is reduced. |
| K3 | Clean Fluid Pressure Sensor | Monitors pressure within the Clean Fluid Manifold aiding in protecting various components and adequate pressure is being supplied. Also used as a reference measurement aiding in the corrective actions for various automatic actions. |

Figure 31:
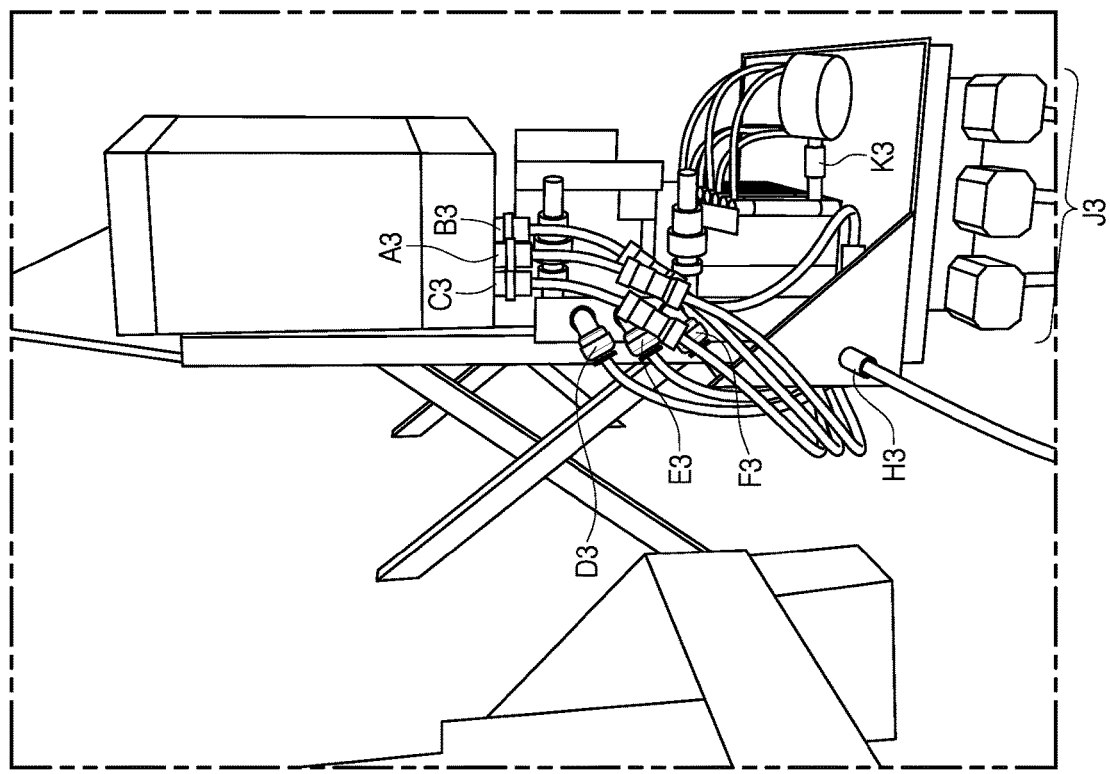
FIG. 31 provides another perspective overview of the illustrative embodiment of a fluid monitoring system & method shown in FIGS. 28, 29, & 30.

Table 5 providing various components that may be used with various illustrative embodiments of a flow cell and specifically that shown in FIG. 31.

| Letter | Component | Purpose |
| --- | --- | --- |
| A4 | Right Sprayer Inlet | Connection point where pressurized fluid coming from solenoid valve 1 enters the Baseplate. |
| B4 | Right Sample Canal Access Point | Serves as a maintenance function. Provides an entry point to access the 3-sample inlet ports on the right side. |

| Letter | Component | Purpose |
| --- | --- | --- |
| C4 | Check Valves | Keeps the sample fluid system separated from the clean fluid wash system. Protects all solenoid valves from sample contamination and free of foreign debris, preventing valve failure due to particulate. Also allows both sides to maintain proper pressure, directing fluid as attended. |
| D4 | Right Directional Flow Guide Plug | Minimizes flow velocity reduction by providing a smooth angle transition when the wash fluid's path is diverted; optimizes cleaning capacity. |
| E4 | Drain Vent | Allows the drain system to discard large amounts of fluid continuously without backing up. |
| F4 | LED Light System Charging Dock | Charges the internal battery or independently supplies power to the LED Light System by use of the onboard power converter by inserting the connector located on the back right side of the flow cell. |
| G4 | LED Light Bluetooth Box | Bluetooth circuit board allowing the system's LED lighting to be controlled via smartphone or tablet. |

Figure 32:
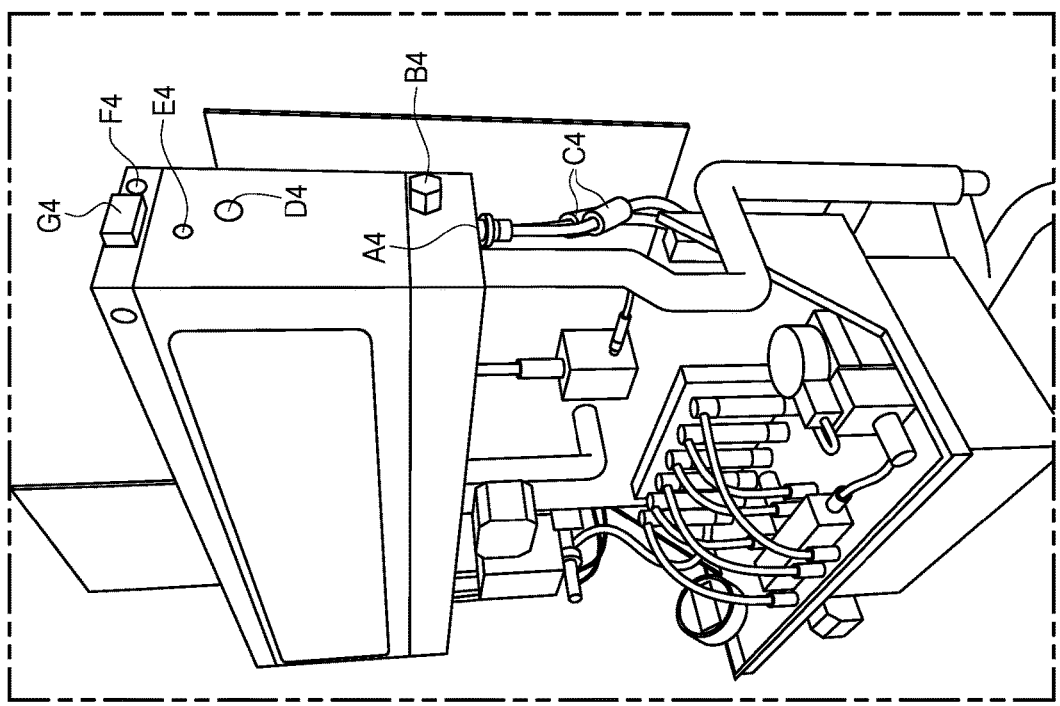
FIG. 32 provides another perspective overview of the illustrative embodiment of a fluid monitoring system & method shown in FIGS. 28, 29, 30, & 31.

Table 6 providing various components that may be used with various illustrative embodiments of a flow cell and specifically that shown in FIG. 32.

Benefits/Features of the Illustrative Embodiments of Fluid Monitoring Systems & Methods The following benefits/features of a fluid monitoring system & method may be found in one or more illustrative embodiments thereof disclosed herein, wherein the various features and/or benefits may be optional unless otherwise indicated in the following claims. Such benefits/features are not meant to be limiting to the scope of the present disclosure and/or any fluid monitoring system, method, and/or flow cell 10, 110 unless otherwise indicated in the following claims and a nearly infinite combination of compatible features and/or benefits exist.

The analytical instrumentation industry is driven by the need for a productive solution that reduces the total operating costs for a customer. Advanced analytical technologies that enable faster analysis will help customers to achieve high productivity in their operations. Key manufacturers are trying to merge with companies to strengthen their product portfolio with additional offerings and to have a solid presence in all market segments. By this, companies are transforming to offer their customers a total solution from basic product offering. Solution selling is the way forward as customers value it and it also increases the revenue generated by vendors. For example, the pharmaceutical industry, which cannot survive without analytical instruments for their routine operations, has requirements for sophisticated equipment that will help them to meet tightening regulations. End users' demand pushes manufacturers to offer sophisticated equipment that resolves customers' day-to-day challenges.

The Outfall SmartCell (Outfall SC) is the world's first universal total solution for customers within the analytical instrumentation industry. Not bound to any one industry or process, the Outfall SC is a multifunctional process control device and IoT Integrated System all in one. This process control device "add-on" easily interconnects with any pre-existing process control instrument (instrument). This technological convergence provides benefits never seen before within a single device, while simultaneously transforming outdated instruments into the industry's most advanced. By serving multiple purposes, it provides industrial manufacturing facilities with several, annual cost savings opportunities, while increasing workplace safety. Since flow cells are a common component within instruments that are used for sample analysis, they are applied across multiple industries. The Outfall SC's engineering and technology allow for the substitution between these flow cells, incorporating the pre-existing instrument's sensor(s) and transmitter into the Outfall SC, regardless of make or model. The Outfall SC's cutting-edge technology will connect and communicate with ANY process control instrument that has the capacity for data communication. This allows facilities to be able to utilize their pre-existing transmitters and sensors for their process's sample analysis; thus, reducing integration costs, while increasing automation capabilities. Its versatility, and convergence of multiple of the latest technologies offered today, makes the Outfall SC unique amongst current products offered throughout all markets.

The Outfall SC's large flow cell allows for multiple sensors to be utilized at once, accompanied with the capacity to monitor up to three independent process sample streams. In conjunction with monitoring different sample streams, the 3-Channel Sample Sequencer feature can also be used for sample line redundancy. In doing so, an additional safeguard to the facility's process is obtained. The ability to monitor, control, and combine data from multiple instruments into one, allows facilities to reduce purchases of redundant instrumentation; thus, providing instant capital savings, and eliminating any associated redundant O&M expenditures.

The Outfall SC's on-board automation serves multiple functions, allowing the instrument to be self-efficient, and reliable. The Outfall SC detects and initiates corrective actions to resolve potential sample flow issues throughout the device, as well as within the sample lines leading up to the device. Additionally, the Outfall SC's automation performs cleaning functions to all parts of the device, using automatic detection, or a user-defined cleaning schedule. Utilizing end-user controlled operational set points, the Outfall SC maintains specified flow rates 24/7, virtually eliminating the need of human involvement, and unscheduled shutdowns.

Engineered to be universal, the Outfall SC fulfills multiple needs by not limiting itself to any single installation environment, industry, or fluid analysis type. The Outfall SC is adaptable, interchangeable, and easily integrated into any manufacturing process, serving a multitude of process control parameters within several industries including but not limited to drinking water, wastewater, semiconductor, pharmaceutical, power, and pulp and paper.

Potential users will also benefit from the Outfall SC's capacity to provide Industry 4.0 to facilities across multiple industries. Built with the most technologically advanced automation and control systems available, the Outfall SC is designed to bring complete automation more easily to facilities across all manufacturing industries. Virtually wire-free, the Outfall SC easily incorporates into any manufacturing process, creating complete and instantaneous connectivity to all onsite process control instruments. The Outfall SC has the capacity to allow for data management to be carried out locally, or via cloud computing, and/or IoT.

The Outfall SC is supplemented with a pre-installed, universally written program covering multiple industries for automation control, as well as a cloud computing service provider with interchangeable data analytics software. With a maximum communication range of up to 40-miles, and a communication signal unaffected by building design or composite, the placement of the Outfall SC has virtually no boundaries The Outfall SC also contains its own backup power supply and is not reliant on Wi-Fi, cellular, or Bluetooth technologies for communication. In the event of a power outage, loss of cellular signal, or Wi-Fi, the Outfall SC will remain online, monitoring, and obtaining critical operational data.

These key features make the Outfall SC fully compatible and easily customizable to meet a wide range of operational requirements. Powered by the industry's most advanced automation and IoT solutions devices, this system is fully equipped with the latest technology for Industry 4.0. The Outfall SC allows any facility to harness the power of Industry 4.0, regardless of size or infrastructure age, to create streamlined pathways for data extraction, analysis, process control, information sharing, and corrective actions to be automatically carried out in real-time.

Applying the Outfall SC's technology allows for bringing machine automation; equipment connectivity; process visualization; predictive maintenance; advanced AI; big data storage; and industrial network security into a consolidated industrial process, attaining a level of operational efficiency within your manufacturing process never before capable of achieving. With the Outfall SC only requiring minimal onsite programming, hiring expensive third-party engineering firms, along with finding an affordable cloud service provider, is no longer required.

The Outfall SC's plug and play technology and design allows for scalability, providing potential manufacturers the ability to offer its customers flexibility in device connectivity capacity. End-users can further customize the automation program and embed site-specific requirements utilizing the Outfall SC's user-friendly HMI touch screen.

The Outfall SC allows users to experience the future of process control instrumentation, today. With the largest range of installation options and capabilities amongst any process control instrument on the market, the Outfall SC can easily be relocated throughout a facility as needed with minimal limitations. This flexibility allows end-users to leverage one or more of the Outfall SC's features that will best support operational needs within their manufacturing facility.

Process Control Instrument Features

Adaptable to any process control instrument containing the capacity/functionality for data communication, regardless of make, model, or application Minimizes the need to purchase new or additional process control instrumentation Use existing transmitters and sensor(s)

Turns aged instrumentation into the most technologically advanced

Reduce onsite instrumentation needed by up to 67%, by eliminating the need for redundant instrumentation purchases Allows for the analysis of three-independent sample streams that are monitoring the same parameter(s)

Reduces the required amount of space needed for process analysis

Reduces annual Operational and Maintenance costs

Connects, monitors, and controls instrumentation throughout a facility

Communication range up to 40-miles

Not effected by any architectural designs or construction materials

Independent communication link and power supply

Stays online during power interruptions

Increased communication reliability and stability

Not dependent on Wi-Fi, cellular, or Bluetooth communication technology

Built to withstand the harshest of environments

Flow cell and manifolds contain three layers of protection

Anodized and painted with an automotive water-based acrylic polyurethane enamel paint by MAZDA, providing superior protection against corrosion Top layer coated with a non-toxic, no VOC/SOC Tricopolymer sealant Plastic components constructed from Delrin (Acetal Homopolymer) plastic and HDPE (Polyethylene)

Chemical and impact resistant

Electronics housed within a NEMA 4× enclosure with temperature monitoring

Adaptable to multiple markets

Engineered to encompass a wider range of operating specifications and sample parameter analysis needs, meeting most sensor applications and sample requirements throughout multiple industries/markets (sample is not limited to only water analysis)

Onboard flow, pressure, and valve position monitoring:

Recognizes problems, troubleshoots, then takes corrective actions autonomously

Performs situation specific cleaning functions by monitoring indicators, and automatically taking corrective actions, all within minutes, while providing notification to end-users.

Reduces total amount of non-revenue water needed for cleaning operations

Preventative maintenance sequence is performed automatically to keep the process on-line, maintaining compliance Automated flow cell cleaning Utilizes clean water or other cleaning solution (dependent on the type of process sample being analyzed) to remove accumulation of foreign debris Boosts cleaning fluid pressure, providing pressurized fluid to 6 strategic locations Not dependent on the end-user's cleaning fluid pressure availability Clears blockages and decreases cleaning time Automatically controls signal outputs to eliminate the recording of false data Pre-programmed selections that are easily customizable to meet individual site requirements:

Automatic cleaning cycles

Customizable sample frequency selection

3-Channel Sample Sequencer to 3 sample stream options with adjustable frequencies and/or durations Manual Mode—Operate valves independently on command Proactive Mode—Automatically identifies, notifies, and resolves sample parameter requirements that fall outside of customizable set points, keeping the instrument online Allows automatic sample line backwashing followed by a complete system cleaning cycle to remove all foreign material Alarm activated due to low flow, low/high sample pressure, and/or sample level Alarm setpoints customizable Multiple safety feature conditions are embedded, such as:

Back pressure exceeds psi setpoint: operation is aborted, notifying end-users (alarms)

Monitoring if back pressure stabilizes beyond the allotted time setpoint

Reduces strain on sample pump

Extends service life of pump and other components

Energy efficient

Utilizes 24-V components

Ideal for remote installations

Contains a powerful backup power supply to keep system online for up to 3-hours, while the Outfall SC sends out alerts for immediate servicing requirements Built to withstand harsh environments Multiple sample inlet capacity Capable of cycling between three-independent sample streams at various timed frequencies Every 15, 30, 60, 120, or customizable minute interval Ensures sample representativeness by automatically operating central drain valve while increasing flow rate to turn-over sample within the flow cell quickly Minimizes unnecessary pumping by automatically returning sample flow to programmed rate when sample turnover is complete Provides the capacity for redundant sample lines, increasing safety and protecting against processes needing to go offline Automatically switches sample streams due to a loss in flow Outfall SC's sample feed is not limited to only insertion sensors Provides a monitored sample supply to external instrumentation that do not utilize insertion probes through an auxiliary sample port option Auxiliary sample port provides a sample feed rate of up to 8 L/min with adjustable pressure boosting capability up to 120 psi Design has the capacity to provide (2) auxiliary sample ports, doubling capacity potential Programmable automatic flow rate control Flow control valve automatically adjusts to maintain a desired pre-set flow rate Cleaner Data Low analyzer drift Data with greater accuracy and precision Provides a continuous, stable environment, customizable to match a sensor's sampling requirements to optimize its performance Increases sensor life Wide flow range capacity Suitable for multiple applications throughout many industries/markets Ability to withstand low and high flow rates 500 mL/min to greater than 30,000 mL/min Higher flow rates Obtain and monitor current sample/process conditions more precisely Reduces strain on sample pump, increasing its service life Allows for quicker process changes to occur, avoiding potential catastrophic process interruptions.

Lower flow rates

Suitable for flow sensitive sensors

Lighting System

Waterproof IP65 12V LED Flex Strip

60 LEDs/High-Density

Independent power supply

Ultra-small 12V rechargeable battery pack comprised of nickel metal hydride (400 mAH)

Onboard 120V to 12V converter for easy and quick charging of battery pack, or continuous power provided by the converter Allows for a quick, secondary performance check by visual observation of sample flowing through the Outfall SC's Cell, assuring current sample conditions are being monitored Choose from an array of colors and visual effects Controlled via Bluetooth or activated by utilizing an embedded power switch Technological Interfacing and Cloud Computing Features Connects and creates wireless 2-way communication with any onsite process control instrument containing the capacity and/or functionality for data communication Brings wireless connectivity to all process control instrumentation Allows facilities to link, control, and/or monitor real-time process data and alarms throughout the facility footprint (within 40 miles)

Analytics technology allows for predictive equipment failures, enabling optimizing of preventive maintenance programs Interfaces with: Cellular RTU, SCADA, Wi-Fi, MODUDBUS, and more Cloud computing Real-time data availability Real-time data analytics software (Analysis and predictive trending of real-time data, Automatic process control optimization)

Instant notifications via email, text, voice call

Trend analysis for preventative maintenance and process control forecasting

Cost-effective and adaptable

Enhanced business value and agility

Improves operational efficiency

Data storage

Artificial Intelligence (AI)

Voice recognition

IoT solution

Faster SSL Offload, Traffic Management, TCP Express, Connection Management, IoT Traffic Bifurcation Smarter Analytics and Visibility Programmability Policy Enforcement Access Control Protocol Analysis Safer: Comprehensive Security, Network, Subscriber Aware Firewall, Authentication and Authorization, Intelligent DNS, and DDoS Protection The illustrative embodiments of fluid monitoring systems & methods disclosed herein may also offer a potential for further innovative technology. With its wireless communication, Cloud, and IoT capabilities, the Outfall SC can easily adapt and incorporate any communication technological advances into its operating technologies; thus, maintaining an unlimited potential for industrial application.

Illustrative Embodiment of Plc/Pac and Flow Cell Control Scheme

Generally, the PLC and/or PAC may be configured to select one or more flushing/cleaning operations described above based on a given set of predetermined conditions (e.g., measured flow rates and/or pressures, other sample fluid parameters, etc.) or based on user input, as well as control various other aspects of the flow cell 110 without limitation unless otherwise indicated in the following claims. Additionally, various check valves 113d may be utilized (such as those shown at least in FIG. 24C) to mitigate and/or eliminate any cross contamination between various sample fluids, wash fluids, etc. without limitation unless otherwise indicated in the following claims.

In an illustrative embodiment, the PLC and/or PAC may be configured to control any on-board valving and/or other fluid handling components of the flow cell 110. Additionally, the PLC and/or PAC may be configured to receive information from outside process control instruments, package that data, send that data to a cloud provider, from where the data may either be sent to various mobile applications via integration of a smart device and/or mobile computing device or to an operating screen positioned adjacent the flow cell 110 to provide a visualization of live data. The data may be supplied to software for purposes of data analytics that may identify and/or compile conditions for artificial intelligence to identify trends, alarm set points determined by a user, etc., or directly control process control devices For example, a chlorine analyzer may be set for a low of 3 ppm and a high of 4 ppm. The software may be configured to keep the value at 3.5 ppm, wherein the data may be transmitted to the PLC and/or PAC on the flow cell 110 (which transmission may be achieved via wired and/or wireless connections including but not limited to Bluetooth, cellular connection, radio frequency, various 802.11 protocols, or any suitable method and/or structure without limitation unless otherwise indicated in the following claims).

Once the PLC and/or PAC receives that data, the PLC and/or PAC may be configured to transmit that data to a DA and C and/or PLC (which may be referred to as a gateway in portions of the present disclosure, either wired or wirelessly without limitation unless otherwise indicated in the following claims, which gateway may communicate with all instrumentation or a portion of the instrumentation and/or components associated with the flow cell 110. In one illustrative embodiment the gateway may use 4-20 mA connection as well as RS-232, but the optimal configuration may depend on the specific application and industry. Accordingly, the scope of the present disclosure is in no way limited by the specific gateway and/or presence thereof unless otherwise indicated in the following claims. The gateway may relay data back to the analyzer that is controlling a certain process point (i.e., a chlorine analyzer in this example), which may allow a chemical dosing pump connected to the chlorine analyzer (or a user) to adjust process variables in real time through the cloud to data analytics software and back to the associated analyzer to adjust a specific process variable by a desired amount. These various components may be configured to allow a user to utilize a plurality of analyzers, compile various types of data, communicate with various other components or devices, etc.

As mentioned above, the illustrative embodiment of a flow cell 110 may be used to reduce the amount of instrumentation at a given facility (e.g., oxidation reduction potential, pH, temperature, organic load, etc.). This may be achieved through providing more than one sample fluid inlet lines 111 to a given main chamber 120 and associated instrumentation and/or components. Each sample fluid inlet line 111 may be associated with a separate sample fluid source (e.g., three sedimentation basins). The sample fluid inlet lines 111, associated valving and fluid handling components, and the operation thereof may be programmable via the HMI (e.g., the number of sample fluid inlet lines 111, frequency for change from one sample fluid inlet line 111 to another, the amount of time a specific sample fluid inlet line 111 is selected, etc.) and/or associated PLC and/or PAC.

What follows is one illustrative embodiment of various control schemes, set points, logic statements, etc. for a flow cell 110 and/or PLC and/or PAC engaged therewith. Any specific values, variables and/or values thereof, logic statements, set points, etc. listed below are for illustrative purposes only, and the optimal configuration of the flow cell 110, PLC and/or PAC engaged therewith may vary from one application to the next. Accordingly, the illustrative embodiments described below are in no way limiting to the scope of the present disclosure unless otherwise indicated in the following claims.

Illustrative Embodiment of Flow Cell Capability, Advantages, and/or Features (Minus Cloud Computing)

What follow are various capabilities, advantages, and/or features of an illustrative embodiment of a flow cell 110, PLC and/or PAC, and/or component of a flow cell 110 and/or PLC and/or PAC such as those described herein above and/or variations thereof. Additionally, various set points, PLC and/or PAC actions, automation, and/or programming responses to certain parameter values, etc. are described for an illustrative embodiment of a flow cell 110 and connected PLC and/or PAC. However, the capabilities, advantages, set points, PLC and/or PAC actions, automation, programming responses, and/or features described below are not limiting to the scope of the present disclosure unless otherwise indicated in the following claims.

In an aspect, the flow cell 110 may optimize any insertion sensor's functionality and data reliability by eliminating interferences caused by flow disruptions and accumulation of organic/inorganic sediment within the measuring chamber. Disruptions in flow might consist of continuous fluctuation in flow rates, inadequate flow for proper sample turnover, or complete loss of sample flow, while the accumulation of sediment and/or other foreign contaminates can quickly interfere with a sensor's performance, all providing the end-user with false data. Too often these interferences often go unnoticed until a sensor fails, or an end-user cleans the instrument. Meanwhile, any facility relying on the potentially false or inaccurate data from an impaired sensor to make critical changes in their operations is at a minimum not optimized while potentially facing catastrophic results.

The Outfall Smartcell (referred to as "flow cell 110" above and "O.S.C.," "flow cell 110," or "Outfall" below) creates an ideal environment in which sensors can monitor, one tailored to precisely meet and maintain sample specifications continuously, thus maximizing the performance and service life of the sensors. By being self-efficient and capable of diagnosing and resolving internal issues autonomously, the O.S.C. ensures process optimization, reduction in unplanned shutdowns, increase in safety, and cost savings can all be achieved simultaneously.

Overview

The O.S.C. contains three-sample supply line connections (making up the Sample Stream Sequencer) that provides the end-user with the ability to monitor up to three separate process sample supply lines that share the same parameters to be monitored. Alternatively, two of the sample supply lines can also be used proactively to provide redundancy of a single process sample, giving additional layers of continuous flow protection.

One of the three ball valves within the Sample Supply Sequencer will be open (allowing the desired sample stream into the monitoring chamber), while the O.S.C. is in operation. The Programmable Logic Controller (PLC) and/or programmable automation controller (PAC) keeps the other two ball valves closed until the end-user's elected monitoring period is met for the currently active sample stream. Moments prior to the Sample Supply Sequencer switching to a different sample stream, all local signal outputs are placed on "Hold." Once the open ball valve is fully closed, the next channel's ball valve opens, allowing the elected sample stream into the monitoring chamber. Before the "Hold" is removed from the local signal outputs, the O.S.C.'s internal sample plumbing and monitoring chamber is flushed with the newly elected sample stream. This aids in eliminating cross contamination between sample streams.

The type and number of sensors within the monitoring chamber of the O.S.C. is dependent on the end-user's needs, as well as the manufacturer who takes ownership of the O.S.C. Sensor size and sample requirements will determine how many parameters (different sensors) can be used at the same time. Larger insertion sensors will require more space within the O.C.S.'s sensor cap. Additionally, sensors requiring a slower flow rate may not be compatible with sensors or applications that require higher flow rates, which may affect the specific sensors that may be used with one another.

To ensure sample fluid remains continuously flowing through the system without any uncontrolled interruptions autonomously, each sample supply line is monitored by the same host of internal sensors (flow meter, flow switches, level detector, and pressure sensors). The rate of flow for all three sample supply lines is controlled by one proportional modulating ball valve. The proportional modulating ball valve adjusts flow based off the measured flow rate of the flow meter. This information is sent to the PLC and/or PAC, which in turn adjusts the proportional modulating ball valve's 4-20 mA signal; thus, changing the proportional modulating ball valve's position accordingly. Rate of flow is programmable at the instrument's interface by the end-user. While the O.S.C. processes data from all process control instruments that have been connected by the end-user[1], the O.S.C. is simultaneously processing all internal sensor data[2]. The PLC and/or PAC analyzes the individual internal sensor data, and/or specific combinations of the collected sensor data, to maintain user-defined setpoints and operational requirements. The analyzed data allows the PLC and/or PAC to make informed decisions on its own, making it capable of recognizing, troubleshooting, and taking corrective actions if needed. For example, assume a situation in which the flow rate of a fluid through the system begins to deviate outside of the user-defined setpoint(s). A gradual decrease/increase or abrupt drop/spike in the rate of flow causes a succession of actions, which are dependent on the event taking place. A deviation outside the user-defined flow setpoint(s) triggers a response, initiating actions with the end goal of maintaining sample flow as closely to the user-defined setpoint(s) as possible, without the need for human intervention.

[1]. Process control instrumentation connected to the O.S.C. is categorized as "remotely" (uses an independent sample supply and communicates with the PLC and/or PAC through the Gateway) or "locally" (dependent on the O.S.C.'s sample supply and communicates to the PLC and/or PAC through a direct connection).
[2]. "Internal" refers to all onboard functions, components, sensors, and/or data that make up the O.S.C., allowing for autonomous operations. In other words, any function, sensor, or component that comes with the O.S.C.

IF: the flow meter captures a rapid drop or spike in the rate of flow that is greater than +/−10% of the user-defined flow setpoints, AND this change of flow is sustained for greater than 5-seconds, the PLC and/or PAC may be configured to instruct the proportional modulating ball valve to compensate for the detected change in flow. This is achieved by the PLC and/or PAC adjusting the proportional modulating ball valve's 4-20 mA signal to accommodate for the degree of percentage of change (greater than +/−10%), maintaining the end-users set flow rate.

IF: A gradual decrease or increase in flow is recognized, and the change in flow reaches +/−5% of the end-users set flow rate[3], the PLC and/or PAC may be configured to instruct the proportional modulating ball valve to compensate for the detected change in flow. Once again, the PLC and/or PAC adjusts the proportional modulating ball valve's 4-20 mA signal to accommodate for the degree of percentage of change monitored (greater than +/−5%), maintaining the end-user's set flow rate.

[3]. Sample flow rate's setpoint is adjustable at the interface by the end-user with a programmable range of 500-30,000 mL/Min (0.5-30 l/Hr).

In the event any of the three sample stream supply lines cause the proportional modulating ball valve to open greater than or equal to 85%[4] of its capacity in order to maintain the end-user's setpoint, OR the sample pressure[5] becomes less than or equal to the end-user's set point, the following actions may be triggered:

[4]. 85% is the trigger point to allow for the sample to continue to be monitored until help arrives, in the event all automatic corrective actions fail to resolve issue. This value can be disabled by the end-user at the Outfall's interface for applications requiring high flow rates.
[5]. Sample pressure's setpoint is adjustable at the interface by the end-user with a programmable range of 0-150 PSI.

A. The instrument and/or cloud computing service keeps the end-user informed with real-time updates via text, call, or email. The type of communication performed is selectable by the end-user on the Outfall's HMI interface:
        i. Text
        ii. Voice Call
        iii. Email
    B. The integrity of the data is maintained by controlling all signal outputs (locking and unlocking) of the end-user's transmitter that is directly connected (sensors that are placed into the measuring chamber of the Outfall).

Note: The Outfall can manage data and control external devices/process analyzers that are not utilizing its flowcell and/or devices/process analyzers that are using its flowcell[6].

[6]. The Outfall's onboard automation is only useful for analyzers that are utilizing its flowcell to house their sensors. These are referred to as "local" instruments. For all other devices connected to the Outfall, this is to bring connectivity, visibility, and optimization to the entire plant.

For process control instruments that are not, communication occurs by connecting to a DA&C/PLC and/or other gateway device either hard lining the 4-20 mA signal(s), or by means of other communication protocols, such as Modbus RTU. The DA&C/PLC and/or gateway device sends this data to the PLC and/or PAC via cellular connection and/or a standalone RF (radio frequency) modem. The PLC and/or PAC then sends information back to the transmitter following the same mode of communication, or by the gateway can communicating back to the process control device using customizable I/O options. When utilizing the cloud computing feature, a communication link may be utilized (which may be built within the PLC and/or PAC) for sending the packaged data to a cloud computing service provider via cellular connection. Analyzed data from data analytics software returns to the Outfall SC's PLC and/or PAC, returning data back to the process control instrument, providing automatic process changes based on end-user setpoints.

Prior to performing switching of sample stream supply lines, general maintenance functions, taking corrective actions, and/or executing proactive measures, the signal outputs of all sensors being utilized within the Outfall's measuring chamber are placed on "hold". Because the ability to put all transmitters on "hold" is not an option, the signal output (4-20's) must be placed into "hold" status by the PLC and/or PAC once the data is received from the analyzer's transmitter connected to the Outfall. The analyzer's transmitter is either connected to the Outfall directly (utilizing our flow cell and wired directly into the PLC and/or PAC) or indirectly (using the gateway, as well as their own sample supply/flow cell).

Before using the Outfall Smartcell, the end-user will program how many sample stream supply lines (1-3) are being utilized via the HMI screen. This will guide the PLC and/or PAC on actions it needs to take in certain situations. For example, initiating the backwash feature, which clears out any sample line that is being utilized (up to 3 individual lines). If only one sample line is being used, the end-user would program just that, along with which line is being used, labeled 1 through 3, 1 being the primary line by default. This would tell the PLC and/or PAC upon performing a backwash not to try backwashing any unused sample lines.

Backwash Operation

This operation utilizes the pressurized 'clean fluid' supply system to clear blockages within the sample lines leading to the Outfall's inlet connections. During a backwash cycle, backpressure on the sample manifold, as well as the clean fluid manifold, is monitored by pressure sensors in each manifold. The backwash flow switch is also used to verify that Backwash Solenoid Valve Tag 3 (BSV 3) is properly functioning via a water flow rate indicator, signifying that the blockage is being cleared.

C. If pressure exceeds 100 psi for longer than 60 seconds, the cycle is aborted as an embedded safety feature to protect critical components, as well as to maximize service life (this time frame is a default value, customizable by the end-user to accommodate for longer sample line installations, as well as larger ID sample tubing/piping).
  i. If the program is aborted:
    a. A full cleaning cycle is automatically initiated after a sample line backwash operation is activated, and
    b. Operations are immediately notified via end-user defined communication methods of text, email, or call.
  ii. From here, the end-user can define from the interface if the Outfall should:
    a. Automatically switch to the next available sample stream supply line (if utilized). If additional sample stream lines are available: (1) The Outfall will automatically switch sample stream supply lines to the next sample line in sequence (An override function is available for the end-user to allow the Outfall to proceed with analyzing the troubled sample stream, allowing the modulating flow control ball valve to open 100%); and (2) Alerts are sent notifying operations of actions performed, as well as requesting service as soon as possible, OR
    b. Continue repeating the backwash process until blockage has been cleared and/or help arrives.

D. If the program successfully completes a backwash cycle, indicated by the sample manifold pressure sensor and the clean fluid manifold's pressure sensor stabilizing at a psi value within +/−10% of each other for a duration of 60-seconds, but the flow problem still exists once the PLC and/or PAC starts to refill the measuring chamber:
  i. A full cleaning cycle is automatically initiated.
  ii. Alerts are sent notifying operations of status, actions performed, as well as next actions it will carry out.
  iii. If problem still exists after the full cleaning cycle, the Outfall follows steps C.ii.a.1. through C.ii.a.2. listed above.
  iv. If step C.ii.a. is not available, then the Outfall follows steps H.i. through H.ii.b.1.

E. If program successfully completes the cycle and resolves the issue:
  i. The Outfall quickly fills up the measuring chamber, re-establishes the user-defined flow rate, and removes the "hold" status on any local[7] signal output, placing them back in "active" status.
    [7]. Local refers to any sensor that is utilizing the Outfall's measuring chamber for water analysis. All other connected instruments utilizing the gateway remain unaffected.
  ii. Alerts are sent notifying operations of status and actions performed, as well as conveying no further action is needed at this time.

G. If the flow rate drops below 750 mL/minute at any time:
  i. A sample line backwash operation is initiated followed by a full cleaning cycle.
  ii. If backwashing and the full cleaning cycle do not result with the sample flow being greater than 750 mL/minute, the next sample stream supply line in sequence, if utilized, is automatically switched over to, operations are notified of actions performed, and service is requested as soon as possible.

H. If no other sample stream supply lines are being utilized, and the Outfall has exhausted all options:
  i. A fatal alarm is sent to operations, requesting service immediately.
  ii. The Outfall will then continue repeating the process of attempting a backwash and performing a full cleaning cycle until:
    a. The Outfall resolves the issue and adequate flow is re-established, at which point operations are immediately notified via communication choice of text, email, or call stating actions performed, as well as cancelling its service request and all signal outputs are taken off "hold" and are now "active"; OR
    b. Help arrives and, utilizing the "Pause" selection button within the "Service" category of the HMI screen available for the end-user to select upon arrival the Outfall continues holding only the signal outputs coming from the sensors that monitor the sample within the Outfall's measuring chamber. All other signal outputs coming from other instrumentation are on independent sample stream supply lines and their monitoring and operating proceed normally.

End-Users' Responsibility in Order to Utilize the Sample Line Backwash Feature

Responsible for acquiring and setting up bypass valving on the effluent side of their sample pump. Running a hardwire back to the PLC and/or PAC may be utilized, but not necessary, since this connection can be made utilizing the Outfall's cellular connection feature.

Setup on End-User's Side

Water is diverted on the effluent side of the sample pump leading to waste by opening a Bypass Valve 1.

Waste Bypass Valve 2 on the immediate downstream side of Bypass Valve Tag 1 is then opened, leading to waste.

End-User Selects if the Sample Line Backwash Feature is Enabled or Disabled at the HMI If the feature is enabled within the HMI, the PLC and/or PAC will send an analog and digital signal to operate valves (and pump if capable) during the times laid out below.

Automation Steps for Sample Line Backwash for Resolving Sample Flow/Pressure Issues 1. Local signal outputs are placed on "Hold".
2. Proportional modulating ball valve used for flow control is closed.
3. Secondary drain ball valve opened.
4. Clean Fluid Master Solenoid Valve Tag 19 (CFMV 19) on the influent side of the wash fluid manifold is opened.
5. Backwash Solenoid Valve Tag 3 (BSV 3) on wash manifold opened.
6. Clean fluid pressure booster pump activates automatically via PAC or when sample flow is recognized. System may be independent from the PLC and/or PAC.
7. 3-Channel Sample Stream Sequencer ball valves 1, 2, or 3 are individually opened, depending on which sample line was being used while triggering a backwash. The other 2 ball valves will remain closed.
8. BSV 3's successful operation of pressurized clean fluid passing through the valve is monitored by utilizing the Backwash Flow Switch. Under normal conditions, the initial surge of pressurized wash fluid will activate this flow switch, which then turns off or slows down due to the wash sample having no/limited flow until the clog is cleared.

If the Backwash Flow Switch does not activate when BSV 3 is opened, the pressure from both pressure sensors may be compared to determine if flow is moving through as intended. If flowing, pressure sensors will be equalized. If so, the Backwash Flow Switch is stuck in the off position. In this event if the pressure (psi), as monitored by sensors on the sample manifold and the clean fluid manifold is within +/−15% of each other, then the flow switch is stuck, and the backwash procedure will proceed. Alerts will be sent notifying operations of actions performed, as well as requesting service on the Backwash Flow Switch as soon as possible.

9. After 60 seconds (default—customizable by end-user using the HMI touch screen panel to compensate for sample line length), OR 60 seconds after the backwash flow switch reactivates (signifying the clean fluid has broken through the clog), BSV 3 on wash manifold closes.
10. CFMV 19 on the wash manifold closes.
11. The clean fluid pressure booster pump automatically deactivates when sample flow stops.
12. Waste Bypass Valve 2 on the downstream side of the Bypass Valve 1 is closed (customer side).
13. Water is diverted back on the effluent side of the sample pump by closing Bypass Valve. If pump is controlled remotely, a signal would then at this point need to be sent to turn the pump back on (customer side).
14. Proportional modulating ball valve is opened to 90% flow capacity.
15. One minute after the proportional modulating ball valve opens to 90%, allowing time for the sample line to fully expel the clean fluid wash from its line and be pushed through the Outfall's secondary drain, the secondary drain's ball valve closes. Time duration is customizable at the HMI to compensate for longer sample line length.
16. Once the ultrasonic level sensor detects the sample level within the measuring chamber is at a depth of 4", the PLC and/or PAC directs the proportional modulating ball valve to re-establish the end user's flow rate setting, as compared to the flow indicated from the Smart Magmeter (flow meter).
17. Once the user-defined flow rate has been re-established, and the sample level reaches a depth of 4.5", all local signal outputs are taken off "Hold" and placed into "Active" status.

Automation Steps for Sample Line Backwash During "Proactive Mode" Setting

This setting may be based off a schedule rather than an event. Programmable at the HMI, the end-user enters the cleaning frequency for the sample lines to be backwashed as a preventative measure.

1. Local signal outputs are placed on "Hold".
2. Proportional modulating ball valve used for flow control is closed.
3. Secondary drain ball valve opened.
4. CFMV 19 on the influent side of the wash fluid manifold is opened.
5. BSV 3 on wash fluid manifold opened.
6. Clean fluid pressure booster pump activates automatically via PAC or when sample flow if recognized. System may be independent from the PLC and/or PAC.
7. 3-Channel Sample Stream Sequencer ball valves 1, 2, and 3 are opened and flushed one at a time in sequential order by default, repeating steps 7 through 11.
8. BSV 3's successful operation of pressurized clean fluid passing through the valve is monitored by utilizing the Backwash Flow Switch. Under normal conditions, the initial surge of pressurized wash fluid will activate this flow switch, then flow should modulate, depending on the degree of sample line fouling/plugging.

If the backwash flow switch does not immediately activate when BSV 3 is opened, the pressure from both pressure sensors is compared to determine if flow is moving through as intended. If so, the Backwash Flow Switch is stuck in the off position. In this event if the pressure (psi), as monitored by sensors on the sample manifold and the clean fluid manifold, is within +/−15% of each other, then the flow switch is stuck, and the backwash procedure will proceed. Alerts will be sent notifying operations of actions performed, as well as requesting service on the Backwash Flow Switch as soon as possible.

9. During backwash the back pressure values, in psi, of the sample line and the clean fluid manifold sensors should remain relatively similar, +/−10%. A sudden drop or loss in the sample manifold's pressure while the clean fluid manifold's pressure remains relatively constant indicates BSV 3 failed, and the backwash operation is aborted. Alerts are then sent notifying operations of actions performed, as well as requesting service on the BSV 3 as soon as possible.
10. After 60 seconds of no change in pressure (+/−10%) and the backwash flow switch has not reactivated since the initial surge of flow, BSV 3 on the clean fluid manifold closes (60 seconds=default—customizable by end-user using the HMI touch screen panel to compensate for sample line length or size); OR, In addition to any elapsed time from step 10, 60 more seconds are added after the Backwash Flow Switch reactivates (signifying the clean fluid has broken through the clog).
11. If other sample stream supply lines are being utilized, the current sample stream supply line's ball valve closes, and the next sample stream supply line's ball valve opens in sequential order, repeating the automation steps listed under "Automation Steps for Sample Line Backwash for Resolving Sample Flow/Pressure Issues" for each sequence.
12. CFMV 19 on the wash manifold closes.
13. The clean fluid pressure booster pump automatically deactivates when sample flow stops.
14. Waste Bypass Valve 2 on the downstream side of the Bypass Valve 1 is closed (customer side).
15. Water is diverted back on the effluent side of the sample pump by closing Bypass Valve. If pump can be controlled remotely, a signal would then at this point need to be sent to turn the pump back on (customer side).
16. Proportional modulating ball valve is opened to 90% flow capacity.
17. One minute after the proportional modulating ball valve opens to 90%, allowing time for the sample line to fully expel the clean fluid wash from its line and be pushed through the Outfall's secondary drain, the secondary drain's ball valve closes. Time duration is customizable at the HMI to compensate for longer sample line length.
18. Once the ultrasonic level sensor detects the sample level within the measuring chamber is at a depth of 4", the PLC and/or PAC directs the proportional modulating ball valve to re-establish the end-users flow rate setting based off the flow indicated from the Smart Magmeter (flow meter).
19. Once the user-defined flow rate has been re-established, and the sample level reaches a minimum of 4.5", all local signal outputs are taken off "Hold" and placed into "Active" status.

Safety Feature Conditions

If back pressure exceeds "100" psi; OR, back pressure's peak point stabilizes for longer than 60 seconds (safety setpoint of 60 seconds can be disabled by the end-user utilizing the HMI if sample lines require a longer flush time due to size and distance), along with the sample manifold's flow switch indicating no flow (not activated) THEN the Outfall Smartcell aborts operation and notifies the end-user via alarms.

Cleaning Operation

Flow, pressure, and valve monitoring allows full automation of the system for cleaning by monitoring and independently taking corrective actions, all within minutes, while providing notification to end-users. Preventative maintenance may be performed automatically to keep the process on-line.

Cleaning frequency scheduling or enabling manual mode (forced cleaning cycle) are programmable by end-user utilizing the instrument's HMI.

1. Local signal outputs placed on "Hold".
2. Secondary drain valve opened.
3. Last used sample stream supply line's ball valve is closed.
4. Close proportional modulating ball valve.
5. CFMV 19 on the wash manifold opens.
6. Solenoid Valve Tag 2 opens (right sample port flush).
7. After 60-seconds, Solenoid Valve Tag 2 closes.
8. Solenoid Valve Tag 5 opens (left sample port flush).
9. After 60-seconds, Solenoid Valve Tag 5 closes.
10. Solenoid Valve Tag 1 opens (right sprayer).
11. After 60-seconds, Solenoid Valve Tag 1 closes.
12. Solenoid Valve Tag 6 opens (left sprayer).
13. After 60-seconds, Solenoid Valve Tag 6 closes:
    a. If clean fluid manifold's pressure is greater than 45 PSI, valve Tag's 1 and 6 can open simultaneously.
    b. During normal operation, valve Tag's 1 and 6 will open together, and after 60-seconds, they will close together.
14. Solenoid Valve Tag 4 opens (well flush).
15. After 60-seconds, Solenoid Valve Tag 4 closes.
16. CFMV 19 on the wash manifold closes.
17. The previously used sample stream supply line's ball valve is re-opened.
18. The proportional modulating ball valve is opened to 90% flow capacity.
19. One minute after the proportional modulating ball valve opened to 90% flow capacity, the secondary drain's ball valve closes. This allows rinsing to be performed so no cross contamination between samples or cleaning fluid occurs.
20. Once the ultrasonic level sensor detects the sample level within the measuring chamber is at a depth of 4", the PLC and/or PAC directs the proportional modulating ball valve to re-establish the end-users flow rate setting, as compared to the flow indicated from the Smart Magmeter (flow meter).
21. Once the user-defined flow rate has been re-established, and the sample level reaches a minimum operating height of 4.5", all local signal outputs are taken off "Hold" and placed into "Active" status.

Sample Selection Operation

Choice of utilizing up to three different sample supply feeds. Sample Supply Valve Tag 1 is the primary valve, which is normally open. The valves for supply feed lines are normally closed. Sample selection can rotate in sequential order on various timed frequencies, such as every 15, 30, 60, 120-minutes, or customizable minute/hour/day intervals. This is also programmable at the Outfall's interface by the end-user. When sample supply feeds change, the following actions are taken:

1. Local signal outputs are placed on "Hold".
2. Secondary Drain Valve opens.
3. The currently active (valve open) sample supply valve closes, while simultaneously opening the next sample supply valve to be utilized.
4. The Proportional Modulating Ball Valve is opened simultaneously with step 3 to 90% its flow capacity.
5. Secondary Drain Valve closes once the ultrasonic level sensor detects the measuring chamber's level to be empty.
6. The ultrasonic level sensor detecting the sample level within the measuring chamber to be at a depth of 5" triggers the Secondary Drain Valve to open.
7. Secondary Drain Valve closes once the ultrasonic level sensor detects the measuring chamber's level to be empty.
8. Once the ultrasonic level sensor detects the sample level within the measuring chamber is at a depth of 4", the PLC and/or PAC directs the Proportional Modulating Ball Valve to re-establish the end-users flow rate setting, as compared to the flow indicated from the Smart Magmeter (flow meter).
9. Once the user-defined flow rate has been re-established, and the sample level reaches a minimum operating depth of 4.5", all local signal outputs are taken off "Hold" and placed into "Active" status.

Additional capabilities, advantages, and/or features of a flow cell 110, PLC and/or PAC, and/or component thereof may include but are not limited to those listed below unless otherwise indicated in the following claims.

Generally, the disclosure herein may provide a process analyzer system that is adaptable to all analyzers, regardless of make, model, application, or industry, bringing machine automation, equipment connectivity, process visualization, predictive maintenance, and industrial network security into any and all businesses throughout the Process Industry. The Outfall Smartcell is a turn-key solution, allowing for a network of machines to digitally connect with one another, creating the ability to execute changes within a process in real-time, resulting in the true power of Industry 4.0.

On-Line Analytical Process Instrument

The illustrative embodiments of the flow cell 110 may be adaptable to most existing analyzer setups that contain capacity and/or functionality for data communication, regardless of make, model, or application. This may allow a user to use the existing transmitter and sensor(s) and may reduce the amount of instrumentation needed by half. This may allow for the analysis of two independent sample streams that are monitoring the same parameter(s), reduce the required amount of space needed, reduce annual operational and maintenance costs, and minimize the need to purchase new or additional process analyzers.

The illustrative embodiments of the flow cell 110 may be built to withstand the harshest of environments via annodizing of an entire aluminum block, which may be coated with non-toxic Tricopolymer sealant. Any plastic components may be constructed out of Delrin (Acetal Homopolymer). The flow cell 110 may be adaptable to multiple markets and engineered to contain a wide range of operating specifications, meeting most sensor requirements, for multiple applications throughout numerous industries/markets.

Flow, pressure, and valve monitoring may allow for full automation of the system for cleaning by monitoring and independently taking corrective actions, all within minutes, while providing notification to end-users. This may also allow for various preventative maintenance actions to be performed automatically to keep the process on-line. Additionally, such a configuration may allow for selection of pre-programmed automatic cleaning cycles, frequencies, and/or durations.

The illustrative embodiments of a flow cell 110 may be operated in a manual mode wherein a user may operate valves independently on command and may be operated in a proactive mode. In a proactive mode the flow cell may be configured to automatically identify, notify, and/or resolve sample requirements that fall outside normal operation, keeping the instrument online, and may be configured to provide automatic sample line backwashing followed by sample port flushing. In such an automatic configuration the flow cell 110 may be configured to provide an alarm activated due to low flow, alarm setpoints that may be customizable, and safety feature conditions (e.g., back pressure exceeds "50" PSI, aborts operation, notifies end user (alarms), back pressure peak point stabilizes for longer than 10 seconds, etc.).

The illustrative embodiments of a flow cell 110 may be energy efficient utilizing a 24-V battery source and low power valving, which may be ideal for remote installations and provide for longer lasting valves and/or other components. The illustrative embodiments of a flow cell 110 may be sealed and/or un-sealed flow cell housing to accommodate a wide range of sensor technologies and may have at least dual sample inlet capacity. The dual sample inlet capacity may provide the ability to cycle through two separate sample streams, the capability of cycling between two independent sample streams at various timed frequencies (e.g., every 15, 30, 60, 120, or custom minute intervals), and may be configured to automatically operate a central drain valve, while increasing flow rate, to turn sample over inside the flow cell quickly (an may automatically return sample to programmed flow rate when sample turnover is complete).

The illustrative embodiments of a flow cell 110 may be configured to allow a user to adjust a programmable automatic flow rate control such that the sample inlet valve automatically adjusts to maintain a set flow rate and may also be configured to allow for a wide flow range capacity, suitable for multiple applications throughout more industries/markets.

Technological Interfacing

The illustrative embodiments of the flow cell 110 may be configured to communicate with any analyzer or other asset that contains data communication protocol(s). This may allow the user to link, control, and/or monitor real-time process analyzer data, alarms, as well as the functioning of other major components, throughout a facility. This may allow a user to predict equipment failures and provide process automation.

Because the illustrative embodiments of the flow cell 110 may be configured to accommodate cloud computing functionality, the flow cell 110 may provide a turn-key solution and facilitate various data analytics capabilities across a wide range of industries as previously discussed above. Generally, as described herein various illustrative embodiments of a flow cell 110 may be allow for full or nearly complete automation of one or more processes. The data transmission, analysis, and action feedback directions as disclosed herein (and illustrative embodiments of which and/or components thereof are shown in FIGS. 26A & 26B) may be applied to other analyzers, equipment, processes, etc. (other than the flow cells 10, 110 as disclosed herein) without limitation unless otherwise indicated in the following claims. The data analytics capabilities may include access to real-time data, instant notification via email, text, voice call, etc., and/or trend analysis for preventative maintenance without limitation unless otherwise indicated in the following claims. The results may include a more cost-effective and flexible solution, enhanced business value and agility, and/or an improvement in operational efficiency without limitation unless otherwise indicated in the following claims.

Having described various preferred and illustrative embodiments of a fluid monitoring system and associated flow cell 10, 110 and retrofit kit, various advantages and preferred and illustrative embodiments of methods of use thereof will be apparent to those skilled in the art in light of the present disclosure.

Although the systems and methods described and disclosed herein may be configured as a retrofit kit to install on a prior art flow cell, the scope of the present disclosure, any discrete process step and/or parameters therefor, any apparatus for use therewith, and/or any component thereof is not so limited and extends to any beneficial and/or advantageous use thereof without limitation unless so indicated in the following claims.

The materials used to construct the apparatuses and/or components thereof may vary depending on the specific application thereof, but it is contemplated that polymers, synthetic materials, metals, metal alloys, natural materials, and/or combinations thereof may be especially useful in some applications. Accordingly, the above-referenced elements may be constructed of any material known to those skilled in the art or later developed, which material is appropriate for the specific application of the present disclosure without departing from the spirit and scope of the present disclosure unless so indicated in the following claims.

Having described preferred aspects of the various apparatuses, components thereof, and methods, other features of the present disclosure will undoubtedly occur to those versed in the art, as will numerous modifications and alterations in the embodiments and/or aspects as illustrated herein, all of which may be achieved without departing from the spirit and scope of the present disclosure. Accordingly, the methods and embodiments pictured and described herein are for illustrative purposes only, and the scope of the present disclosure extends to all apparatuses, components thereof, and/or methods for providing the various benefits and/or features of the present disclosure unless so indicated in the following claims.

While the various systems, methods, and components used therewith according to the present disclosure have been described in connection with preferred aspects and specific examples, it is not intended that the scope be limited to the particular embodiments and/or aspects set forth, as the embodiments and/or aspects herein are intended in all respects to be illustrative rather than restrictive. Accordingly, the processes and embodiments pictured and described herein are no way limiting to the scope of the present disclosure unless so stated in the following claims.

Although several figures are drawn to accurate scale, any dimensions provided herein are for illustrative purposes only and in no way limit the scope of the present disclosure unless so indicated in the following claims. It should be noted that the fluid monitoring systems & methods, flow cell 10, 110, retrofit kit, and/or components thereof are not limited to the specific embodiments pictured and described herein, but rather the scope of the inventive features according to the present disclosure is defined by the claims herein. Modifications and alterations from the described embodiments will occur to those skilled in the art without departure from the spirit and scope of the present disclosure.

Any of the various features, components, functionalities, advantages, aspects, configurations, process steps, process parameters, etc. of an apparatus or method disclosed herein may be used alone or in combination with one another depending on the compatibility of the features, components, functionalities, advantages, aspects, configurations, process steps, process parameters, apparatuses, etc. Accordingly, a nearly infinite number of variations of the present disclosure exist. Modifications and/or substitutions of one feature, component, functionality, aspect, configuration, process step, process parameter, components, etc. for another in no way limit the scope of the present disclosure unless so indicated in the following claims.

It is understood that the present disclosure extends to all alternative combinations of one or more of the individual features mentioned, evident from the text and/or drawings, and/or inherently disclosed. All of these different combinations constitute various alternative aspects of the present disclosure and/or components thereof. The embodiments described herein explain the best modes known for practicing the apparatuses, methods, and/or components disclosed herein and will enable others skilled in the art to utilize the same. The claims are to be construed to include alternative embodiments to the extent permitted by the prior art.

Unless otherwise expressly stated in the claims, it is in no way intended that any process or method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including but not limited to: matters of logic with respect to arrangement of steps or operational flow; plain meaning derived from grammatical organization or punctuation; the number or type of embodiments described in the specification.

What is claimed is:

1. A fluid monitoring system comprising:
   a. a sample fluid inlet;
   b. a flow cell comprising:
      i. a main chamber comprising:
         1. a first end wall on a first side of said main chamber;
         2. a second end wall on a second side of said main chamber opposite side first side;
         3. a front wall extending between said first end wall and said second end wall;
         4. a secondary drain positioned between said first and said second end walls and on a first side of said front wall, wherein said secondary drain is positioned below a top edge of said front wall;
         5. a first ramp extending from an area adjacent said first end wall to said secondary drain, wherein said first ramp is angled downward toward said secondary drain;
         6. a second ramp extending from an area adjacent said second end wall to said secondary drain, wherein said second ramp is angled downward toward said secondary drain;
         7. a sample fluid inlet port positioned between said first and second end walls;
         8. a first cleaning nozzle positioned in said first end wall;
         9. a second cleaning nozzle positioned in said second end wall;
         10. a primary drain positioned on a second side of said front wall, wherein said primary drain is positioned below said top edge of said front wall;
      ii. a base plate engaged with a bottom surface of said main chamber, said base plate comprising:
         1. a main inlet in fluid communication with said sample fluid inlet line; and,
         2. a base plate inlet in fluid communication with said main inlet and said sample fluid inlet port in said main chamber;
      iii. a sensor positioned adjacent said main chamber.

2. The fluid monitoring system according to claim 1 wherein said flow cell further comprises a cover engaged with a top surface of said main chamber.

3. The fluid monitoring system according to claim 1 further comprising an auxiliary sample system.

4. The fluid monitoring system according to claim 1 wherein said front wall further comprises a fluid control guide.

5. The fluid monitoring system according to claim 1 further comprising a programmable logic controller (PLC), wherein said PLC is in communication with said sensor.

6. The fluid monitoring system according to claim 5 wherein said PLC is configured with a wireless communication module.

7. The fluid monitoring system according to claim 1 further comprising a programmable automation controller (PAC), wherein said PAC is in communication with said sensor.

8. The fluid monitoring system according to claim 7 wherein said PAC is configured with a wireless communication module.

9. A flow cell comprising:
  a. a main chamber comprising:
    i. a first end wall on a first side of said main chamber;
    ii. a second end wall on a second side of said main chamber opposite side first side;
    iii. a front wall extending between said first end wall and said second end wall;
    iv. a secondary drain positioned between said first and said second end walls and on a first side of said front wall, wherein said secondary drain is positioned below a top edge of said front wall;
    v. a first ramp extending from an area adjacent said first end wall to said secondary drain, wherein said first ramp is angled downward toward said secondary drain;
    vi. a second ramp extending from an area adjacent said second end wall to said secondary drain, wherein said second ramp is angled downward toward said secondary drain;
    vii. a sample fluid inlet port positioned between said first and second end walls;
    viii. a first cleaning nozzle positioned in said first end wall;
    ix. a second cleaning nozzle positioned in said second end wall;
    x. a primary drain positioned on a second side of said front wall, wherein said primary drain is positioned below said top edge of said front wall; and,
  b. a base plate engaged with a bottom surface of said main chamber, said base plate comprising:
    i. a main inlet in fluid communication with a sample fluid inlet line; and,
    ii. a base plate inlet in fluid communication with said main inlet and said sample fluid inlet port in said main chamber.

10. The flow cell according to claim 9 wherein base plate further comprising:
  a. a second base plate inlet; and,
  b. a sample fluid channel extending along a portion of the length of said base plate, wherein said sample fluid channel is in fluid communication with said main inlet, said base plate inlet, and said second base plate inlet.

11. The flow cell according to claim 10 wherein base plate further comprises a main wash fluid inlet, wherein said main wash fluid inlet is in fluid communication with said sample fluid channel and a wash fluid source.

12. The flow cell according to claim 11 wherein said base plate further comprises:
  a. a primary drain passage in fluid communication with said primary drain of said main chamber; and,
  b. a secondary drain passage in fluid communication with said secondary drain of said main chamber.

13. The flow cell according to claim 12 wherein said base plate further comprises a waste reservoir, wherein said waste reservoir is positioned in front of said front wall of said main chamber and below a top edge of said front wall, and wherein said primary drain passage is positioned on a first side of said waste reservoir.

14. The flow cell according to claim 13 wherein said front wall further comprises a fluid control guide.

15. The flow cell according to claim 14 wherein said flow cell further comprises a cover engaged with a top surface of said main chamber.

16. The flow cell according to claim 15 further comprising a sensor engaged with said cover.

17. The flow cell according to claim 16 further comprising an auxiliary sample system.

18. The fluid monitoring system according to claim 17 further comprising a programmable logic controller (PLC), wherein said PLC is in communication with said sensor.

19. A method comprising the steps of:
  a. selecting a sample fluid;
  b. providing said sample fluid to a sample fluid manifold, wherein said sample fluid manifold allows a user to select said sample fluid or a second sample fluid;
  c. routing said sample fluid through said sample fluid manifold to a flow cell, said flow cell comprising:
    i. a main chamber comprising:
      1. a first end wall on a first side of said main chamber;
      2. a second end wall on a second side of said main chamber opposite side first side;
      3. a front wall extending between said first end wall and said second end wall;
      4. a secondary drain positioned between said first and said second end walls and on a first side of said front wall, wherein said secondary drain is positioned below a top edge of said front wall;
      5. a first ramp extending from an area adjacent said first end wall to said secondary drain, wherein said first ramp is angled downward toward said secondary drain;
      6. a second ramp extending from an area adjacent said second end wall to said secondary drain, wherein said second ramp is angled downward toward said secondary drain;
      7. a sample fluid inlet port positioned between said first and second end walls;
      8. a first cleaning nozzle positioned in said first end wall;
      9. a second cleaning nozzle positioned in said second end wall;
      10. a primary drain positioned on a second side of said front wall, wherein said primary drain is positioned below said top edge of said front wall; and,
    ii. a base plate engaged with a bottom surface of said main chamber, said base plate comprising:
      1. a main inlet in fluid communication with a sample fluid inlet line, wherein said sample fluid enters said flow cell via said main inlet; and,
      2. a base plate inlet in fluid communication with said main inlet and said sample fluid inlet port in said main chamber;
  d. stopping said flow of said sample fluid to said flow cell;
  e. selecting a wash fluid to flush a portion of said flow cell with said wash fluid;
  f. selecting said second sample fluid.

20. The method according to claim 19 further comprising the step of providing an auxiliary sample system between said sample fluid manifold and said flow cell, wherein said auxiliary sample system extracts a portion of said sample fluid.

* * * * *